(12) United States Patent
Tan et al.

(10) Patent No.: US 11,441,173 B2
(45) Date of Patent: Sep. 13, 2022

(54) OPTICAL INSTRUMENTS AND SYSTEMS FOR FORENSIC DNA QUANTITATION

(71) Applicant: ANDE Corporation, Waltham, MA (US)

(72) Inventors: Eugene Tan, Arlington, MA (US); Richard F. Selden, Lincoln, MA (US); Rosemary S. Turingan, Stoneham, MA (US)

(73) Assignee: ANDE CORPORATION, Waltham, MA (US)

( * ) Notice: Subject to any disclaimer, the term of this patent is extended or adjusted under 35 U.S.C. 154(b) by 433 days.

(21) Appl. No.: 16/729,224

(22) Filed: Dec. 27, 2019

(65) Prior Publication Data

US 2020/0248243 A1 Aug. 6, 2020

Related U.S. Application Data

(63) Continuation of application No. 15/410,399, filed on Jan. 19, 2017, now Pat. No. 10,538,804, which is a (Continued)

(51) Int. Cl.
*C12Q 1/6825* (2018.01)
*C12Q 1/6816* (2018.01)
(Continued)

(52) U.S. Cl.
CPC ...... *C12Q 1/6825* (2013.01); *B01L 3/502715* (2013.01); *B01L 7/52* (2013.01);
(Continued)

(58) Field of Classification Search
CPC .... B01L 3/5027; B01L 3/502715; B01L 7/52; B01L 2300/0627; B01L 2300/0654;
(Continued)

(56) References Cited

U.S. PATENT DOCUMENTS 4,170,616 A 10/1979 Jebens
4,751,177 A 6/1988 Stabinsky
(Continued)

FOREIGN PATENT DOCUMENTS

EP 1026258 A2 8/2000
EP 1614466 A2 1/2006
(Continued)

OTHER PUBLICATIONS

U.S. Appl. No. 13/044,485, filed Mar. 9, 2011, Selden et al.
(Continued)

*Primary Examiner* — Jennifer Wecker
*Assistant Examiner* — Alea N. Martin
(74) *Attorney, Agent, or Firm* — Proskauer Rose LLP

(57) ABSTRACT

Described herein are instruments for excitation and detection of fluorophores in a plurality of functional regions in a biochip, using an excitation source and a steering element that directs a beam from the excitation source to a plurality of functional regions in the biochip, wherein the excitation source excites the fluorophores in the plurality of functional regions generating a signal that is detected such that said signal from at least one of the plurality of functional regions allows for nucleic acid quantification. Also described are systems for quantification and separation and detection using optical devices adapted for preliminary, simultaneous or sequential quantitation of nucleic acid in separate detection positions, and for the excitation and detection of multiple samples to steer both the excitation and detection beam paths to separately image each lane of a biochip.

8 Claims, 27 Drawing Sheets

Specification includes a Sequence Listing.

Related U.S. Application Data continuation of application No. 12/816,370, filed on Jun. 15, 2010, now Pat. No. 9,550,985.

(60) Provisional application No. 61/268,770, filed on Jun. 15, 2009.

(51) Int. Cl.
  *C12N 15/10* (2006.01)
  *G02B 27/10* (2006.01)
  *G01N 15/14* (2006.01)
  *B01L 7/00* (2006.01)
  *B01L 3/00* (2006.01)
  *C12Q 1/6818* (2018.01)

(52) U.S. Cl.
  CPC ....... *C12N 15/1017* (2013.01); *C12Q 1/6816* (2013.01); *C12Q 1/6818* (2013.01); *B01L 3/5027* (2013.01); *B01L 2300/0627* (2013.01); *B01L 2300/0654* (2013.01); *B01L 2300/0819* (2013.01); *B01L 2300/0877* (2013.01); *B01L 2300/168* (2013.01); *G01N 15/1484* (2013.01); *G01N 2201/06113* (2013.01); *G02B 27/10* (2013.01); *Y10T 436/143333* (2015.01)

(58) Field of Classification Search
  CPC ..... B01L 2300/0819; B01L 2300/0877; B01L 2300/168; C12N 15/1017; C12Q 1/6816; C12Q 1/6818; C12Q 1/6825; C12Q 2563/107; C12Q 2565/629
  See application file for complete search history.

(56) References Cited

U.S. PATENT DOCUMENTS

| | | |
|---|---|---|
| 4,811,218 A | 3/1989 | Hunkapiller et al. |
| 4,832,815 A | 5/1989 | Kambara et al. |
| 4,855,225 A | 8/1989 | Fung et al. |
| 4,865,707 A | 9/1989 | Karger et al. |
| 4,881,812 A | 11/1989 | Ohkubo et al. |
| 4,945,135 A | 7/1990 | Grubbs |
| 5,112,460 A | 5/1992 | Karger |
| 5,126,022 A | 6/1992 | Soane et al. |
| 5,126,629 A | 6/1992 | Chopy |
| 5,164,055 A | 11/1992 | Dubrow |
| 5,171,534 A | 12/1992 | Smith et al. |
| 5,198,511 A | 3/1993 | Brown-Wensley |
| 5,234,809 A | 8/1993 | Boom et al. |
| 5,273,638 A | 12/1993 | Konrad et al. |
| 5,281,516 A | 1/1994 | Stapleton et al. |
| 5,290,418 A | 3/1994 | Menchen et al. |
| 5,307,148 A | 4/1994 | Kambara et al. |
| 5,312,940 A | 5/1994 | Grubbs |
| 5,332,666 A | 7/1994 | Prober et al. |
| 5,334,424 A | 8/1994 | Hani et al. |
| 5,342,909 A | 8/1994 | Grubbs |
| 5,462,995 A | 10/1995 | Hosaka et al. |
| 5,464,945 A | 11/1995 | Reynolds et al. |
| 5,468,365 A | 11/1995 | Menchen et al. |
| 5,561,208 A | 10/1996 | Takahasi et al. |
| 5,582,989 A | 12/1996 | Caskey et al. |
| 5,587,128 A | 12/1996 | Wilding et al. |
| 5,644,162 A | 7/1997 | Beilstein et al. |
| 5,663,129 A | 9/1997 | Emert |
| 5,681,741 A | 10/1997 | Atwood et al. |
| 5,723,294 A | 3/1998 | Glass et al. |
| 5,750,015 A | 5/1998 | Soane et al. |
| 5,770,029 A | 6/1998 | Nelson et al. |
| 5,779,868 A | 6/1998 | Parce et al. |
| 5,786,182 A | 7/1998 | Catanzariti et al. |
| 5,800,996 A | 9/1998 | Lee et al. |
| 5,821,058 A | 10/1998 | Smith et al. |
| 5,840,338 A | 11/1998 | Roos |
| 5,843,660 A | 12/1998 | Schumm et al. |
| 5,847,162 A | 12/1998 | Lee et al. |
| 5,858,187 A | 1/1999 | Ramsey et al. |
| 5,858,188 A | 1/1999 | Soane et al. |
| 5,858,195 A | 1/1999 | Ramsey et al. |
| 5,861,256 A | 1/1999 | Glass et al. |
| 5,876,675 A | 3/1999 | Kennedy |
| 5,882,856 A | 3/1999 | Shuber et al. |
| 5,897,842 A | 4/1999 | Dunn et al. |
| 5,922,544 A | 7/1999 | Miyai et al. |
| 5,925,517 A | 7/1999 | Tyagi et al. |
| 5,976,336 A | 11/1999 | Dubrow |
| 5,989,499 A | 11/1999 | Catanzariti et al. |
| 5,994,056 A | 11/1999 | Higuchi et al. |
| 5,994,064 A | 11/1999 | Staub et al. |
| 5,994,066 A | 11/1999 | Bergeron et al. |
| 6,017,434 A | 1/2000 | Simpson et al. |
| 6,017,765 A | 1/2000 | Yamada et al. |
| 6,100,541 A | 8/2000 | Nagle |
| 6,103,476 A | 8/2000 | Tyagi et al. |
| 6,120,667 A | 9/2000 | Hayashizaki et al. |
| 6,143,152 A | 11/2000 | Simpson |
| 6,150,097 A | 11/2000 | Tyagi et al. |
| 6,150,180 A | 11/2000 | Parce |
| 6,153,073 A | 11/2000 | Dubrow et al. |
| 6,156,181 A | 12/2000 | Parce |
| 6,156,512 A | 12/2000 | Schumm et al. |
| 6,167,910 B1 | 1/2001 | Chow |
| 6,180,372 B1 | 1/2001 | Franzen |
| 6,211,955 B1 | 4/2001 | Basiji et al. |
| 6,221,598 B1 | 4/2001 | Schumm et al. |
| 6,207,031 B1 | 5/2001 | Adourian et al. |
| 6,224,732 B1 | 5/2001 | Imasaka et al. |
| 6,225,061 B1 | 5/2001 | Becker et al. |
| 6,225,636 B1 | 5/2001 | Ginestet |
| 6,228,634 B1 | 5/2001 | Blumenfeld et al. |
| 6,235,175 B1 | 5/2001 | Dubrow et al. |
| 6,235,479 B1 | 5/2001 | Rogers |
| 6,251,247 B1 | 6/2001 | Mitsuhashi et al. |
| 6,280,589 B1 | 8/2001 | Manz et al. |
| 6,292,499 B1 | 9/2001 | Pearson et al. |
| 6,302,134 B1 | 10/2001 | Kellogg et al. |
| 6,312,886 B1 | 11/2001 | Lee et al. |
| 6,316,781 B1 | 11/2001 | Nagle |
| 6,321,791 B1 | 11/2001 | Chow |
| 6,329,661 B1 | 12/2001 | Perov |
| RE37,606 E | 3/2002 | Guttman |
| 6,358,387 B1 | 3/2002 | Kopf-Sill |
| 6,361,672 B1 | 3/2002 | Zhu et al. |
| 6,372,142 B1 | 4/2002 | Gjerde et al. |
| 6,391,541 B1 | 5/2002 | Petersen et al. |
| 6,403,367 B1 | 6/2002 | Cheng et al. |
| 6,407,395 B1 | 6/2002 | Perov |
| 6,409,900 B1 | 6/2002 | Parce |
| 6,410,275 B1 | 6/2002 | Kluttz et al. |
| 6,413,766 B2 | 7/2002 | Landers et al. |
| 6,413,782 B1 | 7/2002 | Parce |
| 6,420,143 B1 | 7/2002 | Kopf-Sill et al. |
| 6,428,987 B2 | 8/2002 | Franzen |
| 6,429,007 B1 | 8/2002 | Kluttz et al. |
| 6,431,476 B1 | 8/2002 | Taylor et al. |
| 6,432,290 B1 | 8/2002 | Harrison et al. |
| 6,440,725 B1 | 8/2002 | Pourahmadi et al. |
| 6,444,461 B1 | 9/2002 | Knapp et al. |
| 6,458,537 B1 | 10/2002 | White et al. |
| 6,471,916 B1 | 10/2002 | Noblett |
| 6,472,155 B1 | 10/2002 | McKinney |
| 6,472,156 B1 | 10/2002 | Wittwer et al. |
| 6,479,235 B1 | 11/2002 | Schumm et al. |
| 6,479,299 B1 | 11/2002 | Parce |
| 6,485,625 B1 | 11/2002 | Simpson et al. |
| RE37,941 E | 12/2002 | Guttman |
| 6,494,230 B2 | 12/2002 | Chow |
| 6,498,353 B2 | 12/2002 | Nagle |
| 6,524,830 B2 | 2/2003 | Kopf-Sill |
| 6,531,044 B1 | 3/2003 | Anazawa et al. |
| 6,531,282 B1 | 3/2003 | Dau et al. |
| 6,563,584 B1 | 5/2003 | Yurino et al. |
| 6,586,253 B1 | 7/2003 | Harrison et al. |
| 6,598,545 B2 | 7/2003 | Ryaboy et al. |

(56) References Cited

U.S. PATENT DOCUMENTS

| | | |
|---|---|---|
| 6,602,472 B1 | 8/2003 | Zimmermann |
| 6,605,472 B1 | 8/2003 | Skinner et al. |
| 6,606,273 B1 | 8/2003 | Guo et al. |
| 6,630,063 B1 | 10/2003 | Li et al. |
| 6,630,680 B2 | 10/2003 | Hakamata et al. |
| 6,633,785 B1 | 10/2003 | Kasahara et al. |
| 6,635,487 B1 | 10/2003 | Lee |
| 6,646,271 B2 | 11/2003 | Yokokawa |
| 6,648,015 B1 | 11/2003 | Chow |
| 6,664,057 B2 | 12/2003 | Albertson et al. |
| 6,664,080 B1 | 12/2003 | Pfeffer |
| 6,664,104 B2 | 12/2003 | Pourahmadi et al. |
| 6,709,869 B2 | 3/2004 | Mian et al. |
| 6,733,645 B1 | 5/2004 | Chow |
| 6,733,648 B2 | 5/2004 | Okano et al. |
| 6,764,512 B2 | 7/2004 | Keller |
| 6,774,616 B2 | 8/2004 | Huhn et al. |
| 6,787,016 B2 | 9/2004 | Tan |
| 6,790,952 B2 | 9/2004 | Groen et al. |
| 6,800,438 B2 | 10/2004 | Noolandi et al. |
| 6,824,024 B2 | 11/2004 | Ingenhoven et al. |
| 6,826,524 B1 | 11/2004 | Kim et al. |
| 6,830,936 B2 | 12/2004 | Anderson et al. |
| 6,849,407 B2 | 2/2005 | Espy et al. |
| 6,857,449 B1 | 2/2005 | Chow et al. |
| 6,864,050 B2 | 3/2005 | Su et al. |
| 6,864,571 B2 | 3/2005 | Arik et al. |
| 6,893,879 B2 | 5/2005 | Petersen et al. |
| 6,893,897 B2 | 5/2005 | Sweterlitsch |
| 6,916,614 B1 | 7/2005 | Takenaka |
| 6,929,730 B2 | 8/2005 | Lee |
| 6,949,376 B2 | 9/2005 | Kluttz et al. |
| 6,952,008 B2 | 10/2005 | Corson |
| 6,958,210 B2 | 10/2005 | Smith et al. |
| 6,960,286 B2 | 11/2005 | Manz et al. |
| 6,987,018 B2 | 1/2006 | Taylor |
| 6,991,713 B2 | 1/2006 | Adourian et al. |
| 7,008,771 B1 | 3/2006 | Schumm et al. |
| 7,029,562 B2 | 4/2006 | Anazawa et al. |
| 7,033,474 B1 | 4/2006 | Dubrow |
| 7,038,775 B2 | 5/2006 | Sakai |
| 7,060,948 B2 | 6/2006 | Cho et al. |
| 7,069,952 B1 | 7/2006 | McReynolds |
| 7,074,598 B2 | 7/2006 | Cockerill, III et al. |
| 7,074,599 B2 | 7/2006 | Uhl et al. |
| 7,141,372 B2 | 11/2006 | Spivack et al. |
| 7,142,738 B2 | 11/2006 | Lee et al. |
| 7,150,299 B2 | 12/2006 | Hertzler et al. |
| 7,205,111 B2 | 4/2007 | Christensen et al. |
| 7,199,376 B2 | 7/2007 | Prange et al. |
| 7,261,859 B2 | 8/2007 | Andersson et al. |
| 7,264,950 B1 | 9/2007 | Lee et al. |
| 7,277,284 B2 | 10/2007 | Lee et al. |
| 7,280,204 B2 | 10/2007 | Robinson et al. |
| 7,288,405 B2 | 10/2007 | Shuler et al. |
| 7,300,199 B2 | 11/2007 | Andersson et al. |
| 7,306,924 B2 | 12/2007 | Gomez et al. |
| 7,312,036 B2 | 12/2007 | Sampath et al. |
| 7,312,611 B1 | 12/2007 | Harrison et al. |
| 7,326,779 B2 | 2/2008 | Nakano et al. |
| 7,332,126 B2 | 2/2008 | Tooke et al. |
| RE42,325 E | 5/2011 | Wittwer et al. |
| 2001/0041332 A1 | 11/2001 | Hillebrand et al. |
| 2001/0046667 A1 | 11/2001 | Cloyd et al. |
| 2002/0009741 A1 | 1/2002 | Simpson et al. |
| 2002/0037520 A1 | 3/2002 | Nikiforov et al. |
| 2002/0042125 A1 | 4/2002 | Petersen et al. |
| 2002/0042151 A1 | 4/2002 | Chen |
| 2002/0046949 A1 | 4/2002 | Nakamura et al. |
| 2002/0055167 A1 | 5/2002 | Pourahmadi et al. |
| 2002/0056639 A1 | 5/2002 | Lackritz et al. |
| 2002/0060156 A1 | 5/2002 | Mathies et al. |
| 2002/0076927 A1 | 6/2002 | Henderson et al. |
| 2002/0146734 A1 | 10/2002 | Ortyn |
| 2002/0155485 A1 | 10/2002 | Kao |
| 2003/0008286 A1 | 1/2003 | Zou et al. |
| 2003/0020022 A1 | 1/2003 | Kuwabata et al. |
| 2003/0021016 A1 | 1/2003 | Grier |
| 2003/0058440 A1 | 3/2003 | Scott et al. |
| 2003/0082080 A1 | 5/2003 | Zimmermann |
| 2003/0087300 A1 | 5/2003 | Knapp et al. |
| 2003/0089605 A1 | 5/2003 | Timperman |
| 2003/0118477 A1 | 6/2003 | Liljestrand et al. |
| 2003/0127609 A1* | 7/2003 | El-Hage ............ G01N 21/6452 250/574 |
| 2003/0134431 A1 | 7/2003 | Parce |
| 2003/0143575 A1 | 7/2003 | Caria et al. |
| 2003/0143587 A1 | 7/2003 | Dean et al. |
| 2003/0146145 A1 | 8/2003 | Krotz et al. |
| 2003/0152927 A1 | 8/2003 | Jakobsen et al. |
| 2003/0155966 A1 | 8/2003 | Harrison et al. |
| 2003/0007898 A1 | 9/2003 | Bohm |
| 2003/0175782 A1 | 9/2003 | Fukushima et al. |
| 2003/0180724 A1 | 9/2003 | Schumm et al. |
| 2003/0186272 A1 | 10/2003 | Dau et al. |
| 2003/0190608 A1 | 10/2003 | Blackburn |
| 2003/0211631 A1 | 11/2003 | Skinner et al. |
| 2004/0009518 A1 | 1/2004 | Lo et al. |
| 2004/0018611 A1 | 1/2004 | Ward et al. |
| 2004/0048270 A1 | 3/2004 | Zeltz et al. |
| 2004/0062468 A1 | 4/2004 | Lee |
| 2004/0105932 A1 | 6/2004 | Goldberg et al. |
| 2004/0109793 A1 | 6/2004 | McNeely et al. |
| 2004/0115094 A1 | 6/2004 | Gumbrecht et al. |
| 2004/0126279 A1 | 7/2004 | Renzi et al. |
| 2004/0137504 A1 | 7/2004 | Schumm et al. |
| 2004/0168916 A1 | 9/2004 | Fuchs et al. |
| 2004/0178071 A1 | 9/2004 | Harrison et al. |
| 2004/0185467 A1 | 9/2004 | Kauvar et al. |
| 2004/0197816 A1 | 10/2004 | Empedocles et al. |
| 2004/0197845 A1 | 10/2004 | Hassibi et al. |
| 2004/0209354 A1 | 10/2004 | Mathies et al. |
| 2004/0224325 A1 | 11/2004 | Knapp et al. |
| 2004/0259237 A1 | 12/2004 | Kellogg et al. |
| 2005/0019902 A1 | 1/2005 | Mathies et al. |
| 2005/0053952 A1 | 3/2005 | Hong et al. |
| 2005/0059027 A1 | 3/2005 | Chung |
| 2005/0064575 A1 | 3/2005 | Belgrader et al. |
| 2005/0074784 A1 | 4/2005 | Vo Dinh et al. |
| 2005/0106612 A1 | 5/2005 | Amirkhanian |
| 2005/0109621 A1 | 5/2005 | Hauser et al. |
| 2005/0129582 A1 | 6/2005 | Breidford et al. |
| 2005/0135655 A1 | 6/2005 | Kopf-Sill et al. |
| 2005/0164407 A1 | 7/2005 | Stabler et al. |
| 2005/0179901 A1 | 8/2005 | Ostlin |
| 2005/0181440 A1 | 8/2005 | Chee et al. |
| 2005/0194316 A1 | 9/2005 | Pourahmadi et al. |
| 2005/0287572 A1 | 12/2005 | Mathies et al. |
| 2006/0009106 A1 | 1/2006 | Nishimura et al. |
| 2006/0030796 A1 | 2/2006 | Xu et al. |
| 2006/0035231 A1 | 2/2006 | Van Beuningen et al. |
| 2006/0057629 A1 | 3/2006 | Kim et al. |
| 2006/0068431 A1 | 3/2006 | Lee et al. |
| 2006/0099614 A1 | 5/2006 | Gill et al. |
| 2006/0105354 A1 | 5/2006 | Remacle et al. |
| 2006/0134616 A1 | 6/2006 | Belgrader et al. |
| 2006/0141446 A1 | 6/2006 | Murphy et al. |
| 2006/0166223 A1 | 7/2006 | Reed et al. |
| 2006/0213964 A1 | 9/2006 | Excoffier et al. |
| 2006/0246501 A1 | 11/2006 | Northrup |
| 2006/0246580 A1 | 11/2006 | Kim et al. |
| 2006/0257958 A1 | 11/2006 | Bruno |
| 2006/0260941 A1 | 11/2006 | Tan et al. |
| 2006/0286552 A1 | 12/2006 | Goldsmith |
| 2007/0116607 A1 | 5/2007 | Wang et al. |
| 2007/0154355 A1 | 7/2007 | Berndt et al. |
| 2007/0154881 A1 | 7/2007 | Koo |
| 2007/0154895 A1 | 7/2007 | Spaid et al. |
| 2007/0178471 A1 | 8/2007 | Gildea et al. |
| 2007/0184547 A1 | 8/2007 | Handique et al. |
| 2007/0206187 A1 | 9/2007 | Lundquist et al. |
| 2007/0224605 A1 | 9/2007 | An et al. |
| 2007/0264658 A1 | 11/2007 | Pollner et al. |
| 2008/0003588 A1 | 1/2008 | Hasson et al. |

(56) References Cited

U.S. PATENT DOCUMENTS

| | | | |
|---|---|---|---|
| 2008/0085521 | A1 | 4/2008 | Knapp et al. |
| 2009/0020427 | A1 | 1/2009 | Tan et al. |
| 2009/0023603 | A1 | 1/2009 | Selden et al. |
| 2009/0059222 | A1 | 3/2009 | Tan et al. |
| 2009/0081670 | A1 | 3/2009 | Maples et al. |
| 2009/0087857 | A1 | 4/2009 | Carell et al. |
| 2009/0229983 | A1 | 9/2009 | Tan et al. |
| 2010/0285578 | A1 | 11/2010 | Selden et al. |
| 2011/0312614 | A1 | 12/2011 | Selden et al. |

FOREIGN PATENT DOCUMENTS

| | | |
|---|---|---|
| EP | 1710017 A1 | 10/2006 |
| JP | S61162752 A1 | 7/1986 |
| JP | 2005-503753 A | 2/2005 |
| WO | WO1989/09437 | 10/1989 |
| WO | WO1996/021041 A | 11/1996 |
| WO | WO1999/19717 | 4/1999 |
| WO | WO1999/39005 | 8/1999 |
| WO | WO2001/41931 A2 | 6/2001 |
| WO | WO2001/88204 A1 | 11/2001 |
| WO | WO2001/92575 A1 | 12/2001 |
| WO | WO2002/022874 A2 | 3/2002 |
| WO | WO2002/024322 A2 | 3/2002 |
| WO | WO2002/35223 A1 | 5/2002 |
| WO | WO2002/056004 A2 | 7/2002 |
| WO | WO2002/063288 A1 | 8/2002 |
| WO | WO2002/097398 A2 | 12/2002 |
| WO | WO2003/031646 A1 | 4/2003 |
| WO | WO2004/052527 A1 | 6/2004 |
| WO | WO2005/029062 A2 | 3/2005 |
| WO | WO2005/073691 A1 | 8/2005 |
| WO | WO2006/032044 A2 | 3/2006 |
| WO | WO2006/116362 A2 | 11/2006 |
| WO | WO2006/124842 A2 | 11/2006 |
| WO | WO2006/128321 A1 | 12/2006 |
| WO | WO2007/021814 A1 | 2/2007 |
| WO | WO2008/124104 A1 | 10/2008 |
| WO | WO2008/124116 A1 | 10/2008 |
| WO | WO2009/049268 A1 | 4/2009 |
| WO | WO2009/108260 A2 | 9/2009 |
| WO | WO2010/147654 A2 | 12/2010 |
| WO | WO2011/112746 A2 | 9/2011 |

OTHER PUBLICATIONS

Albarghourhi et al., "Polymeric matrices for DNA sequencing by capillary electrophoresis", Electrophoresis, (2000), vol. 21, pp. 4096-4111.
Ali et al., "DNA hybridization and discrimination of single-nucleotide mismatches using chip-based microbead arrays", Anal Chem., vol. 75, No. 18, (2003), pp. 4732-4739.
Alonso et al., "Real-time PCR designes to estimate nuclear and mitochondrial DNA copy number in forensic and ancient DNA studies", Forensic Sci. Int., vol. 139 (2-3), (2004), pp. 141-149.
Auroux et al.,"Micro total analysis systems. 2. Analytical standard operations and applications", Anal. Chem., vol. 74, (2002), pp. 2637-2652.
Becker et al., "Polymer microfabrication methods for microfluidic analytical applications", Electrophoresis, vol. 21, (2000), pp. 12-26.
Becker et al., "Polymer microfabrication technologies for microfluidic systems", Anal and Bioanal. Chem., vol. 390, No. 1, (2008), p. 89.
Beckman et al., "Survey of human and rate microsatellites", Genomics, vol. 12, (1992), pp. 627-631.
Bhattacharyya et al., "Thermoplastic microfluidic device for on-chip nucleic acids for disposable diagnostics", Anal. Chem., Feb. 1, 2006, vol. 78, No. 3, pp. 788-792.
Blazej et al., "Microfabricated bioprocessor for integrated nanoliter-scale Sanger DNA sequencing", Proc. Natl. Acad. Sci. USA, May 9, 2006, vol. 103, No. 19, pp. 7240-7245. Epub Apr. 28, 2006.

Bosserhoff et al., "Use of capillary electrophoresis for high through-put screening in biomedical applications, a minireview", Combinational Chemistry and High Throughput Screening, vol. 3, (2000), pp. 455-466.
Botstein et al., Construction of a genetic linkage map in man using restriction fragment length polymorphisms, Am. J. Hum. Genet., May 1980, vol. 32, No. 1, pp. 314-331.
Budowle et al., "CODIS and PCR based short tandem report loci: law enforcement tools", Second European Symposium on Human Identification, (1998), pp. 73-88.
Budowle et al., "Using a CCD camera imaging system as a recording device to quantify human DNA by slot blot hybridization", Biotechniques, (2001), vol. 30, No. 3, pp. 680-685.
Burns et al., "An integrated nanoliter DNA analysis device", Science, (1998), vol. 282, pp. 484-487.
Chen et al., "DNA hybridization detection in a microfluidic channel using two fluorescently labelled nucleic acid probes", Biosensors and Bioelectronics, (2008), vol. 23, pp. 1878-1882.
Chen et al., "Thermally-actuated, phase change flow control for microfluidic systems", Lab on a Chip, (2005), vol. 5, pp. 1277-1285.
Chiou et al., "A closed-cycle capillary polymerase chain reaction machine", Anal. Chem., (2001), vol. 73, pp. 2018-2021.
Clayton, "Go with the microflow", Nature Materials, (2005), vol. 2, No. 8, pp. 621-626.
Dittrich et al., "Micro total analysis systems. Latest advancements and trends", Anal. Chem., (2006), vol. 78, pp. 3887-3907.
DNA/RNA Copy Number Calculator available at endmemo.com [retrieved on Feb. 7, 2014], Retrieved from the Internet: <URL: www.endmemo.com/bio/dnacopynum/php>.
DNA/RNA Copy Number Calculator available at endmemo.com [retrieved on Feb. 10, 2014], Retrieved from the Internet: <URL: www.endmemo.com/bio/dnacopynum/php>.
Duewer et al., "NIST mixed stain studies #1 and #2: interlaboratory comparison of DNA quantification practice and short tandem repeat multiplex performance with multiple-source samples", J Forensic Sci., (2001), vol. 46, No. 5, pp. 1199-1210.
Easley et al., "A fully integrated microfluidic genetic analysis system with sample-in-answer-out capability", PNAS, (2006), vol. 103, No. 51, p. 19272-7.
Edwards et al., "Automated DNA sequencing methods for detection and analysis of mutations: applications to the Lesch-Nyhan syndrome", Trans Assoc. Am. Physicians, (1989), vol. 102, pp. 185-194.
Edwards et al., "DNA typing and genetic mapping with trimeric and tetrameric tandem repeats", Am J Hum Genet, (1991), vol. 49, No. 4, pp. 746-756.
Espy et al., "Real-time PCR in clinical microbiology: applications for routine laboratory testing", Clin. Microbiol. Rev., (2006), vol. 19, pp. 165-256.
Ewing et al., "Base-calling of automated sequencer traces using Phred I. Accuracy Assessment", Genome Res., (1998), vol. 8, pp. 175-185.
Ewing et al., "Base-calling of automated sequencer traces using Phred II. Error Probabilities", Genome Res., (1998), vol. 8, pp. 186-194.
Ferrance et al., "Exploiting sensitive laser-induced fluorescence detection on electrophoretic microchips for executing rapid clinical diagnostics", Luminscence, (2001), vol. 16, pp. 79-88.
Fiorini et al., "Disposable microfluidic devices: fabrication, function, and application", BioTechniques, (2005), vol. 38, pp. 429-446.
Fox et al., "Development, characterization, and validation of a sensitive primate-specific quantification assay for forensic analysis", BioTechniques, (2003), pp. 314-318, 320, 322.
Geiss et al., "Direct multiplexed measurement of gene expression with color-coded probe pairs", Nature Biotech,. (2008), vol. 26, No. 3, pp. 317-325.
Gerstner et al., "Near-infrared dyes for six-color immunophenotyping by laser scanning cytometry", Cytometry, (2002), vol. 48, No. 3, pp. 115-123.
Giese et al., "Fast multiplexed polymerase chain reaction for conventional and microfluidic short tandem repeat analysis", J Forensic Sci., (2009), vol. 54, No. 6, pp. 1287-1296.
Gill et al., "Application of low copy number DNA profiling", Croat Med. J, (2001), vol. 42, pp. 229-232.

(56) References Cited

OTHER PUBLICATIONS

Goedecke et al., "A high-performance multilane microdevice system designed for the DNA forensics laboratory", Electrophoresis, (2004), vol. 25, pp. 1678-1686.
Harrison et al., "Capillary electrophoresis and sample injection systems integrated on a planar glass chip", Anal. Chem., (1992), vol. 64, pp. 1926-1932.
Hawkins, "Nonlinear decrease of background fluorescence in polymer thin-films—a survey of materials and how they can complicate fluorescence detection in µTAS", Lab Chip, (2003), vol. 3, No. 4, pp. 248-252.
Hayn et al., "Evaluation of an automated liquid hybridization method for DNA quantitation", J Forensic Sci., (2004), vol. 49, No. 1, pp. 87-91.
Heid et al., "Real time quantitative PCR", Genome Res., (1996), vol. 6, pp. 986-994.
Henegariu et al., "Multiplex PCR: critical parameters and step-by-step protocol", Biotechniques, (1997), vol. 23, pp. 504-511.
Hill et al., "A 26plex autosomall STR assay to aid human identity testing", J Forensic Sci., (2009), vol. 54, No. 5, pp. 1008-1015.
Holland et al., "Detection of specific polymerase chain reaction product by utilizing the 5'----3' exonuclease activity of Thermus aquaticus DNA polymerase", PNAS, (1991), vol. 88, No. 16, pp. 7276-7280.
Holt et al., "TWGDAM validation of AplFISTR PCR amplification kits for forensic DNA casework", J Forensic Sci., (2002), vol. 47, No. 1, pp. 66-96.
Hopwood et al., "Forensic response vehicle: rapid analysis of evidence at the scene of a crime", International Congress Series, (2006), vol. 1288, pp. 66-96.
Hopwood et al., "Rapid quantification of DNA samples extracted from buccal scrapes prior to DNA profiling", Biotechniques, (1997), vol. 23, No. 1, pp. 18-20.
Horsman et al., "Forensic DNA analysis on microfluidic devices: a review", J Forensic Sci., (2007), vol. 52, pp. 784-799.
Huang et al., "An integrated microfluidic chip for DNA/RNA amplification, electrophoresis separation, and on-line optical detection", Electrophoresis, (2006), vol. 27, pp. 3297-3305.
Ibrahim et al., "Real-time microchip PCR for detecting single-base differences in viral and human DNA", Anal. Chem., May 1, 1998, vol. 70, No. 9, pp. 2013-2017.
International Search Report for PCT/US2006/18838 dated Aug. 30, 2007.
International Search Report for PCT/US2011/027787 dated Nov. 18, 2011.
International Search Report and Written Opinion for PCT/US2008/004487 dated Aug. 27, 2008.
International Preliminary Report on Patentability for PCT/US2008/004487 dated Oct. 15, 2009.
Invitation to Pay Additional Fees for PCT/2010/001741 dated Oct. 8, 2010.
International Search Report and Written Opinion for PCT/2010/001741 dated Dec. 2, 2010.
International Preliminary Report on Patentability for PCT/US2010/001741 dated Dec. 29, 2011.
Janasek et al., "Scaling and the design of miniaturized chemical-analysis systems", Nature, (2006), vol. 442, pp. 374-380.
Jung et al., "Fast and sensitive DNA analysis using changes in the FRET signals of molecular beacons in a PDMS microfluidic channel", Anal. Bioanal. Chem., (2007), vol. 387, pp. 2609-2615.
Kamentsky et al., "Slide-based laser scanning cytometry", Acta Cytologica, International Academy of Cytology, Chicago, IL, (1997), vol. 41, No. 1, pp. 123-143.
Kan et al., "DNA sequencing and genotyping in miniaturized electrophoresis systems", Electrophoresis, (2004), vol. 25, No. 21-22, pp. 3564-3588.
Kim et al., "Rapid DNA hybridization analysis using a PDMS microfluidic sensor and a molecular beacon", Anal. Sci., (2007), vol. 23, pp. 401-405.

Kline et al., "NIST Mixed Stain Study 3: DNA quantitation accuracy and its influence on short tandem repeat multiplex signal intensity", Anal. Chem., (2003), vol. 75, No. 10, pp. 2463-2469.
Krasnoperov et al., "Luminescent Probes for Ultrasensitive Detection of Nucleic Acids", Bioconjug. Chem., (2010), vol. 21, pp. 319-327.
Krenke et al., "Validation of a 16-locus fluorescent multiplex system", J Forensic Sci., (2002), vol. 47, No. 4, pp. 773-785.
Lafountain et al., "TWGDAM validation of the AmpFISTR profiler plus and AmpFISTR COFiler STR multiplex systems using capillary electrophoresis", J Forensic Sci., (2001), vol. 46, No. 5, pp. 1191-1198.
Leclair et al., "Systemic analysis of stutter percentages and allele peak height and peak area ratios at heterozygous STR loci to forensic casework and database samples", J Forensic Sci., (2004), vol. 49, pp. 968-980.
Li et al., "An estimate of the crosstalk matrix in four-dye fluorescence-based DNA sequencing", Electrophoresis, (1999), vol. 20, No. 1, pp. 1433-1442.
Liu et al., "Automated parallel DNA sequencing on multiple channel microchips", PNAS, (2000), vol. 97, No. 10, pp. 5369-5374.
Liu et al., "DNA amplification and hybridization assays in integrated plastic monolithic devices", Anal. Chem., (2002), vol. 74, pp. 3063-3070.
Liu et al., "Integrated microfluidic systems for high-performance genetic analysis", Trends Biotechnol, Oct. 2009, vol. 10, pp. 572-581. Epub Aug. 24, 2009.
Liu et al., "Integrated portable polymerase chain reaction-capillary electrophoresis microsystem for rapid forensic short tandem repeat typing", Anal. Chem., (2007), vol. 79, pp. 1881-1889.
Liu et al., "Self-contained, fully integrated biochip for sample preparation, polymerase chain reaction amplification, and DNA microarray detection", Anal. Chem., Apr. 1, 2004, vol. 76, No. 7, pp. 1824-1831.
Mandrekar et al., "Development of a human DNA quantitation system", Croat Med J, (2001), vol. 42, No. 3, pp. 336-339.
Maxam et al., "A new method for sequencing DNA", PNAS, (1977), vol. 74, pp. 560-564.
McCormick et al., "Microchannel electrophoretic separations of DNA in injection-molded plastic substrates", Anal. Chem., (1997), vol. 69, No. 14, pp. 2626-2630.0.
Metzker et al., "Emerging technologies in DNA sequencing", Genome Res., (2005), vol. 15, pp. 1767-1776.
Milligan et al., "Current concepts in antisense drug design", J Med. Chem., (1993), vol. 36, pp. 1923-1937.
Mitnik et al., "High-speed analysis of multiplexed short tandem repeats with an electrophoretic microdevice", Electrophoresis, (2002), vol. 23, pp. 719-726.
Mittag et al., "Polychromatic (eight-color) slide-based cytometry for the phenotyping of leukocyte, NK, and NKT subsets", Cytometry, (2005-06), vol. 65A, No. 2, pp. 103-115.
Moretti et al., "Validation of short tandem repeats (STRs) for forensic usage: performance testing of fluorescent multiplex STR systems and analysis of authentic and simulated forensic samples", J Forensic Sci., (2001), vol. 46, No. 3, pp. 647-660.
Nazarenko et al., "A closed tube format for amplification and detection of DNA based on energy transfer", Nucleic Acids Res., (1997), vol. 25, No. 12, pp. 2516-2521.
Nicklas et al., "Development of an Alu-based, QSY 7-labeled primer PCR method for quantitation of human DNA in forensic samples", J Forensic Sci., (2003), vol. 48, No. 2, pp. 282-291.
Nicklas et al., "Development of an Alu-based, real-time PCR method for quantitation of human DNA in forensic samples", J Forensic Sci., (2003), vol. 48, No. 5, pp. 936-944.
Nicklas et al., "Quantification of DNA in forensic samples", Anal. Bioanal. Chem., (2003), vol. 376, No. 8, pp. 1160-1167.
[No. Author Listed], "Micronics licenses "molecular beacons" from UMDNJ's PHRI properties", http://www.technoloqytransfertactics.com/content/2009/06/10/microics-licenses-molecular-beacons-from-umdnjs-phri-properties/, (2009).
Paegel et al., "High throughput DNA sequencing with a microfabricated 96-lane capillary array electrophoresis bioprocessor", PNAS, (2002), vol. 99, No. 2, pp. 574-579.

(56) References Cited

OTHER PUBLICATIONS

Pal et al., "An integrated microfluidic device for influenza and other genetic analyses", Lab Chip, (2005), vol. 5, pp. 1024-1032.
Promega Biomath Calculator 1 [retrieved on Jun. 10, 2015], Retrieved from the Internet: <URL: www.promega.com/a/apps/biomath/index.html?calc_pmolulugml>.
Promega Biomath Calculator 2 [retrieved on Jun. 10, 2015], Retrieved from the Internet: <URL: www.promega.com/a/apps/biomath/index.html?calc_pmolulugml>.
Pursika et al., "The autofluorescence of plastic materials and chips measured under laser irradiation", Lab Chip, (2005), vol. 5, No. 12, pp. 1348-1354.
Read et al., "Rapid multi-locus sequence typing using microfluidic biochip", PLoS ONE, (2010), e10595.
Reyes et al., "Micro total analysis systems. 1. Introduction, theory, and technology", Anal. Chem., (2002), vol. 74, pp. 2623-2636.
Ruiz-Martinez et al., "DNA sequencing by capillary electrophoresis with replaceable linear polyacrylamide and laser-induced fluorescence detection", Anal. Chem., (1993), vol. 65, pp. 2851-2858.
Rye et al., "Fluorometric assay using dimeric dyes for double- and single-stranded DNA and RNA with pictogram sensitivity", Anal. Biochem., (1993), vol. 208, No. 1, pp. 144-150.
Sanger et al., "DNA sequencing with chain-terminating inhibitors", PNAS, (1977), vol. 74, pp. 5463-5467.
Sassi et al., "Rapid, parallel separations of D1S80 alleles in a plastic microchannel chip", J Chromatogr. A., (2000), vol. 894, No. 1-2, pp. 203-213.
Schmalzing et al., "DNA typing in thirty seconds with a microfabricated device", Proc. Natl. Acad. Sci. USA, (1997), vol. 94, pp. 10273-10278.
Schmidt et al., "Low-volume amplification on chemically structured chips using the powerplex 16 DNA amplification kit", Int J Legal Med, (2006), vol. 120, pp. 42-48.
"Scientific Working Group on DNA Analysis Methods, Short Tandem Repeat (STR) Interpretation Guidelines", Forensic Science Communications, (2000), vol. 2, No. 3.
Shewale et al., "Human genomic DNA quantitation system, H-Quant: development and validation for use in forensic casework", J Forensic Sci., (2007), vol. 52, No. 2, pp. 364-370.
Shi et al., "High-resolution single stranded DNA analysis on 4.5 cm plastic electrophoretic microchannels", Electrophoresis, (2003), vol. 24, No. 19-20, pp. 3371-3377.
Shi, "DNA sequencing and multiplex STR analysis on plastic microfluidic devices", Electrophoresis, (2006), vol. 27, No. 10, pp. 3703-3711.
Shrinivasan et al., "A low-cost, low-power consumption, miniature laser-induced fluorescence system for DNA detection on a microfluidic device", Clin Lab Med, (2007), vol. 27, pp. 173-181.
Sifis et al., "A more sensitive method for the quantitation of genomic DNA by Alu amplification", J Forensic Sci., (2002), vol. 47, No. 3, pp. 589-592.
Simpson et al., "High-throughput genetic analysis using microfabricated 96-sample capillary array electrophoresis microplates", PNAS, (1998), vol. 95, pp. 2256-2261.
Singer et al., "Characterization of PicoGreen reagent and development of a fluorescence-based solution assay for double-stranded DNA quantitation", Anal. Biochem., (1997), vol. 249, No. 2, pp. 228-238.
Situma et al., "Immobilized molecular beacons: a new strategy using UV-activated poly(methylmethacrylate) surface to provide large fluorescence sensitivities for reporting on molecular association events", Anal. Biochem., (2007), vol. 363, pp. 35-45.
Skelley et al., "Development and evaluation of a microdevice for amino acid biomarker detection and analysis on Mars", PNAS, (2005), vol. 102, No. 4, pp. 1041-1046.
Strauss-Soukup et al., "Effects of neutralization pattern and stereochemistry on DNA bending by methylphosphonate substitutions", Biochem., (1997), vol. 36, pp. 8692-8698.

Summit et al., "Pressure enhances thermal stability of DNA polymerase from three thermophilic organisms", Extremeophiles, (1998), vol. 2, pp. 339-345.
Swango et al., "A quantitative PCR assay for the assessment of DNA degradation in forensic samples", Forensic Sci Int., (2006), vol. 158, No. 1, pp. 14-26.
Swango et al., "Developmental validation of a multiplex qPCR assay for assessing the quantity and quality of nuclear DNA in forensic samples", Forensic Sci Int., (2007), vol. 170, No. 1, pp. 35-45.
Takahashi et al., "Evaluation of the NanoChip 400 system for detection of influenza A and B, respiratory syncytial and parainfluenza viruses", J Clin Microbiol., May 2008, vol. 46, No. 5, pp. 1724-1727.
Tanious et al., "DAPI (4',6-diamidino-2-phenylindole) binds differently to DNA and RNA: minor-groove binding at AT sites and intercalation at AU sites", Biochemistry, (1992), vol. 31, No. 12, pp. 3103-3112.
Tomsey et al., "Comparison of PowerPlex 16, PowerPlex1.1/2.1, and ABI AmpflSTR Profiler Plus/COfiler for forensic use", Croat Med J, (2001), vol. 42, No. 3, pp. 239-243.
Tsao et al., "Bonding of thermoplastic polymer microfluidics", Microfluid Nanofluid, (2009), vol. 6, pp. 1-16.
Vallone et al., "Uses of the NIST 26plex STR assay for human identity testing", Forensic Science International: Genetics Supplement, (2009), vol. 2, pp. 29-30.
Van Dyke et al., "Automated systems for the fluorometric determination of nucleic acids by the ethidium bromide technique", Anal. Biochem., (1968), vol. 23, No. 1, pp. 109-116.
Verheggen et al., "Simple sampling device for capillary isotachophoresis and capillary zone electrophoresis", Journal of Chromatography, (1988), vol. 452, pp. 615-622.
Virus Genomes [retrieved on Feb. 6, 2014], Retrieved from the Internet: <URL: www.microbiologybytes.com/introduction/genomes.html>.
Wabuyele et al., "Single molecule detection of double-stranded DNA in poly(methylmethacrylate) and polycarbonate microfluidic devices", Electrophoresis, (2001), vol. 22, No. 18, pp. 3939-3940.
Walsh et al., "A rapid chemiluminescent method for quantitation of human DNA", Nucleic Acids Res., (1992), vol. 20, No. 19, pp. 5061-5065.
Walsh et al., "Amplification of alleles: mechanisms and solutions", PCR Methods Appl., (1992), vol. 1, pp. 241-250.
Walsh et al., "Sequence analysis and characterization of stutter products at the tetranucleotide repeat locus of vWA", Nucleic Acids Res., (1996), vol. 24, No. 14, pp. 2807-2812.
Wang et al., "A disposable microfluidic cassette for DNA amplification and detection", Lab on a Chip, (2006), vol. 6, pp. 46-53.
Wang et al., "Self-actuated, thermos-responsive hydrogel valves for lab on a chip", Biomed Microdevices, (2005), vol. 7, No. 4, pp. 313-322.
Wang et al., "Single-Molecule Tracing on a Fluidic Microchip for Quantitative Detection of Low-Abundance Nucleic Acids", J. Am. Chem. Soc., 2005, vol. 127, pp. 5354-5359.
Whitcombe et al., "Detection of PCR products using self-probing amplicons and fluorescence", Nat. Biotechnol., (1999), vol. 17, No. 8, pp. 804-807.
Wittwer et al., "Continuous fluorescence monitoring of rapid cycle DNA amplification", Biotechniques, (1997), vol. 22, No. 1, pp. 130-131, 134-138.
Woolley et al., "High-speed DNA genotyping using microfabricated capillary array electrophoresis chips", Anal. Chem., (1997), vol. 69, No. 11, pp. 2181-2186.
Woolley et al., "Ultra-high-speed DNA sequencing using capillary electrophoresis chips", Anal. Chem., (1995), vol. 67, No. 20, pp. 3676-3680.
Xi, "Use of Molecular Beacons to Study Mixing and Hybridization in Microfluidic Devices", $2^{nd}$ Annual International IEEE-EMBS Special Topic Conference on Microtechnologies in Medicine and Biology, (2002), Poster 203.

(56) References Cited

OTHER PUBLICATIONS

Yeung et al., "Rapid and high-throughput forensic short tandem repeat typing using a 96-lane microfabricated capillary array electrophoresis microdevice", J Forensic Sci., Jul. 2006, vol. 51, No. 4, pp. 740-747.

Yuen et al., "Microchip module for blood sample preparation and nucleic acid amplification reactions", Genome Res., (2001), vol. 11, pp. 405-412.

Zhang et al., "Miniaturized PCR chips for nucleic acid amplification and analysis: latest advances and future trends", Nuclei Acids Research, (2007), pp. 1-15.

\* cited by examiner

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 1
agggtatctg ggctctgg                                                 18

<210> SEQ ID NO 2
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 2
gcctgaaaag ctcccgatta t                                             21

<210> SEQ ID NO 3
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 3
gtcaggagat cgagaccatc cc                                            22

<210> SEQ ID NO 4
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 4
tcctgcctca gcctcccaag                                              20

<210> SEQ ID NO 5
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 5
gcccgatttt gcgactttgg agggc                                        25

<210> SEQ ID NO 6
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 6
cgcctcaaag tgctgggatt acaggcg                                      27
```

OPTICAL INSTRUMENTS AND SYSTEMS FOR FORENSIC DNA QUANTITATION

CROSS REFERENCE TO RELATED APPLICATIONS

This application is a continuation application of U.S. patent application Ser. No. 15/410,399, filed Jan. 19, 2017 and a continuation application of U.S. patent application Ser. No. 12/816,370, filed on Jun. 15, 2010, now U.S. Pat. No. 9,550,985 which claims priority and benefit under 35 U.S.C. § 119 from U.S. Provisional Patent Application Ser. No. 61/268,770, filed Jun. 15, 2009, all of which are incorporated herein by reference.

INCORPORATION-BY-REFERNCE OF SEQUENCE LISTING

The contents of the file named "54862 007C2 SeqListing.txt", which was created on Dec. 27, 2019 and is 2 KB in size, are hereby incorporated by reference in their entirety.

GOVERNMENT FUNDING

The U.S. Government has a paid-up license in this invention and the right in limited circumstances to require the patent owner to license others on reasonable terms as provided for by the terms of (Grant No. NIJ 2008-DN-BX-K009) awarded by the National Institutes of Justice, Office of Justice Programs, US Department of Justice.

FIELD OF INVENTION

Described herein are inventive methods and devices for nucleic acid quantification and, in particular, to microfluidic methods and devices for nucleic acid quantification.

BACKGROUND

Nucleic acid quantification is a critical or desirable step in a wide variety of assays and applications. For example, nucleic acid quantification is an important step in human forensic identification. For example, short tandem repeat (STR) analysis of DNA is often based on a multiplexed PCR assay, and such assays are generally most reliable within a narrowly defined range of sample DNA concentration. If too little sample DNA is used in the assay, artifacts including allele peak height imbalance and allele drop-out can occur. If too much sample DNA is used, artifacts including increased stutter, non-specific band creation, incomplete non-template addition, and pull-up peaks resulting from incomplete color separation can occur. These artifacts can lead to difficulties in interpretation of an STR profile but can be mitigated by using an appropriate amount of sample DNA. In another example, forensic casework samples have the potential to be contaminated with non-human mammalian, bacterial, or fungal DNA which, when present, contributes to the total DNA in the sample. Accordingly, for evaluation of crime scene samples, the DNA Advisory Board to the FBI recommends the use of human-specific quantification rather than total DNA quantification, which can ensure that an appropriate amount of human DNA is subjected to amplification even if bacterial, fungal, or other non-human DNA is present is the sample.

SUMMARY OF THE INVENTION

Described herein are inventive methods and devices for nucleic acid quantification and, in particular, to microfluidic methods and devices for nucleic acid quantification.

In one aspect, a method for quantifying a target nucleic acid in a sample fluid containing or suspected of containing the target nucleic acid is provided. The method comprises combining in a microfluidic channel the sample fluid and a binding agent comprising a signaling moiety, wherein the binding agent becomes immobilized with respect to the target nucleic acid, to form a test fluid, locating the test fluid in a detector region in the microfluidic channel, detecting the signaling moiety, and quantifying the target nucleic acid in the sample fluid within 1 hour of combining the sample fluid and the binding agent.

In another aspect, a method for quantifying a target nucleic acid in a sample fluid containing or suspected of containing the target nucleic acid is provided. The method comprises combining in a microfluidic channel the sample fluid and a binding agent comprising a signaling moiety, wherein the binding agent becomes immobilized with respect to the target nucleic acid, to form a test fluid, locating the test fluid in a detector region in the microfluidic channel, detecting the signaling moiety, and quantifying the target nucleic acid in the sample fluid, wherein the target nucleic acid has a concentration less than 1 nanograms per microliter or is present in a total amount in the sample fluid of less than 1 nanogram.

In still another aspect, a method for quantifying a target nucleic acid in a forensic sample fluid containing or suspected of containing the target nucleic acid is provided. The method comprises combining in a microfluidic channel the forensic sample fluid and a probe fluid containing a binding agent comprising a signaling moiety, wherein the target nucleic acid in the forensic sample fluid has not been amplified, locating the combined fluids in a detector region in the microfluidic channel, detecting the signaling moiety, and quantifying the target nucleic acid in the sample fluid.

In yet another aspect, a method for quantifying a target nucleic acid in a sample fluid containing or suspected of containing the target nucleic acid and also containing a contaminating non-human nucleic acid is provided. The method comprises combining in a microfluidic channel the sample fluid and a probe fluid containing a binding agent comprising a signaling moiety, wherein the target nucleic acid in the sample fluid has not been amplified, locating the combined fluid in a detector region in the microfluidic channel, detecting the signaling moiety, and quantifying the target nucleic acid in the sample fluid.

In still another aspect, a method for quantifying of a target nucleic acid in a sample fluid containing or suspected of containing the target nucleic acid is provided. The method comprises providing a microfluidic device coupled to an electronic device comprising a detector comprising an integrated laser, combining in a microfluidic channel of the microfluidic device the sample fluid and a binding agent comprising a signaling moiety, wherein the binding agent becomes immobilized with respect to the target nucleic acid, locating the combined fluid in a detector region in the microfluidic channel positioned in operative proximity to the detector of the electronic device, irradiating the signaling moiety using the integrated laser, and quantifying the target nucleic acid in the sample fluid.

In yet another aspect, a method for manipulating a target nucleic acid in a sample fluid containing the target nucleic acid is provided. The method comprises providing a microfluidic device comprising a plurality of microfluidic channels and active areas for sample manipulation coupled to an electronic device comprising a detector, combining in a microfluidic channel of the microfluidic device the sample fluid and a binding agent comprising a signaling moiety, wherein the binding agent becomes immobilized with respect to the target nucleic acid, locating the combined fluid in a detector region in the microfluidic channel positioned in operative proximity to the detector of the electronic device, quantifying the target nucleic acid in the sample fluid, and directing a selected quantity of the sample fluid to an active area of the biochip, wherein said selected quantity is determined, at least in part, based on the results of the quantifying step.

In still another aspect, a method for preparing a sample comprising a target nucleic acid for amplification of the target nucleic acid is provided. The method comprises providing a microfluidic device comprising at least one microfluidic channel and active areas for sample manipulation, at least one of said areas configured to purify nucleic acid from a sample, obtaining the sample by a collection method yielding an unknown variable quantity of target nucleic acid, inserting the sample into the microfluidic channel of the microfluidic device, purifying the target nucleic acid in the sample with the area of the microfluidic device configured to purify nucleic acid from a sample to produce a reproducible quantity of purified target nucleic acid, and amplifying, without quantifying the purified target nucleic acid, said reproducible quantity of purified target nucleic acid.

In yet another aspect, a method for quantifying a target nucleic acid in a forensic sample fluid containing or suspected of containing the target nucleic acid is provided. The method comprises combining in a microfluidic channel the forensic sample fluid and a probe fluid containing a molecular beacon probe comprising a signaling moiety and having unique hybridization specificity for the target nucleic acid, wherein the target nucleic acid in the forensic sample fluid has not been amplified, locating the combined fluids in a detector region in the microfluidic channel, detecting the signaling moiety, and quantifying the target nucleic acid in the sample fluid.

In still another aspect, an instrument for excitation and detection of fluorophores in a plurality of functional regions in a biochip is provided. The instrument comprises an excitation source and a steering element that directs a beam from an excitation source to a plurality of functional regions in the biochip, wherein the excitation source excites the fluorophores in the plurality of functional regions generating a signal that is detected such that said signal from at least one of the plurality of functional regions allows nucleic acid quantification.

Other advantages and novel features of the present invention will become apparent from the following detailed description of various non-limiting embodiments of the invention when considered in conjunction with the accompanying figures. Unless otherwise noted, all references cited herein are incorporated by reference in their entirety. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

BRIEF DESCRIPTION OF THE SEQUENCES

Figure 1:
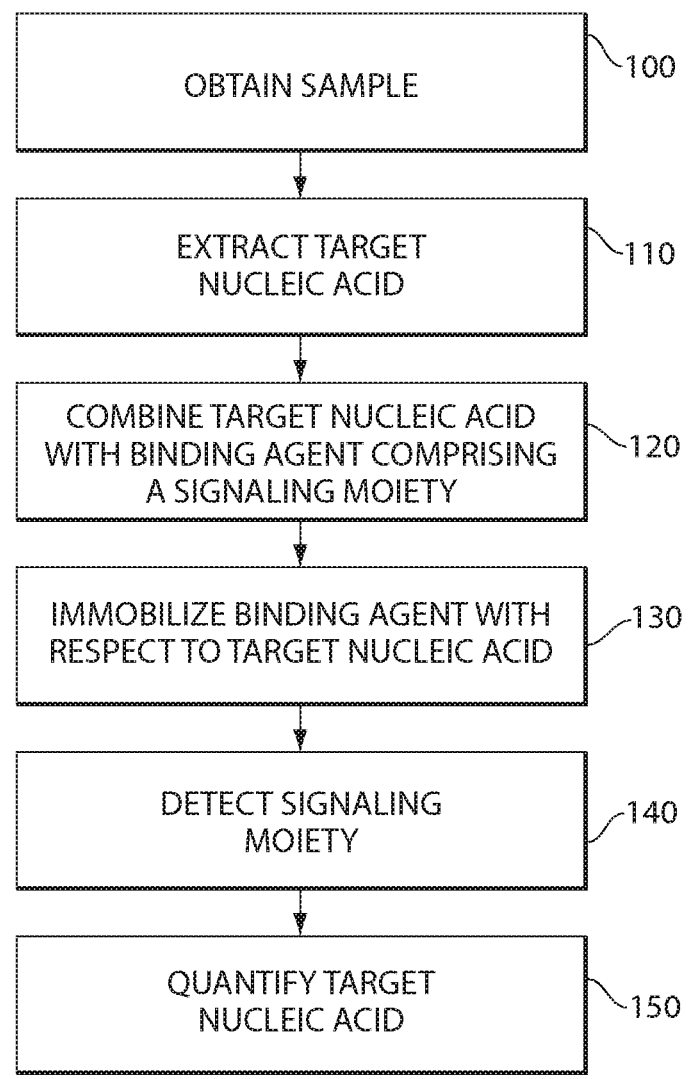
FIG. 1 shows a flowchart depicting various steps of target nucleic acid analysis, according to an embodiment.

SEQ ID NO: 1 is TH01 Forward Primer having the sequence 5'-AGG GTA TCT GGG CTC TGG-3';

SEQ ID NO: 2 is TH01 Reverse Primer having the sequence 5'-GCC TGA AAA GCT CCC GAT TAT-3';

SEQ ID NO: 3 is Alu Forward Primer having the sequence 5'-GTC AGG AGA TCG AGA CCA TCC C-3'; SEQ ID NO: 4 is Alu Reverse Primer having the sequence 5'-TCC TGC CTC AGC CTC CCA AG-3';

SEQ ID NO: 5 is PV 92 Probe 1 having the sequence 5'-GCC CGA TTT TGC GAC TTT GGA GGG C-3'; and SEQ ID NO: 6 is Alu Probe 2 having the sequence 5'-CGC CTC AAA GTG CTG GGA TTA CAG GCG-3'.

DETAILED DESCRIPTION

Described herein are inventive methods and devices for nucleic acid quantification and, in certain embodiments, to microfluidic methods and devices for nucleic acid quantification. In one aspect, embodiments are generally related to methods of quantifying a target nucleic acid, such as native (i.e. non-synthetic) nucleic acid without the need for prior amplification. The methods involve, in some embodiments, allowing a binding agent to become immobilized with respect to the target nucleic acid. In some cases, the binding agent comprises a signaling moiety that can be used to quantify the amount of target nucleic acid. In certain embodiments, the quantification can be carried out rapidly. For example, in certain embodiments, the quantification can be completed in 1 hour or less. In certain embodiments, samples containing a low amount of target nucleic acid can be quantified, in certain embodiments using a flow-through microfluidic assay. For instance, in some cases, samples containing less than 1 nanogram may be quantified. In certain embodiments, the target nucleic acid may be quantified in the presence of, non-target nucleic acids. Also provided are devices, biochips, and kits for performing methods of the inventions, or the like.

In some embodiments, the methods described herein may be particularly useful in forensic nucleic acid analysis. However, one of ordinary skill in the art would understand that the methods are not limited to forensic analysis and can be used to analyze any suitable sample containing or suspected of containing a target nucleic acid. In some embodiments, clinical and environmental samples may be analyzed. Certain embodiments of the methods described herein may provide advantages over the prior art including one or more of, and not limited to, simplified quantification of nucleic acids, facile integration with microfluidic systems, reduced reagent usage (i.e., in the amount of reagent used and/or the number of reagents used), avoidance of reagents that can require special handling and/or storage such as enzymes, dNTPs, and PCR buffers, speed of quantification, sensitivity of quantification, specificity of quantification, and improved ability to provide automation. Also advantageously, the certain embodiments of the methods described herein can be used to analyze a target nucleic acid in a sample despite its containing one or more PCR inhibitors, which can be present, for example, in clinical samples, environmental samples, forensic samples, and the like.

In some embodiments, the methods comprise combining a binding agent comprising a signaling moiety with a sample suspected of containing a nucleic acid strand containing a target sequence (i.e., a target nucleic acid) and determining whether or not there is a change in the signaling moiety's measurable characteristic as compared to that characteristic under essentially the same conditions in the absence of the target nucleic acid. In some embodiments, it may be desirable to run a control containing no target and to compare the response of the sample to the response of the control. In some cases, the level of signal may be measured for quantitative determinations. In certain such embodiments, the level of signal determined with a test sample may be compared with a calibration standard prepared using calibration samples containing known concentrations of nucleic acid strands containing the target sequence. In some embodiments, a change may simply be detected for the purpose of confirming the presence or absence of the target nucleic acid. In embodiments where a control is used, the difference in signal change between the sample and the control may be calculated.

In some embodiments, multiple nucleic acid samples can be analyzed/quantified essentially simultaneously. As discussed in more detail below, multiple nucleic acid samples may be analyzed in parallel with a microfluidic system comprising a microfluidic biochip, accompanying instrumentation, and software. In some embodiments, using a microfluidic system allows multiple samples to be processed using an essentially identical set of manipulations for each sample (or subset of samples) using a tailored set of manipulations. Furthermore, in some cases, a plurality of independent sample treatments and/or analyses can be performed in integrated fashion on a given sample. For example, a forensic sample may be analyzed by serially isolating DNA (i.e., the target nucleic acid), quantifying the isolated DNA, automatically metering a volume of DNA solution based on the quantification result, and then performing one or more of short tandem repeat (STR) analysis, single-nucleotide polymorphism (SNP) analysis, and mitochondrial sequencing on the isolated DNA. Similarly, a clinical sample may be analyzed by purifying the target nucleic acid, quantifying the target nucleic acid, automatically metering a volume of the nucleic solution based on the quantification result, and performing PCR, reverse-transcription PCR, and/or DNA sequencing on the target nucleic acid. In some embodiments, a sample may be interrogated for a one or more pathogens, cellular processes, physiologic processes, drugs, and toxins essentially simultaneously on a biochip. In some embodiments, sample analysis may be done automatically by a system.

FIG. 1 provides a flow chart depicting the various steps of target nucleic acid analysis according to certain embodiments. In some embodiments, target nucleic acid analysis begins with step 100 which involves obtaining a sample. In certain embodiments, the sample may comprise a forensic sample, such as a crime scene or evidence sample. In some cases, the target nucleic acid may be extracted from the sample as in step 110, for example, to prepare the sample for the mixing of the target nucleic acid with a binding agent comprising a signaling moiety of step 120. The steps may involve immobilizing the binding agent with respect to the target nucleic acid as in step 130 and detecting the signaling moiety as in step 140. The target nucleic acid may then be quantified as in step 150 using techniques described in more detail below. It should be understood that some methods may not include all of these steps and/or may include additional steps not illustrated. For example, in some cases the target nucleic acid may not need to be extracted, thereby obviating step 110.

In some embodiments, a sample may be obtained as in step 100. A sample may be obtained by any suitable method. For example, a buccal swab may be obtained. Generally, a buccal swab uses a collection device, for example, a small brush or cotton swab, to collect a sample of cells from the inside surface of the cheek. Alternatively, a small amount of mouthwash (i.e., saline mouthwash) may be swished in the mouth to collect the cells. In some embodiments, other methods may be used to collect a sample of blood, saliva, semen, amniotic fluid, hair, skin, or other appropriate fluid and/or tissue. The wide range of samples also includes vaginal swabs, cervical swabs, urethral swabs, rectal swabs, nasal swabs, nasopharyngeal swabs, wound swabs, biopsy specimens, marrow aspirates, and sputum aspirates. A sample, in some embodiments, may be obtained from personal items (e.g. toothbrush, razor), items touched by an individual (e.g. the rim of a drinking glass, a shirt collar, the rim of a cap, a doorknob, a window pane, or a table) stored samples (e.g. banked sperm or biopsy tissue), a corpse, a victim, a perpetrator, a suspect, a crime scene, a patient, or a relative (i.e., a blood relative). In some cases, the sample nucleic acids may be unpurified, partially purified, or purified. In some embodiments, the sample nucleic acids may be essentially free of contaminating target nucleic acid. In other embodiments, the sample may contain a mixture of target nucleic acids and non-target nucleic acids (e.g. a human DNA sample for forensic analysis may also contain canine DNA). For example, the sample may be an in vitro or an in vivo sample. Generally, a sample contains a target nucleic acid or is suspected of containing a target nucleic acid. It should be understood that "sample" may refer to the target nucleic acid, a mixture (solid and/or liquid) containing the target nucleic acid, or a material (solid and/or liquid) suspected of containing the target nucleic acid.

A sample may contain at least some target nucleic acid or may contain no target nucleic acid. In some embodiments, the quantity of target nucleic acid in the sample may be dependent on the method used to obtain the sample (i.e., the collection method). In some embodiments, the collection method may yield a quantity of target nucleic acid within a range of essentially 0 to 100 µg, within a range of 1 pg to 100 µg, within a range of 1 ng to 100 µg, within a range of 10 ng to 100 µg, within a range of 100 ng to 100 µg, within a range of 1 pg to 10 µg, within a range of 1 ng to 10 µg, within a range of 10 ng to 10 µg, or within a range of 100 ng to 10 µg. In some embodiments, the quantity of target nucleic acid collected by the collection method may differ from a first sample to a second sample by at least a factor of 10, at least a factor of 100, at least a factor of 1000, or at least a factor of 10000.

A sample may contain one or more compositions other than the target nucleic acid (if present). For example, a sample collection fluid may be used to collect, dilute, suspend, or dissolve, a sample. Generally, the sample collection fluid may be aqueous; however, the sample collection fluid may also comprise an organic solvent instead of or in addition to the aqueous solvent. In various other embodiments, the sample collection fluid may contain one or more buffers, stabilizers, enzyme inhibitors (e.g., nuclease inhibitors), chelating agents, salts, or other compositions. In another embodiment, following collection of the sample with the sample collection fluid, the sample may be allowed to dry (e.g., forensic swab samples may be dried and processed at a later time). In yet another embodiment, no sample collection fluid may be utilized (e.g., a dry swab may be used).

In some embodiments, the target nucleic acid (if present) may be extracted (e.g., purified) from the sample as in step 110. In some cases, the target nucleic acid may be extracted in a microfluidic biochip. However, one of ordinary skill in the art would recognize that the target nucleic acid may also be extracted by any of a number of extraction methods known in the art, many of which are commercially available. For example, a liquid-liquid extraction technique may be used, such as those involving phenol-chloroform solutions. In another example, a liquid-solid extraction technique may be used, where a sample is collected on a solid substrate and washed, generally with a plurality of solutions, to isolate the target nucleic acid (see, for example, kits sold by Qiagen Corporation). Other examples of nucleic acid purification may be found, for example, in U.S. patent application Ser. No. 12/699,564, entitled "Nucleic Acid Purification," filed Feb. 3, 2010, by Selden et al., which is incorporated herein by reference.

In embodiments where the target nucleic acid is isolated from a cellular sample (i.e., a cell, a plurality of cells, a mixture of cells, one or more cells within a tissue), the cell(s) may be broken open (e.g., disrupted or lysed). In some embodiments, the membrane lipids of the cell may be disrupted using a detergent. In some cases, proteins may be broken down by treating the sample with one or more proteases. In some instances, proteins may be removed by precipitation, for example, with an acetate salt such as sodium acetate or ammonium acetate. In some embodiments, proteins may be removed using phenol-chloroform phase separation. In some embodiments, the target nucleic acid may be precipitated, for example, using an alcohol such as ethanol or isopropanol. In some cases, guanidinium thiocyanate-phenol-chloroform may be used, for example, to extract an RNA or DNA target nucleic acid. A partially purified or purified target nucleic acid can be solubilized in any suitable solution (e.g. collection fluid), for example, deionized water or a buffer such as tris-EDTA (TE). Other techniques for purifying DNA and/or RNA will be known to those skilled in the art.

As discussed above, any sample containing or suspected of containing a target nucleic acid may be analyzed. The target nucleic acid may be any nucleic acid. For example, in some embodiments, the target nucleic acid may be DNA, RNA or mixtures or copolymers thereof. In some embodiments, the target nucleic acid (and other types of nucleic acids, as are described herein) may be genomic DNA, chromosomal DNA, extrachromosomal DNA, plasmid DNA, mitochondrial DNA, chloroplast DNA, cDNA, rRNA, mRNA, or fragments thereof. The target nucleic acid may be isolated from natural sources (i.e. native), recombinantly produced, or artificially synthesized. For example, the target nucleic acid may be isolated from a human cell, a bacterial cell, a fungal cell, a eukaryotic cell, a prokaryotic cell, or a virus. In some cases, the target nucleic acid may be synthetic (i.e., a product generated by amplification [e.g. PCR, quantitative PCR, reverse transcription PCR], ligation, or a chemical synthesis). The target nucleic acid may be a nucleic acid that encodes a biological entity, such as a protein, an enzyme, an antibody, a receptor, a ribozyme, a ribosome, or the like, or a portion thereof. As another non-limiting example, the target nucleic acid may be a regulatory sequence or a non-coding sequence, for instance, a small interfering RNA, a microRNA, a small hairpin RNA, or the like. In some embodiments, the target may be a unique genomic sequence or a repetitive genomic sequence. The target nucleic acid and/or the target sequence can be any number of nucleotides in length, for example, on the order of 12, 14, 16, 18, 20, 22, 25, 30, 35, 40, 45, 50, 60, 70, 80, 90, 100, 200, 400, 800, 1600, 3200, 6400 or more nucleotides in length. A nucleic acid may contain residues such as the naturally-occurring bases (e.g., adenosine or "A," thymidine or "T," guanosine or "G," cytidine or "C," or uridine or "U"), or other residues, such as methylated residues. The nucleic acid can be single-stranded in some cases to facilitate hybridization.

In some embodiments, a target nucleic acid can also be amplified using nucleic acid amplification techniques, such as PCR (polymerase chain reaction) or the like. Various copies of the target nucleic acid can be labeled with a signaling entity (e.g. a fluorescent dye). The signaling entity may be included within the nucleic acid at any suitable location, for example, at a 5' terminal site of the nucleic acid sequence, a 3' terminal site, or at an internal site within the nucleic acid.

In some embodiments, the sample may contain target nucleic acids from more than once source. For example, the sample may contain a first target nucleic acid and a second nucleic acid. In some cases, both the first target nucleic acid and the second nucleic acid may be from a first human and a second human, respectively. In some embodiments, the first target nucleic acid may be from a human and the second target nucleic acid may be from a non-human (e.g., a bacterium, a mouse, a dog, a cat, a reptile, a snake, an insect, a non-human primate, etc.). In some cases, the sample may contain two, three, four, five, six, seven, eight, nine, ten, or more distinct types of nucleic acids, one, some, or all of which may be a target nucleic acid.

In some embodiments, the sample may be combined with a binding agent as in step 120 to form a test fluid. The test fluid may be any sample fluid containing a binding agent. As discussed in more detail below, the binding agent is an entity capable of being specifically immobilized with respect to a target nucleic acid. As discussed above, in some cases, the sample may be a fluid (i.e., a sample fluid). In some embodiments, the binding agent may be contained in a fluid (hereinafter "a probe fluid"). In some embodiments, the sample fluid and/or probe fluid may be aqueous and/or organic. In some cases, the sample fluid and/or probe fluid may contain one or more buffers, stabilizers, enzyme inhibitors (e.g., nuclease inhibitors), chelating agents, salts, or other compositions.

In some embodiments, the binding agent may be attached to the microfluidic device. For example, in some instances, the binding agent may be covalently attached to the wall of a microfluidic channel. In some cases, the binding agent may be non-covalently attached to a wall or feature of a microfluidic channel. In some embodiments, the target nucleic acid may be attached to the microfluidic device (i.e., covalently or non-covalently). In some embodiments, a microfluidic channel may have a region suitable for binding a binding agent and/or a target nucleic acid. For example, the binding agent and/or target nucleic acid may be flowed through a first region of a microfluidic channel without substantially binding to a feature and bind to a feature in a second region of a microfluidic channel. In certain embodiments, neither the target nucleic acid nor the binding agent are or become attached to the wall of any microfluidic channel during the assay, but rather remain suspended in the test fluid.

In some instances, the sample fluid and the probe fluid may be combined. For example, the sample fluid and the probe fluid may be combined in a microfluidic system (e.g., in a microfluidic channel or a mixing compartment of a microfluidic channel containing system). The sample and the binding agent may be mixed using any suitable technique. For example, the sample fluid and probe fluid may be mixed by vortexing or pipetting the combined samples. In some embodiments, the sample fluid and probe fluid can be mixed in a microfluidic system. One of ordinary skill in the art will be aware of devices and channel configurations for mixing fluids in a microfluidic system, non-limiting examples of which are disclosed in International Patent Application Publication No. WO/2008/124104, entitled "Integrated Nucleic Acid Analysis," filed Apr. 4, 2008, by Tan et al., which is incorporated by reference herein.

The binding agent may be any entity capable of being immobilized with respect to a target nucleic acid comprising a target sequence. In some embodiments, the binding agent may become immobilized with respect to the target nucleic acid through non-covalent bonds. For example, the non-covalent bonds may comprise one or more of hydrogen bonds, van der Waals interactions, hydrophobic interactions, etc. In some cases, the binding agent may become immobilized with respect to the target nucleic acid through one or more covalent bonds.

In some embodiments, the binding agent may be capable of being specifically immobilized to a target sequence of a target nucleic acid (i.e., the binding agent may be a specific binding agent having unique specificity for the target nucleic acid). For example, the binding agent may be preferentially immobilized (e.g. hybridized) to a first target nucleic acid having a first sequence relative to a second target nucleic acid having a second sequence, the second sequence being different from the first sequence. In some cases, the binding agent may be capable of being immobilized non-specifically to target nucleic acid. For example, the binding agent may intercalate into a target nucleic acid substantially independently of the target nucleic acid sequence. In some embodiments, the binding agent may be an intercalating dye, an intercalating fluorescent dye, or an intercalating fluorescent dye capable of selectively intercalating with double stranded nucleic acids.

In some embodiments, the binding agent may be a nucleic acid, i.e., the binding agent may be a nucleic acid probe. One of ordinary skill in the art would recognize that a nucleic acid probe may be designed to have a sequence that can hybridize to a target nucleic acid having a sequence that is at least partially complementary to the sequence of the nucleic acid probe under a given set of annealing conditions. One of ordinary skill in the art would also recognize that the sequence homology between the target nucleic acid and the nucleic acid probe need not be perfect. For example, in some embodiments, a target nucleic acid and nucleic acid probe pair may have one or more mismatches.

In some embodiments, a binding agent (e.g., a nucleic acid probe) and a target nucleic acid may be hybridized by heating a sample containing the binding agent and target nucleic acid to a first temperature and then cooling the sample to a second temperature. In some cases, the first temperature may be held for a period of time before cooling to the second temperature. For instance, the first temperature may be held for less than 1 second, less than 5 seconds, less than 10 seconds, less than 30 seconds, less than 1 minute, or less than 5 minutes. Of course, temperatures outside these ranges may be used as well. In some embodiments, the first temperature may be above the melting temperature (i.e. temperature at which hybridized complementary strands dissociate, $T_m$) of the hybridized binding agent and target nucleic acid. In some embodiments, the first temperature may be within 5° C. of the $T_m$ of the hybridized binding agent and target nucleic acid. In some embodiments, the first temperature may be at least 30° C., at least 40° C., at least 50° C., at least 60° C., at least 70° C., at least 80° C., at least 90° C., or at least 95° C. The second temperature may be at least 5° C., at least 10° C., at least 20° C., at least 30° C., at least 40° C., at least 50° C., at least 60° C., at least 70° C., at least 80° C., at least 90° C. lower than the first temperature. In some embodiments, the rate at which the temperature is cycled between the first temperature and the second temperature may be at least 1° C./second, 5° C./second, 10° C./second, 20° C./second, 30° C./second, 50° C./second, 100° C./second, or 200° C./second. In certain cases, according to the invention, rapid thermal cycling provided by certain systems and methods of the invention can enable, at least in part, the ability to analyze, detect and/or quantify target nucleic acid more quickly than typical conventional methods. For example, in some embodiments, rapid thermal cycling may allow the concentration of a target nucleic acid in a sample fluid to be determined within a short period of time after combining the sample fluid and a binding agent.

As discussed above, the target nucleic acid may be recognized by (e.g. hybridize with) one or more binding agents. Nucleic acid binding agents can be used in various embodiments to target certain sequences within a target nucleic acid. Often, short portions of the target nucleic acid can be associated with a nucleic acid probe, for instance, a sequence of less than 50 residues, less than 30 residues, less than 20 residues, less than 15 residues, less than 10 residues, less than 9 residues, less than 8 residues, less than 7 residues, less than 6 residues, less than 5 residues, and less than 4 residues. In some embodiments, a nucleic acid probe may contain a relatively short sequence of nucleic acid residues that is able to recognize at least a portion of the target nucleic acid (i.e., the sequences are complementary, or at least substantially complementary), and often has a similar length as the recognized portion of the target nucleic acid. For instance, the nucleic acid probe may have a sequence having a length of less than 10000 nucleotides, less than 1000 nucleotides, less than 500 nucleotides, less than 250 nucleotides, less than 100 nucleotides, less than 75, 50, 40, 35, 30, 25, 24, 22, 20, 18, 16, 14, or 12 nucleotides. The selection of the structure, sequence, length, and annealing conditions for a nucleic acid probe sequence are well known in the art. The nucleic acid probes may be synthesized using any suitable technique, e.g., solid phase phosphoramidite triester methods. Other methods will be known to those skilled in the art. Nucleic acid probes may also be obtained commercially, for example, from Integrated DNA Technologies, Inc.

The nucleic acid sequences within the nucleic acid probe may be contiguous, or the sequence may be noncontiguous. For instance, there may be universal residues or gaps present within the probe sequence. Additionally, secondary structures such as hairpins, loops, etc. may be present in some cases, which may be used to create a noncontiguous sequence. As a non-limiting example, a nucleic acid probe may have a first and second region that are at least substantially complementary to a contiguous sequence of the target nucleic acid and are separated by a third region that is not complementary to the contiguous sequence of the target nucleic acid. The nucleic acid probe may hybridize to the target nucleic acid such that the third region forms a hairpin, thereby allowing the first and second regions to hybridize to the contiguous target nucleic acid sequence in a noncontiguous fashion.

In some cases, a nucleic acid probe may hybridize to a substantially complementary sequence without creating an overhang (i.e., without at least some of the residues within the nucleic acid probe extending past a terminus of the target nucleic acid). Alternatively, in some instances, a nucleic acid probe may hybridize to a target nucleic acid such that at least one residue of the nucleic acid probe extends beyond a terminus of the target nucleic acid.

A nucleic acid probe need not hybridize completely with a target nucleic acid. The hybridization of two nucleic acids and/or nucleic acid analogs can be affected by a variety of factors, and the strength of hybridization of particular residues within a given duplex can be different.

As used herein, a first sequence that is "substantially complementary" to a second sequence is one in which at least 75% of the first and second sequences are complementary (e.g., through Watson-Crick complementary pairing). For example, in a situation where a target sequence is 24 bases in length, the probe sequences would be "substantially complementary" even if they have a maximum of 6 base pair mismatch. In some embodiments, the two sequences may be at least 80%, 85%, 90%, or 100% complementary.

In certain embodiments, a nucleic acid probe may comprise at least one residue that can enhance residue stacking and/or backbone pre-organization. This can significantly increase the thermal stability (melting temperature) of the nucleic acid probe in some cases. For example, a nucleic acid probe may comprise at least one locked nucleic acid (LNA) residue. A locked nucleic acid residue is a nucleic acid analog that has a chemical shape similar to a naturally occurring nucleic acid residue (e.g., being able to form 2 or 3 hydrogen bonds with a complementary residue), but is not free to rotate in as many dimensions as a naturally occurring nucleic acid residue. For instance, in some cases, a locked nucleic acid residue may contain a 2'-O, 4'-C methylene bridge, where the methylene bridge "locks" the ribose in the 3'-endo structural conformation, which is often found in the certain form of DNA or RNA. In some cases, the locked ribose conformation may significantly increase the thermal stability of the nucleic acid probe. Other residues that can increase the thermal stability of a nucleic acid sequence will be apparent to those skilled in the art. For example, peptide nucleic acids may be used as nucleic acid probes in some cases.

In certain embodiments, the nucleic acid probe can contain a universal residue, which may be able to engage in a residue-pairing relationship with more than one natural nucleotide, and in some cases, with all of the natural nucleotides. A universal base or universal residue (e.g., "N"), as used herein, refers to a base that, when incorporated into a polymeric structure in the form of a nucleobase (e.g., a nucleotide or a PNA) does not significantly discriminate between bases on a complementary polymeric structure having nucleobases. For example, a universal base can hybridize to more than one nucleotide selected from A, T, C, and G. Universal residues will be known to those or ordinary skill in the art. Non-limiting examples of universal residues include deoxyinosine, 3-nitropyrrole, 4-nitroindole, 6-nitroindole, 5-nitroindole, 6-methyl-7-azaindole, pyrrollpyrizine, imidizopyridine, isocarbostyril, propynyl-7-azaindole, propynylisocarbostyril, allenyl-7-azaindole, 8-aza-7-deaza-2'-deoxyguanosine, 8-aza-7-deaza-2'-deoxyadenosine, 2'-deoxycytidine, 2'-deoxyuridine, 2'-deoxyadenosine, 2'-deoxyguanosine, 7-deaza-2'-deoxyinosine, 2'-aza-2'-deoxyinosine, 3'-nitroazole, 4'-nitroindole, 5'-nitroindole, 6'-nitroindole, 4-nitrobenzimidazole, nitroindazole (e.g., 5'-nitroindazole), 4-aminobenzimidazole, imidazo-4,5-dicarboxamide, 3'-nitroimidazole, imidazole-4-carboxamide, 3-(4-nitroazol-1-yl)-1,2-propanediol, and 8-aza-7-deazaadenine. Other universal residues useful for the systems and methods described herein will be known to those of skill in the art.

In some embodiments, the binding agent may comprise a signaling moiety. The signaling moiety may be any entity capable of generating a signal. In some embodiments, the signaling moiety is attached to the binding agent (i.e., through one or more covalent or non-covalent bonds). In some embodiments, the signaling moiety may not be attached to the binding agent. For example, in some cases, the signaling moiety may associate with the binding agent during or after immobilization of the binding agent with respect to the target nucleic acid. In some cases, the signaling moiety may associate with the target nucleic acid.

In some embodiments, the signaling moiety may comprise a fluorophore, fluorophore/quencher pair, chromophore, radiolabel, enzymatic substrate, colorimetric substrate, spin label, isotope such as a non-radioactive isotope or an isotope detectable by mass spectrometry (e.g., an electrophore mass label (EML)), ligand which can serve as a binding partner to a labeled antibody, enzyme, antibody which can serve as a binding partner for a labeled ligand, antigen, group having a specific reactivity, and/or electrochemically detectable moiety. In some embodiments, the signaling moiety may be a particle (e.g., a fluorescent particle, quantum dot, etc.). One of ordinary skill in the art would be able to identify other suitable signaling moieties. In some cases, the signaling moiety may generate a signal upon stimulation, for example, with light (e.g., in the case of a fluorophore or chromophore). In some instances, the signaling moiety may spontaneous generate a signal, such as in the case of a radiolabel. In certain embodiments, the ability of the signaling moiety to generate a detectable signal may be dependent on the proximity of a first component and a second component of the signaling moiety. It should be understood that the first component and second component may be connected through one or more bonds or may be not be connected (i.e., may be separable).

In some embodiments, the signaling moiety may comprise a fluorophore. Non-limiting examples of fluorophores include dyes that can be synthesized or obtained commercially (e.g. Operon Biotechnologies, Huntsville, Ala.). A large number of dyes (greater than 50) are available for application in fluorescence excitation applications. These dyes include those from the fluorescein, rhodamine AlexaFluor, Biodipy, Coumarin, and Cyanine dye families. Specific examples of fluorophores include, but are not limited to, FAM, TET, HEX, Cy3, TMR, ROX, Texas red, LC red 640, Cy5, and LC red 705. In some embodiments, dyes with emission maxima from 410 nm (e.g., Cascade Blue) to 775 run (e.g., Alexa Fluor 750) are available and can be used. Of course, one of ordinary skill in the art will recognize that dyes having emission maxima outside these ranges may be used as well. In some cases, dyes ranging between 500 nm to 700 nm have the advantage of being in the visible spectrum and can be detected using conventional photomultiplier tubes. In some embodiments, the broad range of available dyes allows selection of dye sets that have emission wavelengths that are spread across the detection range. Detection systems capable of distinguishing many dyes are known in the art.

In some embodiments, the signaling moiety may be conjugated to the binding agent. For example, a signaling moiety and nucleic acid probe may be conjugated, for example, by forming an ester bond between the 3' hydroxyl group of the nucleic acid and a linker attached to a signaling moiety. The linker may be any suitable linker. For example, the linker may be of sufficient length to allow a nucleic acid probe to hybridize to a target nucleic acid. Other techniques will be known to those of ordinary skill in the art.

In some embodiments, a quencher can be used for labeling oligo sequences to minimize background fluorescence or for use in fluorophore/quencher pairs, as described elsewhere herein. Quenchers are known to those of ordinary skill in the art. Non-limiting examples of quenchers include DDQ-I, Dabcyl, Eclipse, Iowa Black FQ, BHQ-1, QSY-7, BHQ-2, DDQ-II, Iowa Black RQ, QSY-21, and BHQ-3. In some embodiments, a quencher may have an absorption maximum within the range of 430 nm (e.g., DDQ-I) to 670 nm (e.g., BHQ-3).

In some embodiments, the binding agent comprising a signaling moiety may be a molecular beacon, for instance, as discussed in U.S. Pat. No. 5,925,517, entitled "Detectably Labeled Dual Conformation Oligonucleotide Probes, Assays and Kits," issued Jul. 20, 1999, by Tyagi et al, which is hereby incorporated by reference. The binding agent (e.g., molecular beacon) may have a target nucleic acid complement sequence flanked by members of an affinity pair, or arms, that, under assay conditions in the absence of target, interact with one another to form a stem duplex. Hybridization of the binding agent to its preselected target sequence can produce a conformational change in the binding agent, forcing the arms apart and eliminating the stem duplex. Embodiments of binding agents employ interactive labels, whereby that conformational change can be detected. In some embodiments, the binding agent may comprise at least a single-stranded nucleic acid sequence that is substantially complementary to a desired target nucleic acid, herein referred to as a "target complement sequence;" 5' and 3' regions flanking the target complement sequence that reversibly interact by means of either complementary nucleic acid sequences or by attached members of another affinity pair; and a signaling moiety comprising interactive label moieties for generating a signal. In some embodiments, the binding agent includes substantially complementary nucleic acid sequences, or "arms," that reversibly interact by hybridizing to one another under the conditions of detection when the target complement sequence is not bound to the target. In some embodiments, the binding agent comprising a signaling moiety may be unimolecular, i.e., all the above components may be in one molecule. In instances where the binding agent is bimolecular, half, or roughly half, of the target complement sequence, one member of the affinity pair and one member of the label pair may be in each molecule.

The signal generating label moieties of the signaling moiety may have interactive label "pairs" matched such that at least one label moiety can alter at least one physically measurable characteristic of another label moiety when in close proximity but not when sufficiently separated. In some embodiments, the label moieties may be conjugated to the probe such that the proximity of the label moieties to each other can be regulated by the status of the interaction of the affinity pair. In the absence of target, the label moieties may be held in close proximity to each other by the linking interaction of the affinity pair. This conformation may be referred to as the "closed" state. When the detectable signal of the signaling moiety is not generated in the closed state, which is generally the case with most embodiments, the closed state can be considered to be in the "off" state.

In instances where the target complement sequence hybridizes to its target, a conformational change may occur in the binding agent, separating the affinity pair and, consequently, the label moieties of interactive labels. This conformation may be referred to as the "open" state, which in most embodiments can be considered the "on" state. Without wishing to be bound by any theory, separation is believed to be driven by the thermodynamics of the formation of the target complement sequence-target sequence helix. Formation of the target complement sequence-target sequence helix, whether complete or nicked, overcomes the attraction of the affinity pair under assay conditions. A signal is generated because the separation of the affinity pair alters the interaction of the label moieties and a difference in at least one characteristic of at least one label moiety conjugated to the binding agent may be measured.

In some embodiments, a binding agent having interactive labels has a measurable characteristic (e.g., a detectable signal) that differs depending on whether the binding agent is open or closed. Generally, the measurable characteristic is a function of the interaction of the label moieties and the degree of interaction between those moieties that varies as a function of their separation.

As discussed above, a binding agent may have a closed conformation and an open conformation. In the closed conformation, the label moieties may be "proximate" to one another, that is, they may be sufficiently close to interact so that the signal differs (e.g., in detectable amount, quality, level, etc.) from the open conformation, when they may not interact. In some cases, it may be desirable that the difference be as large as possible. In some cases, it may be desirable that in the "off" state the measurable characteristic be a signal as close as possible to zero.

In some embodiments, the measurable characteristic (e.g., detectable signal) may be a characteristic light signal that results from stimulating at least one member of a fluorescence resonance energy transfer (FRET) pair. In some cases, the signal may be a color change that results, for example, from the action of an enzyme/suppressor pair or an enzyme/cofactor pair on a substrate to form a detectable product. In some embodiments, the binding agent comprising a signaling moiety may have a characteristic signal whose level depends on whether the label moieties are proximate due to the binding agent being in the closed position or are separated due to the binding agent being in the open position.

In some embodiments, the choice of label moieties can dictate in which state a signal is generated. In some cases, the choice of label moieties can dictate that different signals are generated in each state. In some embodiments, the interactive label moieties may be a fluorophore/quencher pair. In some instances, the interactive label moieties may be covalently conjugated to the binding agent. In some cases, the interactive label moieties may be conjugated to arm portions of the binding agent that are not complementary to the target nucleic acid. In certain instances, the signaling moiety can generate a positive fluorescent signal of a particular wavelength when the binding agent is bound to the target nucleic acid in the open state and stimulated with an appropriate light source.

As discussed above, the binding agent may be immobilized with respect to the target nucleic acid as in step 130. The immobilization may be carried out using any suitable technique. For example, in some embodiments, the binding agent and the target nucleic acid may be heated and then cooled over a period of time to facilitate immobilization (e.g., hybridization). In some embodiments, immobilization may occur without the need for a heating-cooling cycle. In some cases, a chemical reaction may be occur that immobilizes the binding agent with respect to the target nucleic acid. For example, a crosslinking reagent may be used to bond the binding agent and the target nucleic acid covalently.

The immobilization may, according to certain embodiments of the invention, be effected in a short period of time. In some embodiments, the overall time for quantifying a target nucleic acid can be significantly reduced because of the rapid immobilization time. For example, in certain embodiments, a microfluidic system including a rapid thermal cycler may be used to allow the binding agent and the target nucleic acid to achieve the desired target temperatures such that the reaction can be completed in less than 1 hour, in certain embodiments less than 30 minutes, in certain embodiments less than 20 minutes, in certain embodiments less than 10 minutes, in certain embodiments less than 5 minutes, in certain embodiments less than 1 minute, in certain embodiments less than 30 seconds, in certain embodiments less than 10 seconds, in certain embodiments less than 5 seconds, in certain embodiments less than 1 second, and in certain embodiments substantially instantaneously. Devices and methods for thermal cycling have been described, for example, in U.S. Patent Application Publication No. 2009/0023603, entitled "Methods for Rapid Multiplexed Amplification of Target Nucleic Acids," filed Apr. 4, 2008, by Selden et al., which is incorporated herein by reference.

In some embodiments, the signaling moiety may generate a detectable signal (i.e., measurable characteristic). In some embodiments, the detectable signal may be a light signal (e.g., fluorescence or chemiluminescence). As discussed above, in some embodiments, the detectable signal may be a characteristic light signal that results from stimulating at least one member of a fluorescence resonance energy transfer (FRET) pair. In some embodiments, the detectable signal may be absorbance of light having a particular wavelength or wavelength range. In some cases, the signal may be a color change that results, for example, from the action of an enzyme/suppressor pair or an enzyme/cofactor pair on a substrate to form a detectable product. In some embodiments, the detectable signal may be radiation, such as from a radiolabel. One of ordinary skill in the art would be able to identify and implement other suitable detectable signals.

In some embodiments, the target nucleic acid may be quantified as in step 150. In some embodiments, quantification may be achieved using a standard curve for target nucleic acid concentration versus detectable signal generated, for example, using the fluorescence values of a set of solutions that contained a range of known concentrations of target nucleic acid combined with a binding agent comprising a signaling moiety and plotting the fluorescence values against the known concentrations of target nucleic acid. In some embodiments, for each solution containing a known concentration of target nucleic acid, the methods as described above are performed to immobilize the binding agent with respect to the target nucleic acid, and the signaling moiety is then detected. Fitting a curve to the resultant plot, using a method such as a linear regression, can allow the derivation of a general mathematical formula for calculating the concentration of target nucleic acid in a sample having an unknown concentration of target nucleic acid by inputting the detectable signal value of the sample, after the binding agent has been immobilized with respect to the target nucleic acid, into the formula.

In another embodiment, a physical property of the signaling moiety may be used to determine the concentration of a target nucleic acid. For example, the molar absorptivity and quantum yield of a fluorescent signaling moiety at a particular wavelength may be used to determine the concentration of target nucleic acid in solution using techniques known to those skilled in the art. Generally, the fraction of target nucleic acid having binding agent immobilized thereto would be determined and factored into the quantification. The concentration of the target nucleic acid in a sample having an unknown concentration of the target nucleic acid can be determined using the molar absorptivity and quantum yield by measuring the fluorescence of the sample at the wavelength that corresponds to the molar absorptivity and quantum yield as understood by those skilled in the art.

In certain embodiments, the techniques and systems employed according to the invention for the methods described herein allow rapid analysis or quantification of a target nucleic acid. For example, a method that includes steps 120, 130, 140, and 150 may be completed within 10 seconds, within 30 seconds, within 1 minute, within 2 minutes, within 5 minutes, within 10 minutes, within 20 minutes, within 30 minutes, within 45 minutes, or within 1 hour. In some cases, a method that includes steps 120, 130, and 140 may be completed in between 10 seconds and 1 hour, between 10 seconds and 30 minutes, between 10 seconds and 5 minutes, between 10 seconds and 2 minutes, or between 10 seconds and 1 minute.

In some embodiments, analysis of a target nucleic acid may allow quantification of a small amount of target nucleic acid. For instance, the methods may be capable of quantifying less than 100 ng, less than 50 ng, less than 20 ng, less than 10 ng, less 5 ng, less than 2 ng, less than 1 ng, less than 100 pg, less than 10 pg, less than 1 pg, less than 100 fg, less than 10 fg, or less than 1 fg of target nucleic acid. In some cases, the methods may be capable of quantifying between 1 ng and 100 ng, between 10 pg and 20 ng, or between 1 fg and 5 ng of target nucleic acid. In some examples, the methods may be capable of quantifying between 1 ng/microliter and 50 ng/microliter, between 1 pg/microliter and 10 ng/microliter, or between 1 fg/microliter and 5 ng/microliter of target nucleic acid. In some embodiments, the methods may be capable of quantifying fewer than $10^5$ molecules, between $10^5$ and $10^{15}$ molecules, between $10^5$ and $10^{12}$ molecules, between $10^5$ and $10^{11}$ molecules, between $10^5$ and $10^{10}$ molecules, or between $10^5$ and $10^9$ molecules. In some embodiments, the quantification may be accomplished, even for samples containing native target nucleic acids at low concentration (e.g. certain forensic samples) without the need to amplify the target nucleic acid. Of course, analysis or quantification of target nucleic acid detection in amounts and/or concentrations outside of these ranges may be accomplished by one or ordinary skill in the art.

In certain embodiments, the target nucleic acid may be analyzed in a small volume of solution. In certain embodiments, performing the analysis in a microfluidic system may be advantageous for reducing the volume of solution for performing the analysis. In some cases, the detection may be carried out in less than 1 mL of solution, less than 100 microliters of solution, less than 10 microliters of solution, less than 1 microliter of solution, less than 100 nanoliters of solution, less than 10 nanoliters of solution, or less than 1 nanoliters of solution. In some embodiments, by using a small volume of solution, the analysis can be performed much more rapidly than when using a larger volume of solution. Thus, performing the analysis in a microfluidic system can be advantageous for quantifying a target nucleic acid within a short period of time (i.e., within 1 hour or even less as described elsewhere herein).

As discussed above, in some embodiments, it may be advantageous to perform the methods in a microfluidic system. In some, but not all embodiments, all components of the systems and methods described herein are microfluidic. Examples of suitable microfluidic systems are described in International Patent Application Publication No. WO/2008/124104, entitled "Integrated Nucleic Acid Analysis," filed Apr. 4, 2008, by Tan et al., and U.S. Patent Application Publication No. 2006/0260941, entitled "Ruggedized Apparatus for Analysis of Nucleic Acid and Proteins," filed May 19, 2005, by Tan et al., which are incorporated by reference herein. "Microfluidic," as used herein, refers channels with at least one dimension less than 1 millimeter. The term "microfluidic devices" or "biochip" generally refers to devices fabricated, for example by using semiconductor manufacturing techniques, to create structures that can manipulate tiny volumes (e.g. microliter, nanoliter or picoliter) of liquid, replacing macroscale analytical chemistry equipment with devices that could be hundreds or thousands time smaller and more efficient. For example, the channels of a biochip may have cross-sectional dimensions ranging from 127 microns×127 microns to 400 microns×400 microns and reservoirs may range from 400 microns×400 microns in cross section to 1.9 mm×1.6 mm. In some embodiments, channels and/or reservoirs may extend for distances as short as 0.5 mm to several 10 s of millimeters (e.g., greater than 20 mm, greater than 30 mm, greater than 40 mm, or greater than 50 mm).

In some embodiments, the microfluidic system may be an automated system that reduces the need for human intervention. An automated system may be advantageous for reducing the quantification time of a target nucleic acid. For example, an automated microfluidic system may be capable of performing one or more steps automatically eliminating or reducing the need for user intervention, and thus reducing the time for performing the one or more steps. Thus, automation may contribute, in some embodiments, to the ability to quantify a target nucleic acid within 1 hour or even less as described elsewhere herein.

In some embodiments, the quantification methods described herein may be performed on a target nucleic acid before performing another procedure on the sample. For example, the quantification may be performed on the target nucleic acid before a reaction on the target nucleic acid (e.g., an amplification reaction). Other examples of procedures include nucleic acid purification, nucleic acid amplification (e.g. both singleplex and multiplex end-point PCR, real-time PCR, and reverse transcription PCR), post amplification nucleic acid cleanup, nucleic acid sequencing, nucleic acid ligation, nucleic acid hybridization, SNP analyses, and electrophoretic separation. In some cases, one or more procedures may be performed on a target nucleic acid using the same microfluidic system. For example, PCR and quantification of the target nucleic acid may be performed using the same microfluidic system. In some embodiments, a procedure may be performed in an active area of microfluidic system. In some cases, a microfluidic system may contain one or more active areas. In some instances, each procedure may be performed in a separate active area. In some embodiments, an active area may be used for one or more procedures. For example, an active area may be used for mixing a sample and a binding agent and may be used for determining the sample (i.e., the active area may be both a mixing region and a detector region). In another example, at least one of the active areas of the microfluidic device may comprise an area configured to amplify nucleic acid via polymerase chain reaction (PCR). In some embodiments, an amplifying step may occur in an active area configured to amplify nucleic acid.

In some embodiments, the quantification methods described herein may provide feedback for adjusting a parameter of the sample. For example, the results of target nucleic acid quantification may indicate whether or not to dilute or concentrate the sample. The results of target nucleic acid quantification may also indicate to what extent to dilute or concentrate the sample. In some embodiments, the results of target nucleic acid quantification may be used in an automated system to allow a precise quantity of nucleic acids to be utilized for subsequent processing. In some cases, quantification may be performed multiple times on a given sample, for example, before and after other processing steps. In some cases, different volumes of the sample can be routed to different regions of the biochip to allow parallel processing of the sample following a single quantification step (e.g., based on quantification, different amounts of target nucleic acid can be metered for subsequent processing such as PCR, SNP analysis, or DNA sequencing).

In some embodiments, the biochip may comprise a plurality of microfluidic channels and active areas for sample manipulation. In some embodiments, the method may comprise a step after the quantifying step, where a selected quantity of the sample fluid may be directed to an active area of the biochip. In some embodiments, the selected quantity may be determined, at least in part, based on the results of the quantifying step.

In some embodiments, it may be desirable to control the amount of target nucleic acid subjected to a procedure such as PCR amplification. As described above, in some embodiments, control of the amount of target nucleic acid can be achieved by quantifying the target nucleic acid and then metering out the desired amount of target nucleic acid to be subjected to a procedure. However, in some embodiments, a procedure may be performed on a target nucleic acid before quantification or without quantifying the target nucleic acid. For example, in some embodiments, PCR amplification of a target nucleic acid may be performed without first quantifying the target nucleic acid. In some embodiments, the target nucleic acid may be purified from a sample to produce a reproducible quantity of purified target nucleic acid. For example, the amount of target nucleic acid can be controlled by using a "cut-off" approach. In this approach, a binding membrane may be used that can bind a target nucleic acid up to a threshold amount, above which substantially no additional target nucleic acid is bound (i.e., the binding membrane may have a defined nucleic acid binding capacity). Generally, binding of a target nucleic acid to the binding membrane comprises contacting at least a portion of the sample with the binding membrane to bind the target nucleic acid. In some embodiments, the nucleic acid binding capacity is essentially the same as the reproducible quantity of purified target nucleic acid.

In some embodiments, sample amounts can be chosen such that the range of target nucleic acid amounts contained in the samples is above the binding membrane threshold amount, such that substantially all target nucleic acid in an amount greater than the binding membrane threshold amount is not retained by the binding membrane. Thus, the amount of target nucleic acid can be controlled without quantification for a sample containing an unknown amount of target nucleic acid but containing an amount of target nucleic acid above the binding membrane threshold amount. Such an approach may be advantageous, for example, for decreasing the time needed to perform a procedure by eliminating a quantification step.

Figure 12:
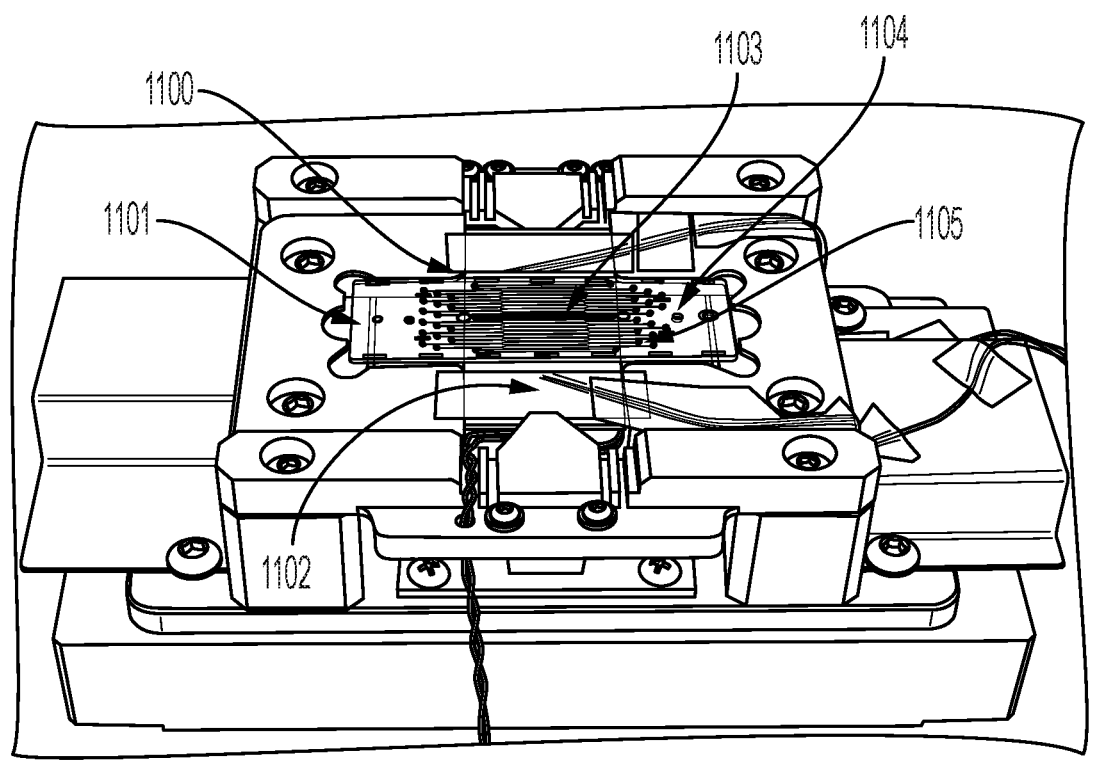
FIG. 12 shows a photograph of a view from above of a thermal cycler comprising a TCE (1100), biochip (1101), thermosensor (1102), thermoelectric cooler (1103), heat sink (1104), and heat sink thermosensor (1105), where the chip compression element has been removed for clarity, according to an embodiment.

In some cases, the binding membrane may contain one or more layers. In some embodiments, the amount of nucleic acid bound by the binding membrane (i.e., binding capacity) scales substantially linearly with the number of layers in the binding membrane. In some embodiments, the binding capacity scales with the diameter of the binding membrane. The diameter of the binding membrane may be, for example, at least 0.1 mm, at least 0.5 mm, at least 1 mm, at least 2 mm, at least 5 mm, or at least 10 mm. In some embodiments, the binding membrane may be a silica membrane capable of binding a nucleic acid. As a non-limiting example, FIG. 12 shows the binding performance of a 1 mm diameter binding membrane over a range of DNA inputs.

In some embodiments, the binding membrane threshold amount (i.e., saturation amount) may be at least 50 ng, 100 ng, at least 200 ng, at least 300 ng, at least 400 ng, at least 500 ng, at least 600 ng, at least 700 ng, at least 800 ng, or even more. In some embodiments, the binding efficiency of the binding membrane may be less than 100% such that an excess of target nucleic acid may be needed to saturate the binding membrane. For example, at least 10% more, at least 20% more, at least 50% more, at least 100% more, or at least 200% more target nucleic than the binding membrane threshold amount may be needed to saturate the binding membrane.

The target nucleic acid may be eluted from the binding membrane using any suitable method. For example, the target nucleic acid may be eluted by flowing a fluid through the binding membrane having a pH within a particular range or a salt concentration within a particular range. Other suitable methods will be known to those of ordinary skill in the art.

In some embodiments, a quantification assay can be conducted in a microfluidic biochip designed to be compatible with all the required process steps. This can be advantageous, for example, in a human forensic identification casework biochip, where a portion of the purified DNA solution may be directed to the quantification module, and the remaining DNA may be available for aliquoting, for example, for STR amplification. A central feature of the approach is that the quantification data may be utilized to define the volume to be subjected to amplification. Depending on the application, the precise volume or an approximate volume would be metered microfluidically. For example, if the elution volume of the purified DNA is 100 μL and the volume of DNA solution utilized for quantification is approximately 1 μL, the majority of the DNA will be available for STR amplification. In some embodiments in which the quantity of nucleic acids is known to be small but the precise quantity is unknown (e.g. forensic touch samples), 10% or more of the eluted DNA can be utilized for quantification.

In some embodiments, the quantification method may be performed using a microfluidic system. The microfluidic system may allow the sample containing the target nucleic acid, the binding agent, and other reagents to be flowed through the biochip. For example, a single biochip may have a region for PCR amplification, fragment separation and detection, nucleic acid sequencing, ultrafiltration, and nucleic acid quantification. In some embodiments, this multifunctional biochip may process one or more samples in parallel. In some embodiments, the sample may be flowed to one or more regions in the biochip where one or more procedures may be performed. The sample may be flowing or stationary where one or more of the procedures is performed. For example, although the sample is contained in a microfluidic device, it may not necessarily in certain embodiments be flowing when the detection is performed.

In some cases, two or more procedures may be performed on the sample in the same region. In some embodiments, the biochips described below may allow integration of target nucleic acid quantification with one or more other procedures, as noted above. Accordingly, an almost limitless number of combinations can be designed into the biochip, allowing a complex set of manipulations to be completed on the biochip. One skilled in the art will appreciate that the biochips of the invention can be designed to perform a multitude of different types of analysis with essentially limitless process complexity.

The "cross-sectional dimension" of the channel is measured perpendicular to the direction of fluid flow. Most fluid channels in components of the invention have maximum cross-sectional dimensions less than 2 mm, and in some cases, less than 1 mm. In one set of embodiments, all fluid channels containing embodiments of the invention are microfluidic or have a largest cross sectional dimension of no more than 2 mm or 1 mm. In another embodiment, the fluid channels may be formed in part by a single component (e.g. an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channel(s) containing embodiments of the invention are less than 500 microns, less than 200 microns, less than 100 microns, less than 50 microns, or less than 25 microns.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flow rate of fluid in the channel. Of course, the number of channels and the shape of the channels can be varied by any method known to those of ordinary skill in the art. In some cases, more than one channel may be used. For example, two or more channels may be used, where they are positioned inside each other, positioned adjacent to each other, positioned to intersect with each other, etc.

The microfluidic chips (i.e., biochips) of the invention can be primarily composed of plastics. Useful types of plastics include, but are not limited to: unsaturated, partially unsaturated or saturated cyclic olefin copolymers "COC," unsaturated, partially unsaturated, or saturated cyclic olefin polymers "COP," poly(methyl)methacrylate "PMMA," polycarbonate "PC," polypropylene "PP," polyethylene "PE," polyetheretherketone "PEEK," poly(dimethylsiloxane) "PDMA," and polyimide "PI." The term "poly (methyl methacrylate)" or "PMMA," as used herein, means the synthetic polymers of methyl methacrylate, including but not limited to, those sold under the tradenames Plexiglas™, Limacryl™, R-Cast™, Perspex™, Plazcryl™ Acrylex™, ACrylite™, ACrylplast™, Altuglas™, Polycast™, and Lucite™, as well as those polymers described in U.S. Pat. Nos. 5,561,208, 5,462,995, and 5,334,424, each of which are incorporated herein by reference. In some embodiments, a plastic having a glass transition temperature greater than that of the maximal temperature to be utilized in the amplification reaction may be selected. Any number of these processes and materials can be used to fabricate the biochips described herein. In some embodiments, including injection molding, hot embossing, and/or machining may be used. For example, the biochips can be prepared by injection molding of a plastic substrate, for example, a COC or COP based polymers (currently sold under the tradenames Topas™, Zeonex™ Zeonor™, and Apel™). In this fabrication methodology, an injection mold and mold insert consisting of the negative of the features to be formed may be fabricated by machining and subsequent surface polishing. Together, the mold and insert may allow the substrate layers to be fabricated and the formed substrate to comprise the channels, reaction chamber features and vias. In some embodiments, the substrate and cover layers can be diffusion bonded by the application of heat and pressure. Injection molded parts may comprise gross features (such as fluid reservoirs) and/or fine features (such as capillary valves). In some cases, it can be preferable to create fine features on one set of parts and larger features on another set, because the approaches to injection molding of these differently-sized features can vary. For large reservoirs (measuring several mm (about 1-50 mm) on a side and with depths of several mm (about 1-10 mm) and capable of accommodating up to or more than hundreds of microliters), conventional molding can be employed using machined injection molding tools. In some embodiments, the tools can be burned into steel or other metal using a graphite electrode that has been machined to be a negative of the tool. More information about materials and fabrication methods are contained in U.S. Patent Application Publication No. 2009/0023603, entitled "Methods for Rapid Multiplexed Amplification of Target Nucleic Acids," filed Apr. 4, 2008, by Selden et al., which is incorporated herein by reference.

In some embodiments, a microfluidic system may include an instrument and a microfluidic chip (i.e., a biochip), where the microfluidic chip is associated with the instrument. In various embodiments, the biochip may have a plurality of features integrated into the biochip. For example, a biochip may comprise components that facilitate sample insertion; removal of foreign matter; removal of interfering nucleic acids; concentration of cells of interest; amplification of nucleic acids; thermal cycling; mixing of fluids; detection of signaling moieties; etc. In some embodiments, a pre-processing component of the biochip may accept a sample, performs initial removal of particulates and foreign nucleic acid containing cells, and concentrate the cells of interest into a small volume. In some embodiments, a sample tube may be used that can accept a swab. The sample tube, for instance, may be filled with lysis solution to perform the lysis and extraction step. As discussed above, the swab can be placed in contact with a number of cell-containing sites, including a bloodstain, a fingerprint, water, an air filter, or a clinical site (e.g., buccal swab, wound swab, nasal swab).

In some embodiments, the biochip may include a particulate filter, a purification filter, beads, or other materials.

A variety of lysis and extraction methods can be employed as described in more detail above. In some embodiments, lysis and extraction can be performed on a sample containing $10^6$ cells or less. Depending on the application, a smaller number of starting cells can be utilized in the biochips and methods of the invention, less than $10^5$, less, than $10^4$, less than $10^3$, less than, $10^2$, less than 10, and, in cases when multi-copy sequences are to be analyzed, less than 1.

In some embodiments, nucleic acid purification can be achieved by inserting a purification medium between an input and output channel. In some cases, the purification medium can be silica fiber based and use chaotropic-salt reagents to lyse the biological sample, expose the target nucleic acid, and bind the target nucleic acid to the purification media. The lysate may then be transported via the input channel through the purification medium to bind the nucleic acids. In some embodiments, bound nucleic acid may be washed by an ethanol based buffer to remove contaminants. In some cases, this can be accomplished by flowing wash reagents via the input channel through the purification membrane. In some instances, bound nucleic acid may be then eluted from the membrane by flowing an appropriate buffer (e.g., a low salt buffer). Other solid phases will be known to those of ordinary skill in the art. Essentially, any nucleic acid purification method that is functional in a conventional setting can be adapted to the biochip.

In some embodiments, the biochip may also contain different components for integrating the functional modules. These modules involve, for example, the transport of liquids from point to point on the biochip, the control of flow rates for processes that may be flow-rate dependent, (e.g., washing steps, particle separation, and elution), the gating of fluid motion in time and space on the biochip (e.g., through the use of some form of valve), and the mixing of fluids.

A variety of methods can be used for fluid transport and controlled fluid flow. One exemplary method is positive-displacement pumping, where a plunger in contact with either the fluid or an interposing gas or fluid drives the fluid a precise distance based on the volume displaced by the plunger during the motion. An example of such a method is a syringe pump. Another exemplary method is the use of integrated elastomeric membranes that are pneumatically, magnetically, or otherwise actuated. In some embodiments, these membranes can be used as valves to contain fluids in a defined space and/or prevent premature mixing or delivery of fluids. In some cases, when used in series, these membranes can form a pump analogous to a peristaltic pump. For example, by synchronized, sequential actuation of membranes, fluid can be "pushed" from its trailing side as membranes on the leading side are opened to receive the moving fluid (and to evacuate any displaced air in the channels of the device). Yet another method for driving fluids and controlling flow rates is to apply vacuum or pressure directly on the fluids themselves, by altering the pressure at the leading, trailing, or both menisci of the fluid. Appropriate pressures (for example, in the range of 0.05-30 psi) may be applied. Flow rates also can be controlled by properly sizing the fluidic channels. Without wishing to be bound by any theory, the flow rate is proportional to the pressure differential across the fluid and the hydraulic diameter to the fourth power and inversely proportional to the length of the channel or the liquid plug and the viscosity. Other methods for fluid transport will be known to those of ordinary skill in the art.

In some embodiments, fluid gating can be achieved using a variety of active valves. In some cases, an active value can include a piezoelectric valve or a solenoid valve that, in some instances, can be directly incorporated into the chip. In some embodiments, the valve may be external to the chip but in fluid communication with ports on the main chip body. In some embodiments, passive valves, such as capillary microvalves, may be used. In some cases, microvalves can use, for example, surface energy and/or geometric features such as sharp edges to impede flow when the pressure applied to the fluid is below a critical valve.

Mixing can be accomplished in a variety of ways. In some embodiments, diffusion can be used to mix fluids, for example, by co-injecting the two fluids into a single channel or chamber. In some embodiments, mixing can be enhanced. For example, techniques such as lamination may be used, in which the fluid stream is divided and recombined one or more times. In another embodiment, chaotic advection within the flow channel can be created, for example, through the use of microstructure within the channel. In systems using active pumps and valves, mixing can be accomplished by cycling fluid between two points on the device multiple times.

Figure 2:
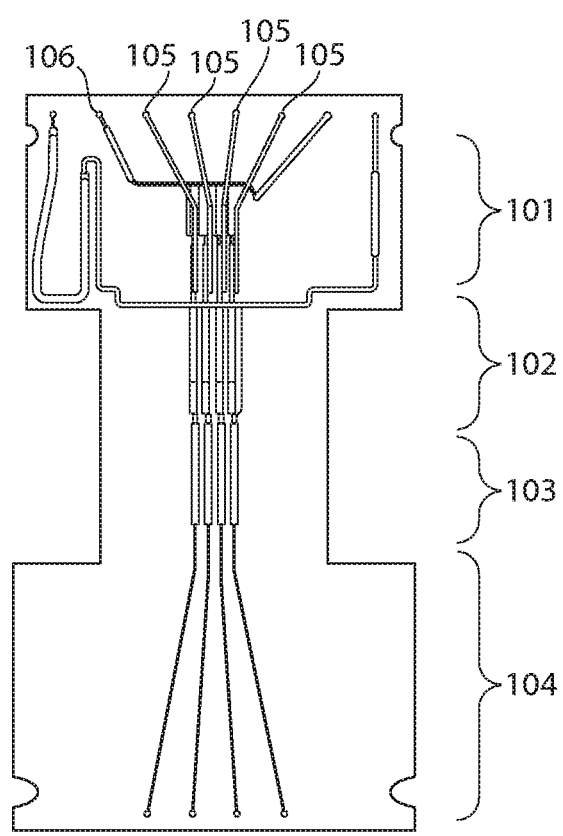
FIG. 2 shows an illustration of an exemplary integrated biochip for analyzing four individual samples, according to an embodiment.

An exemplary integrated biochip is shown in FIG. 2. The device integrates the functions of reagent distribution and metering; mixing of reagents with samples; delivery of samples to a thermal cycling portion of the chip; and thermal cycling. This exemplary biochip has several functional regions that perform PCR amplification (101), Sanger sequencing (102), and ultrafiltration (103), and quantification (104). Individual samples (containing unpurified, partially purified, or purified DNA) may be transferred to sample input ports (105). PCR reaction solution may be transferred to the biochip and mixed with samples in the four amplification reaction chambers (within 101) via pneumatic pressure on the PCR reagent reservoir and channel (106). Following thermal cycling, the amplified samples may be transported (again by pneumatic pressure) to the sequencing chambers of region 102. In some instances, sequencing reaction solution (e.g., Sanger sequencing reaction solution) may be transferred to the biochip and mixed with the four amplified samples via pneumatic pressure on the sequencing reagent reservoir and channel (107). Following cycle sequencing, the samples may be transported to region 103 for ultrafiltration. As the sequenced material is fluorescently labeled, quantification can be performed in region 104. In this case, quantification can be utilized to ensure an appropriate amount of material is loaded into a subsequent separation and detection process.

In some embodiments, following optional DNA purification, the DNA solution may be transferred to a chamber for mixing with the binding agent, and transferred to a channel, region or chamber for quantification, optionally without prior amplification. In some cases, following quantification, purified DNA would be metered for subsequent processing. In some embodiments, the samples (e.g., test fluids) may be delivered to an analysis chamber. In some embodiments, the test fluid may be located in a detector region e.g. region 104. In some cases, the test fluid may be flowing or stationary. For example, the method may comprise a locating step comprising flowing the test fluid to the detector region in the microfluidic channel. In another example, the method may comprise a locating step comprising flowing the test fluid through the detector region of the microfluidic channel during detection. The analysis chamber or detector region may, in some instances, be in thermal cycling portion of the chip. In some embodiments, the locating step may comprise maintaining the test fluid stationary at a region and moving a detector into alignment with the region to transform the region into the detector region.

As discussed above, the system may comprise a thermal cycling function. The thermal cycling function may capable of cycling between two or more temperatures. For example, the thermal cycling function may be capable of heating and cooling. In some cases, the thermal cycling function can change the temperature of a sample in the thermal cycling portion of the biochip rapidly. For example, the thermal cycling function may be capable of changing the temperature of the sample at a rate of 1° C./second, 5° C./second, 10° C./second, 20° C./second, 30° C./second, 50° C./second, 100° C./second, or 200° C./second. The thermal cycling function may also be capable of holding the temperature of the sample at a particular temperature for a period of time.

In some embodiments, the analysis chamber may be fabricated between an input and an output channel. In some cases, the system may allow a sample to be flowed through the analysis chamber. In some embodiments, the analysis chamber may be in proximity to a detection system for detecting the detectable signal of the signaling moiety in the analysis chamber. For example, in some embodiments, the analysis chamber may be in proximity to an optical excitation and detection system to allow fluorescence from the sample to be measured.

In some embodiments, the system comprises an excitation and/or detection subsystem for interacting with a sample. In some embodiments, the excitation subsystem comprises one or more excitation sources. In some embodiments, the excitation subsystem comprises an excitation beam path with optical elements including, but not limiting to, lenses, pinholes, mirrors and objectives, to condition and/or focus the excitation source in an excitation/detection window. In some embodiments, optical excitation of a sample can be accomplished by one or more lasers (e.g., a dual laser system). In some cases, the laser emission wavelength may be in the visible region, e.g., between 400 to 650 nm. For example, solid state lasers can provide emission wavelengths of approximately 460 nm, 488 nm, and 532 nm. These lasers include, for example, the Compass, Sapphire, and Verdi products from Coherent (Santa Clara, Calif.). Gas lasers can include argon-ion and helium neon with emission in the visible wavelengths at approximately 488 nm, 514 nm, 543 nm, 595 nm, and 632 nm. Other lasers with emission wavelengths in the visible region are available from CrystaLaser (Reno, Nev.). In one embodiment, a 488 nm solid state laser Sapphire 488-200 (Coherent, Santa Clara, Calif.) can be utilized. In another embodiment, a light source with wavelength beyond the visible range can be used for exciting dyes having absorption and/or emission spectra beyond the visible range (e.g., infrared or ultra-violet emitting dyes). Alternatively, optical excitation can be achieved by the use of non-laser light sources with emission wavelengths appropriate for dye excitation, including light emitting diodes, and lamps.

In some embodiments, the detection subsystem comprises one or more optical detectors, a wavelength dispersion device (which performs wavelength separation), and one or a series of optical elements including, but not limited to, lenses, pinholes, mirrors and objectives to collect emitted fluorescence from signaling entity present at the excitation/detection window. The fluorescence emitted can be from a single dye or a combination of dyes. In order to discriminate the signal to determine its contribution from the emitting dye, wavelength separation of the fluorescence can be utilized. This can be achieved, for example, by the use of dichroic mirrors and bandpass filter elements (available from numerous vendors including Chroma, Rockingham, Vt.). In this configuration, the emitted fluorescence passes through a series of dichroic mirrors where one portion of the wavelength will be reflected by the mirror to continue traveling down the path, and the other portion will pass through. A series of discrete photodetectors, each one positioned, for example, at the end of the dichroic mirror can be used to detect light over a specific range of wavelengths. In some embodiments, a bandpass filter can be positioned between the dichroic mirror and photodetector to further narrow the wavelength range prior to detection. Optical detectors that can be utilized to detect the wavelength-separated signals include photodiodes, avalanche photodiodes, photomultiplier modules, and charge-coupled device (CCD) cameras. These optical detectors are available from suppliers such as Hamamatsu (Bridgewater, N.J.).

In certain embodiments, it may be advantageous to use a single optical train for both quantification and laser induced fluorescence detection. For example, by using given optical components for two or more functions, it is possible to reduce the volume, weight, and cost of the instrument. A single optical train may comprise optical elements that couple the excitation source to the optical interrogation chambers of the quantification module and the excitation/detection window of the separation and detection module. In some embodiments, the optical train may also couple the light from the optical interrogation chambers (i.e., analysis chambers) of the quantification module and the excitation/ detection window of the separation and detection module through the wavelength separation element and to the optical detectors. In some embodiments, the optical elements include lenses, mirrors, dichroic mirrors, band pass filters, scanners, translation stages, light sources, and/or detectors.

Generally, the optical train may accomplish one or more of the following objectives. In some cases, the optical train may maximize excitation efficiency by efficiently coupling the excitation source to the optical interrogation chamber. In some cases, the optical train may maximize excitation efficiency by efficiently coupling the excitation source to the excitation/detection window of the separation and detection module. In some cases, the optical train may maximize fluorescence collection efficiency by minimizing losses between the optical interrogation chamber and the detector. In some cases, the optical train may maximize fluorescence collection efficiency by minimizing losses between the excitation/detection window and the detector. In some cases, the optical train may minimizing the number of optical elements by maximizing the number of shared elements between the excitation path and the detection paths. In some cases, the optical train may minimize number of optical components by maximizing the number of shared elements between the quantification module and the separation and detection module. In some cases, the optical train may use a single laser for excitation of the quantification module and the separation and detection module. In some cases, the optical train may use a common wavelength separation and detector module for the microfluidics quantification and microfluidic separation and detection modules. In some cases, the optical train may use commercially available components and select components that can withstand the vibration of transport and wide variations in temperature.

Figure 3:
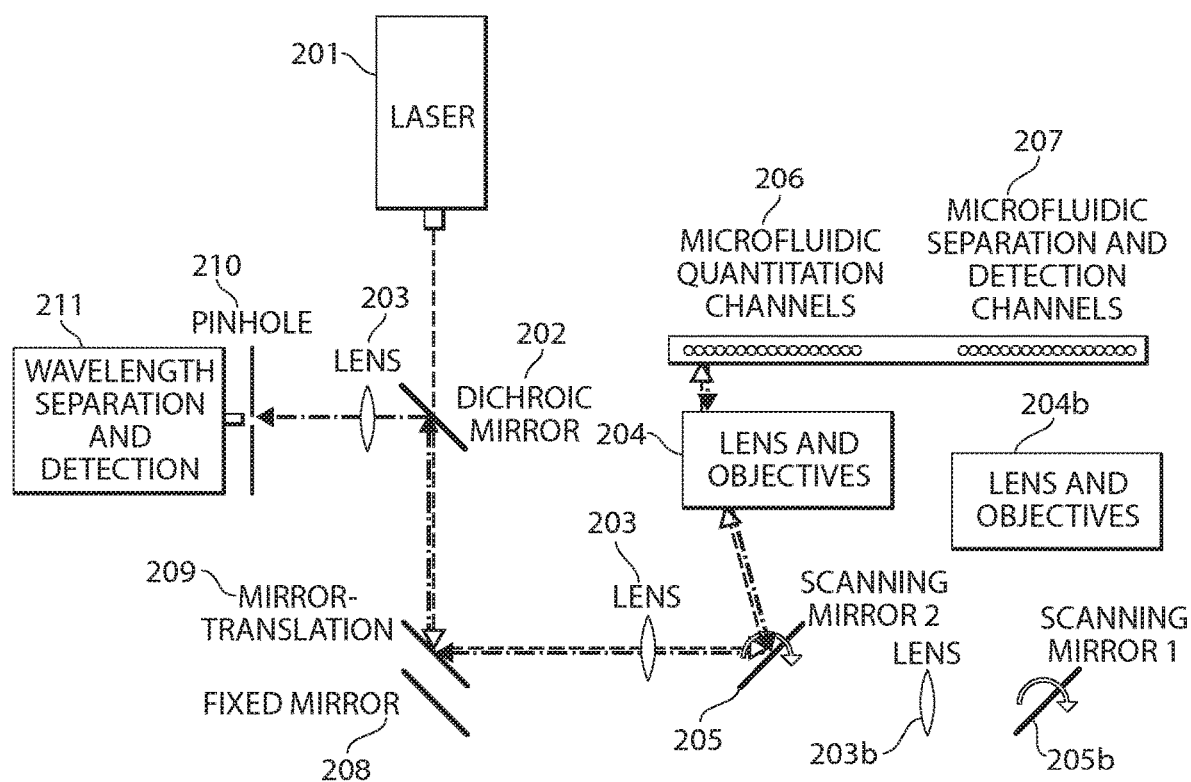
FIG. 3 shows a schematic of an optical train of a device configured to excite and interrogate interrogation chambers of a quantification module as described in Example 10, according to an embodiment.
Figure 4:
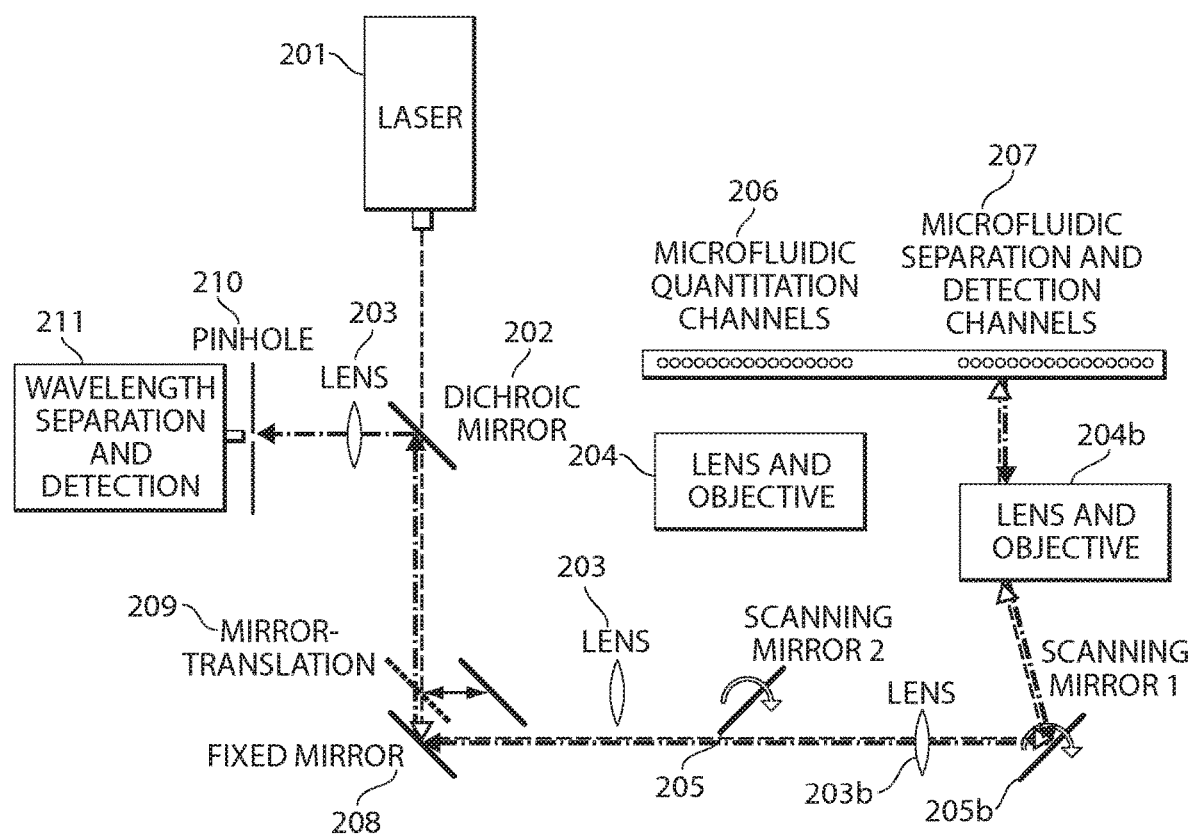
FIG. 4 shows a schematic of an optical train of a device configured to excite and detect from the detection window of a separation and detection module as described in Example 10, according to an embodiment.

FIGS. 3 and 4 show a schematic of an embodiment of an optical train configuration for both microfluidics quantification and separation and detection. The excitation path comprises a laser source (201), short pass dichroic mirror (202), a translation mirror (209), and a fixed mirror (208) pair that can allow the beam path to be directed to the quantification or the separation and detection portion of the biochip. In instances when the translation mirror (209) is in the quantification position, the excitation beam may be directed to a lens (203), a first scanning mirror (205), and a lens and objective assembly (204). The scanning mirror (205) may direct the excitation beam to each of the quantification channels (206) within the biochip. Alternatively, with the translation mirror (209) in the separation and detection position, the excitation beam may be directed to a lens (203b), a second scanning mirror (205b), and a lens and objective assembly (204b). The second scanning mirror (205b) may direct the excitation beam to each of the separation and detection channels (207) within the biochip. In this configuration, the laser source (201) is common to the quantification and separation and detection beam paths. Alternative optical excitation sources to the laser include LEDs and lamps.

The detection beam path may comprise the wavelength separation and detection element (211), a pinhole (210), and a lens (203). The detection beam path and excitation beam path may share common elements from the dichroic mirror (202) to the quantification channels (206) and from the dichroic mirror (202) to the separation and detection channels (207). The wavelength separation element may include a set of dichroic mirrors and bandpass filters to separate the wavelength components of the incoming fluorescence. These can either be discrete elements or they can be integrated in a single subassembly. Alternatively, wavelength separation can be achieved with a spectrograph or a prism. The detection elements include PMTs which can be discrete or integrated modules with multiple anodes. In this optical train configuration, the wavelength separation and detection module (211) may be common to quantification and the separation and detection modules.

In this optical train, a translation mirror (209) and fixed mirror (208) may be used to set the excitation and detection beam path for microfluidic quantification or microfluidic separation and detection. Channel to channel selection for microfluidic quantification may be achieved with the first scanning mirror (205), and channel to channel selection for microfluidic separation and detection may be achieved with a second scanning mirror (205b). The schematic of FIG. 3 shows the optical train configured to excite and interrogate the quantification chambers. The schematic of FIG. 4 shows the optical train configured to excite and detect from the separation and detection channels of the separation and detection module.

Figure 5:
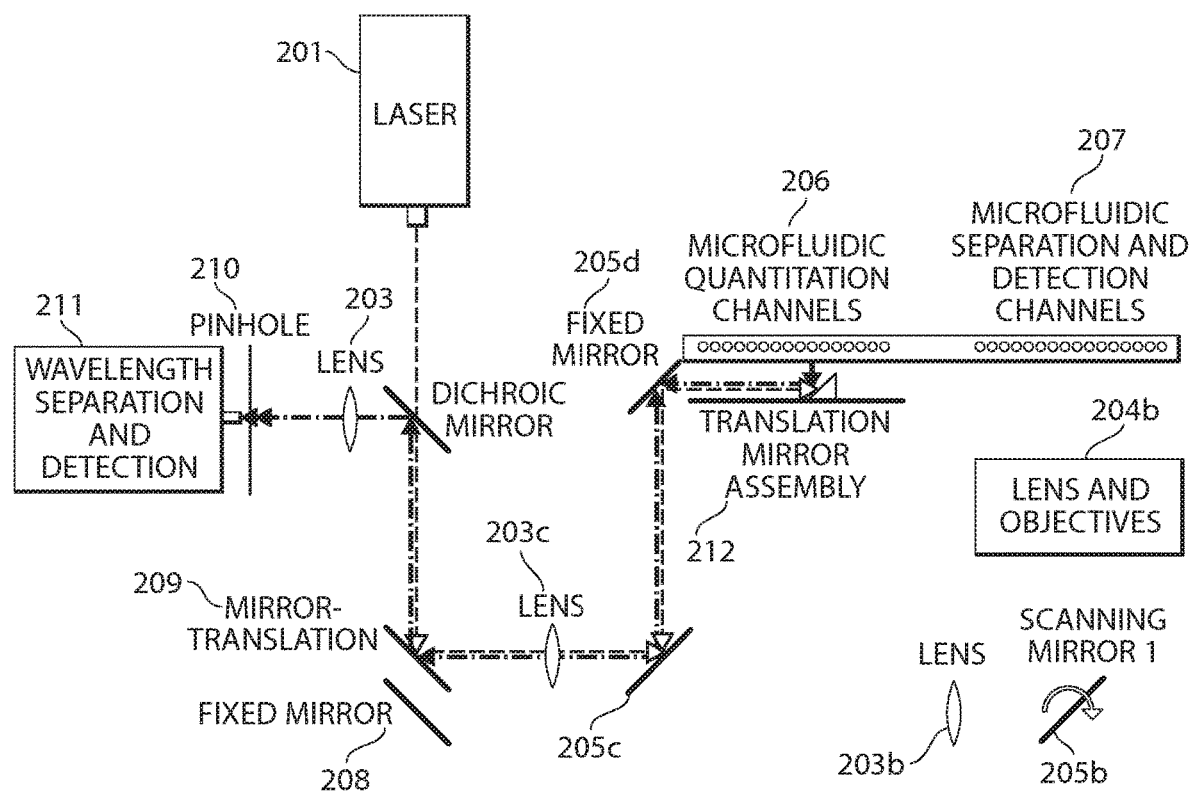
FIG. 5 shows a schematic of an alternative optical train configured to excite and interrogate the interrogation chambers of the quantification module as described in Example 10, according to an embodiment.
Figure 6:
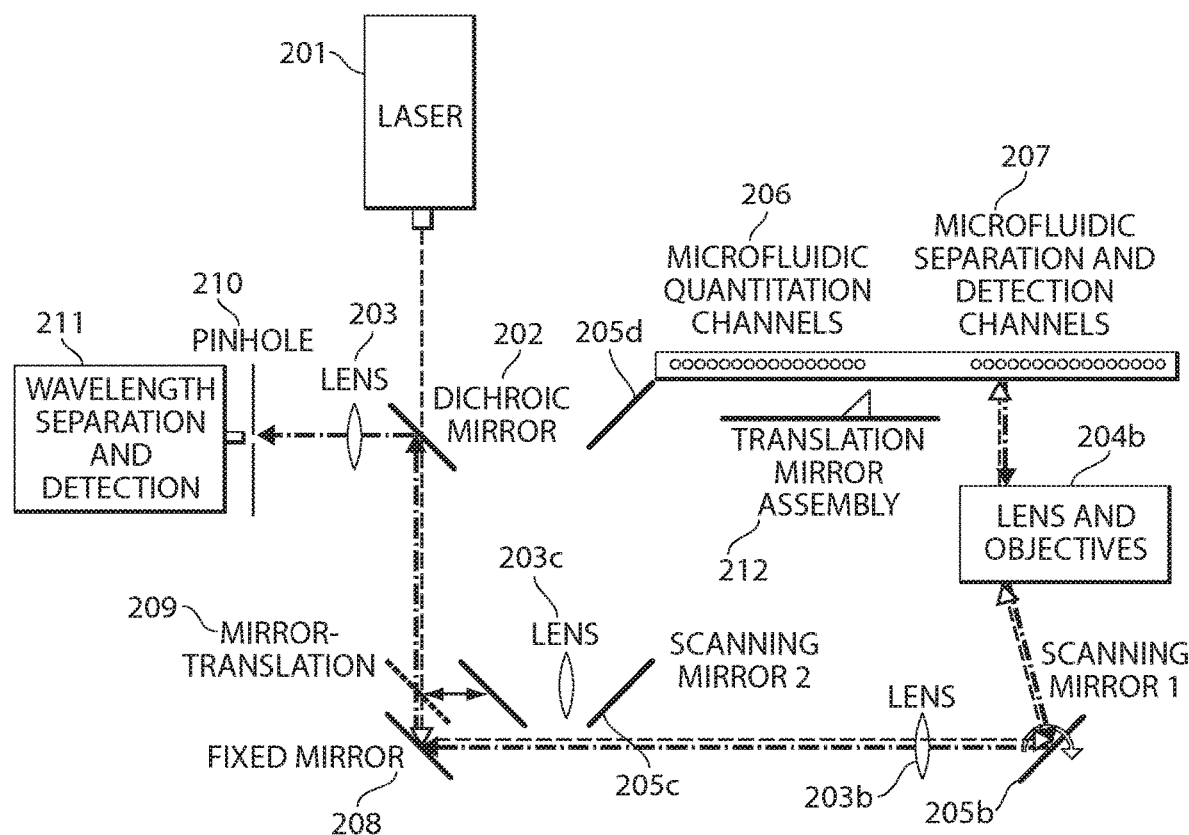
FIG. 6 shows a schematic of an alternative optical train configured to excite and detect from the detection window of the separation and detection module as described in Example 10, according to an embodiment.

FIGS. 5 and 6 show schematics of an alternate optical train that can be used for both microfluidic quantification and separation and detection. The excitation path comprises of a laser source (201), short pass dichroic mirror (202), a translation mirror (209), and a fixed mirror (208) pair that allows the beam path to be directed to the quantification or the separation and detection portion of the biochip. In instances when the translation mirror (209) is in the quantification position, the excitation beam may be directed to a lens (203c) and a first and second mirror (205c and 205d). The beam may then be directed to a translation mirror assembly (212). This assembly includes a mirror that may be mounted on a programmable translation stage. The translation mirror assembly (212) can direct the excitation beam to each of the quantification chambers (206) within the biochip. Alternatively, with the translation mirror (209) in the separation and detection position, the excitation beam may be directed to a lens (203b), a second scanning mirror (205b), and a lens and objective assembly (204b). The second scanning mirror (205b) may direct the excitation beam to each of the separation and detection chambers (207) within the biochip. In this configuration, the laser source (201) may be common to the quantification and separation and detection beam paths. Alternative optical excitation sources include LEDs and lamps.

The detection beam path comprises the wavelength separation and detection element (211), a pinhole (210), and a lens (203). The detection beam path and excitation beam path may share common elements from the dichroic mirror (202) to the quantitation channels (206) and from the dichroic mirror (202) to the separation and detection channels (207). The wavelength separation element includes a set of dichroic mirrors and bandpass filters to separate the wavelength components of the incoming fluorescence. These can either be discrete elements or they can be integrated in a single subassembly. Alternatively, wavelength separation can be achieved with a spectrograph or a prism. The detection elements include PMTs which can be discrete or integrated modules with multiple anodes. In this optical train configuration, the wavelength separation and detection module (211) may be common to quantification and the separation and detection modules.

In this optical train, a translation mirror (209) and fixed mirror (208) may be used to set the excitation and detection beam path for microfluidic quantification or microfluidic separation and detection. Channel to channel selection for microfluidic quantification may be achieved with the translation mirror assembly (212), and channel to channel selection for microfluidic separation and detection may be achieved with a scanning mirror (205b). The schematic of FIG. 5 shows the optical train configured to excite and interrogate the quantification chambers. The schematic of FIG. 6 shows the optical train configured to excite and detect from the separation and detection channels of the separation and detection module.

Figure 7:
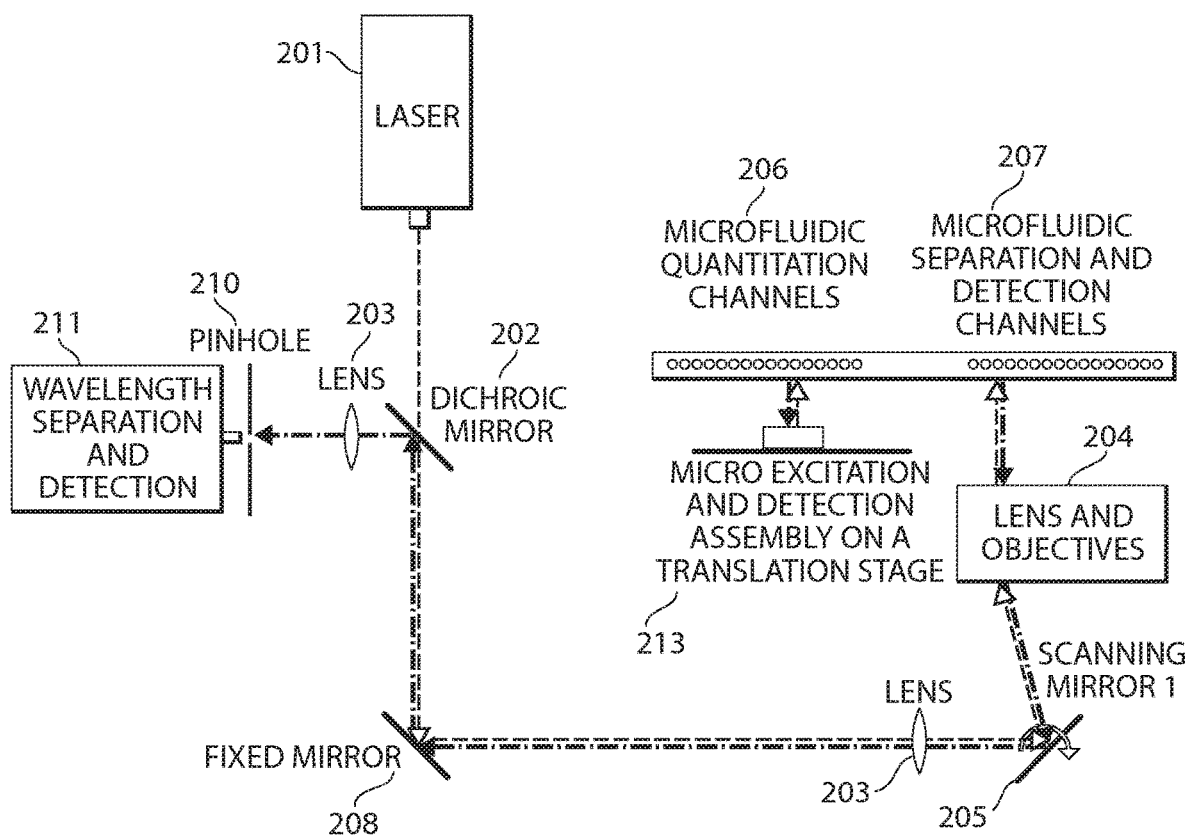
FIG. 7 shows a schematic of an alternative optical train configured to excite and detect from the detection window of a separation and detection module and interrogate the interrogation chambers of a quantification module as described in Example 10, according to an embodiment.

A third approach is the use of a miniaturized excitation source which can be a laser, LED, or lamp, a wavelength separation element, and a detector, all of which may be mounted on a translation stage (213) (FIG. 7). The translation stage can allow each of the quantification channels (206) to be interrogated. In this approach, excitation, wavelength separation and detection module for the quantification system may be independent of the separation and detection system. The optical train for separation and detection can include the elements described in FIGS. 3, 4, 5, and 6.

A fourth approach for the interrogation of the quantification channels is to simultaneously excite all the quantification chambers with a laser, LED, or lamp. Fluorescence from all the quantification chambers may be collected by a lens and passed through a diffraction element to spatially separate the wavelength components of the fluorescence. This may be then imaged onto a CCD camera or a 2-dimensional detector array. In this configuration, one axis of the detector array can correlate to channels of the quantification chambers, and the other axis of the detector array can correlate with the fluorescence wavelength. The optical train for separation and detection can include the elements described in FIGS. 3, 4, 5, and 6. In this configuration, the excitation source can be common for both the quantification and separation and detection modules.

Figure 8:
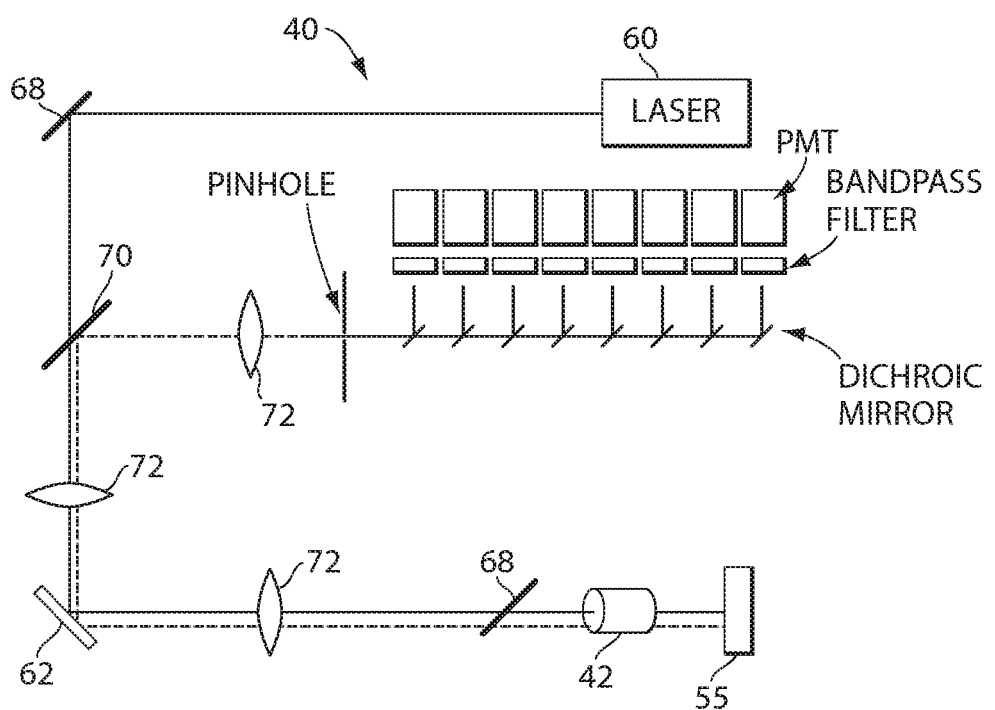
FIG. 8 shows an illustration of an exemplary excitation and detection system, according to an embodiment.

In one embodiment, wavelength components are separated by the use of dichroic mirrors and bandpass filters and these wavelength components are detected with Photomultiplier Tube (PMT) detectors (H7732-10, Hamamatsu). The dichroic mirror and bandpass components can be selected such that incident light on each of the PMTs consists of a narrow wavelength band corresponding to the emission wavelength of the fluorescent dye. The band pass may be selected to be centered about the fluorescent emission peak with a band pass of wavelength range of between 1 and 50 nm. The system may be capable of one, two, three, four, five, six, seven, or even eight color detection and can be designed with one, two, three, four, five, six, seven, or even eight PMTs and a corresponding set of dichroic mirrors and bandpass filters to divide the emitted fluorescence into eight distinct colors. More than eight dyes can be detected by applying additional dichroic mirrors, bandpass filters and PMT. FIG. 8 shows a beam path for discrete bandpass filter and dichroic filter implementation, according to one embodiment. An integrated version of this wavelength discrimination and detection configuration is the H9797R, Hamamatsu, Bridgewater, N.J.

Another method of discriminating the dyes that make up the fluorescence signal involves the use of wavelength dispersive elements and systems such as prisms, diffraction gratings, transmission gratings (available from numerous vendors including ThorLabs, Newton, N.J.; and Newport, Irvine, Calif.; and spectrographs (available from numerous vendors including Horiba Jobin-Yvon, Edison, N.J.). In this embodiment, the wavelength components of the fluorescence may be dispersed over a physical space. Detector elements placed along this physical space may detect light and allow the correlation of the physical location of the detector element with the wavelength. Exemplary detectors suitable for this function include array-based and include multi-element photodiodes, CCD cameras, back-side thinned CCD cameras, multi-anode PMT. One skilled in the art will be able to apply a combination of wavelength dispersion elements and optical detector elements to yield a system that is capable of discriminating wavelengths from the dyes used in the system.

Figure 9:
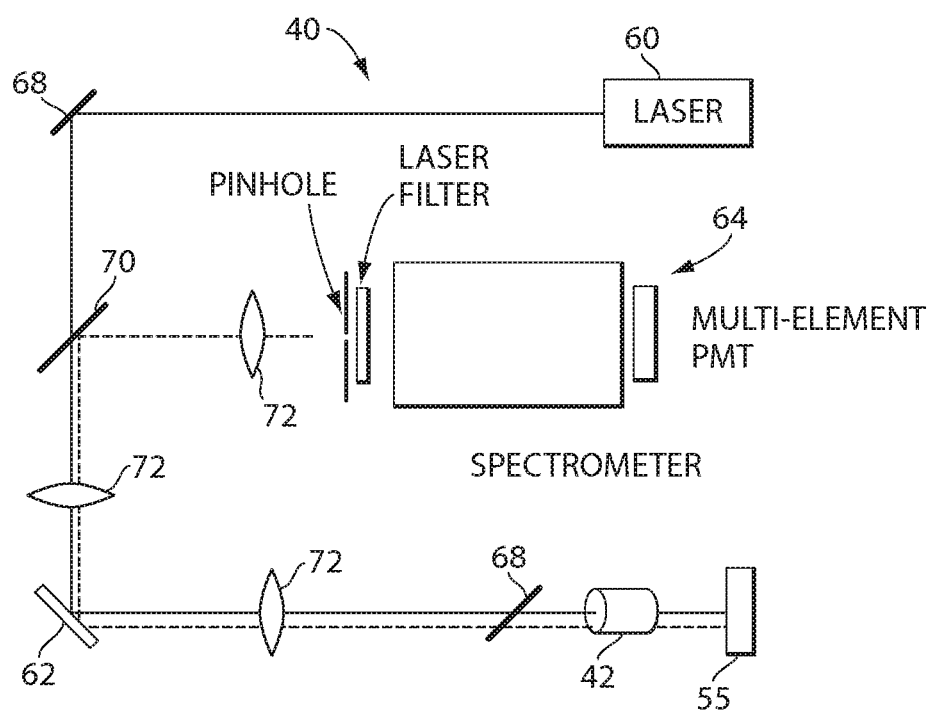
FIG. 9 shows an illustration of another exemplary excitation and detection system, according to an embodiment.

In another embodiment, a spectrograph may be used in place of the dichroic and bandpass filters to separate the wavelength components from the excited fluorescence. Details on an exemplary spectrograph design are available in John James, Spectrograph Design Fundamental. Cambridge, UK: Cambridge University Press, 2007. In some embodiments, the spectrograph P/N MF-34 with a concave holographic grating with a spectral range of 505-670 run (P/N 532.00.570) (HORIBA Jobin Yvon Inc, Edison, N.J.) may be used in this application. Detection can be accomplished with a linear 32-element PMT detector array (H7260-20, Hamamatsu, Bridgewater, N.J.). In some embodiments, collected fluorescence may be imaged on the pinhole, reflected, dispersed, and imaged by the concave holographic grating onto the linear PMT detector that is mounted at the output port of the spectrograph. In some cases, the use of a PMT-based detector takes advantage of the low dark noise, high sensitivity, high dynamic range, and rapid response characteristic of PMT detectors. In some embodiments, the use of a spectrograph and multi-element PMT detector for detection of excited fluorescence allows for flexibility in the number of dyes and the emission wavelength of dyes that can be applied within the systems and within the lane, without the need for physically reconfiguring the detection system (i.e., the dichroic mirror, bandpass, and detector) of the instrument. In some embodiments, the data collected from this configuration may be a wavelength dependent spectra across the visible wavelength range for each scan for each lane. In some cases, generating a full spectrum per scan provides dye flexibility both in terms of dye emission wavelength and number of dyes that can be present within a sample. In addition, the use of the spectrometer and linear multi-element PMT detector also can allow for extremely fast read-out rates as all the PMT elements in the array may be read-out in parallel. FIG. 9 shows the beam path for multi-element PMT and spectrograph implementation, according to one embodiment.

In some embodiments, the instrument may employ a staring mode of operation to detect multiple lanes simultaneously and/or multiple wavelengths simultaneously. In one configuration, the excitation beam may be simultaneously impinged on all lanes at the same time. In some embodiments, the fluorescence may be collected by a two dimensional detector such as a CCD camera or array. For example, one dimension of the detector may represent the physical wavelength separation, while the other dimension may represent the spatial or lane-lane separation.

For simultaneous excitation and detection of multiple samples, a scanning mirror system may be utilized to steer both the excitation and detection beam paths in order to image each of the lanes of the biochip. In this mode of operation, the scanning mirror steers the beam paths, scanning sequentially from lane to lane from the first lane to the last lane, and the repeating the process again from the first lane to the last lane again. A lane-finding algorithm may be used to identify the location of the lane.

Figure 24:
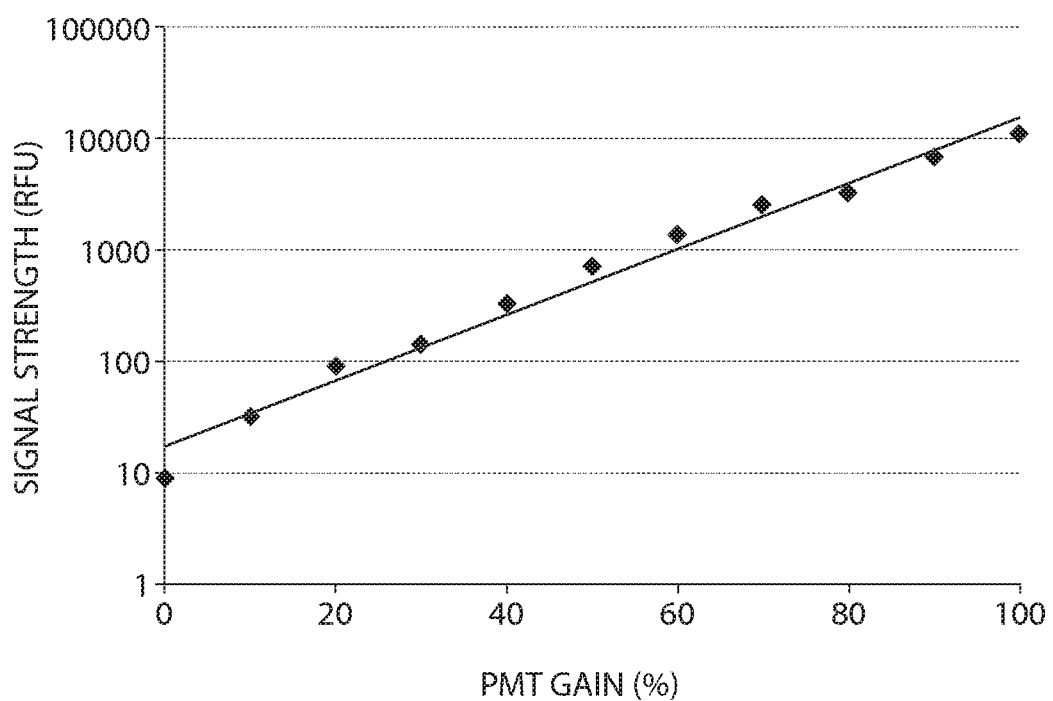
FIG. 24 shows a plot of signal strength as photomultiplier tube (PMT) gains are swept across the operation range as discussed in Example 10, according to an embodiment.

An embodiment of an optical detection system for simultaneous multiple lane and multi dye detection is shown in FIG. 24. The fluorescence excitation and detection system 40 excites the signaling moiety (e.g., the signaling moiety of a binding agent comprising a signaling moiety immobilized with respect to a target nucleic acid) by scanning an energy source (e.g., a laser beam) through a portion of each of the microchannels while collecting and transmitting the induced fluorescence from the dye to one or more light detectors for recordation, and ultimately analysis. In one embodiment, the fluorescence excitation and detection assembly 40 includes a laser 60, a scanner 62, one or more light detectors 64, and various mirrors 68, spectrograph, and lenses 72 for transmitting a laser beam emitted from the laser 60 through opening 42 to the test module 55 and back to the light detectors 64. The scanner 62 moves the incoming laser beam to various scanning positions relative to the test module 55. Specifically, the scanner 62 moves the laser beam to a pertinent portion of each micro channel within the test module 55 to detect respective separate components. The multi element PMT 64 (i.e., the light detector) collects data (e.g. the fluorescent signals from DNA fragments of varying length) from the test module 55 and provides the data electronically through a cable to a data acquisition and storage system (not shown). In one embodiment, the data acquisition and storage system can include a ruggedized computer available from Option Industrial Computers (13 audreuil-Dorion, Quebec, Canada).

In some embodiments, a signal processing algorithm may be used to correct, filter, and/or analyze the data. This process may comprise steps such as locating a callable signal, correcting the signal baseline, filtering out noise, removing color cross-talk, and/or identifying signal peaks. For example, locating the callable signal may be performed by employing a threshold. This procedure may be used to remove extraneous data from the beginning and end of the signal. In some embodiments, the background may be removed from the signal, for example, so that the signal may have a common baseline for all detected colors. In some cases, a lowpass filter may be applied to remove high frequency noise from the signal.

In one embodiment, a kit may be provided, containing one or more of the above compositions. A "kit," as used herein, typically defines a package or an assembly including one or more of the compositions of the invention, and/or other compositions associated with the invention, for example, as previously described. Each of the compositions of the kit may be provided in liquid form (e.g., in solution), in solid form (e.g., a dried powder), etc. A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In this description terms such as "target nucleic acid", "oligonucleotide," "binding agent," "nucleic acid," "strand," and other like terms in the singular. One of ordinary skill in the art will understand that many terms used to describe molecules may be used in the singular and refer to either a single molecule or to a multitude. For example, although a target nucleic acid may be detected by a binding agent in an assay, an assay may require many copies of binding agent and many copies of target nucleic acid. In such instances, terms are to be understood in context. Such terms are not to be limited to meaning either a single molecule or multiple molecules.

The following examples are intended to illustrate certain embodiments of the present invention, but do not exemplify the full scope of the invention.

Example 1

This example describes the system used in the examples below.

The system comprises an instrument for separation and detection of labeled DNA fragments and is described in more detail in U.S. Patent Application Publication No. 2009/0023603, entitled "Methods for Rapid Multiplexed Amplification of Target Nucleic Acids," filed Apr. 4, 2008, by Selden et al., which is incorporated herein by reference. The instrument is ruggedized for field and laboratory use, has low power consumption, and is CE marked under the Low Voltage Directive 73/23/EEC. DNA separation takes place within a 16 sample biochip and custom sieving matrix by applying appropriate loading, pullback, and separation voltages through a high voltage subsystem. A laser induced fluorescence detection subsystem excites and collects fluorescence from the labeled DNA fragments that pass through the excitation and detection zone of the biochip. Separations carried out by applying a 150 V/cm and 300 V/cm electric field along the separation channel are completed in 28 and 15 minutes respectively providing fast separations with better than single base pair resolution and detecting the product of PCR amplifications of single copy targets.

System Configuration.

The subsystems (pneumatic, thermal cycling, and separation and detection subsystems) are controlled by a rack mounted ruggedized industrial computer. This computer has the functionality of a full-sized desktop computer and includes a 17 inch LCD display, a full sized keyboard, and mouse.

Fluid Manipulation Instrumentation.

Figure 10:
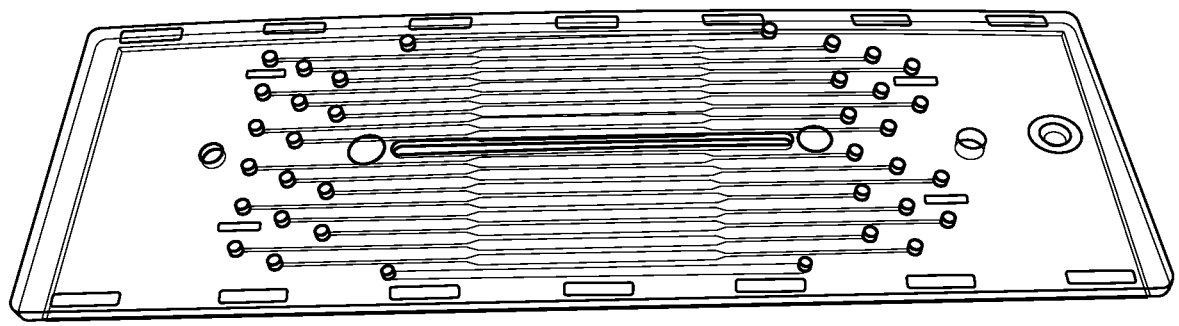
FIG. 10 shows a photograph of a biochip, according to an embodiment.

Fluid flow through biochips is effected by systematic application of pressures to ports located at the ends of fluidic channels. When a pressure less than the burst pressure of a capillary valve is applied, fluids will flow along the channel and stop at the capillary valve. Fluids will flow through the valve when a pressure greater than the burst pressure of the valve is applied. A pneumatic system is also used to close membrane valves by applying a pressure to push a membrane against a valve seat. The sealing pressure of the membrane valve is a function of the applied sealing pressure. Pressures are generated by miniature diaphragm pumps and pressure regulators to provide five discrete pressure levels which are selected and applied to the output. The system provides eight outputs which are connected to the manifold through ports on the biochip. The pneumatic subsystem is computer controlled to achieve the desired flow control. The pneumatic subsystem through systematic application of specific pressure levels to the biochip effects fluid flow to carry out the lysis and PCR within the biochip. FIG. 10 shows an exemplary photograph of a biochip.

Thermal Cycler Subsystem.

Figure 11:
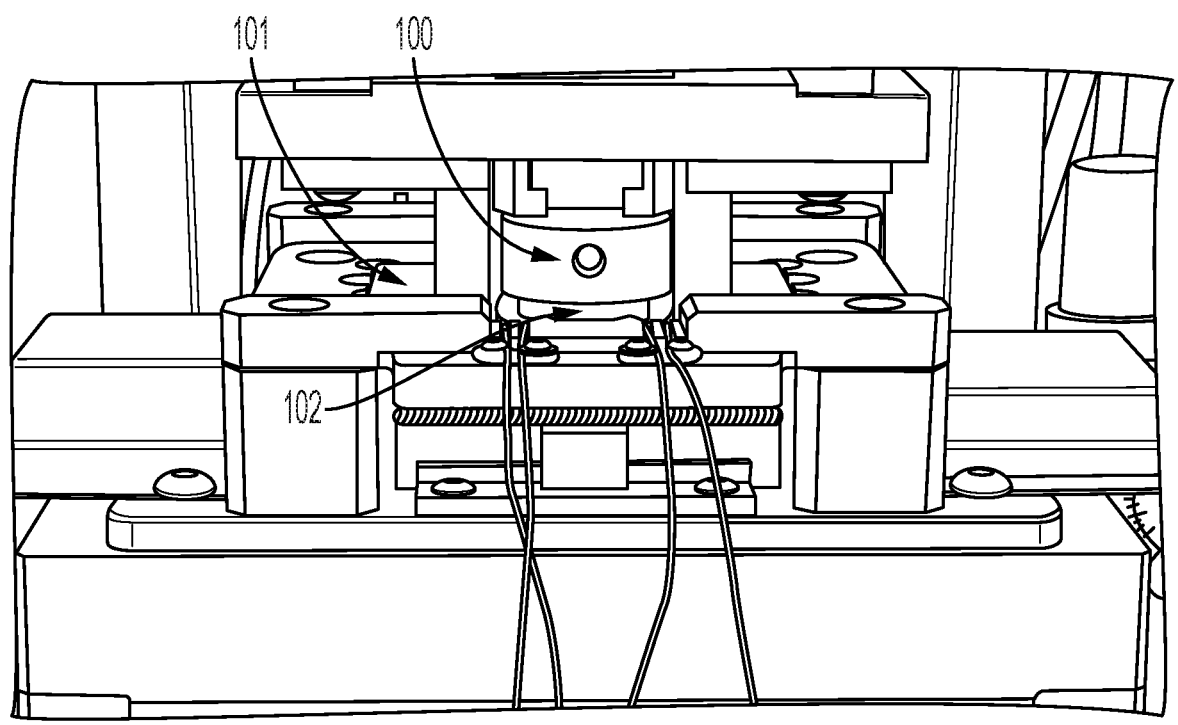
FIG. 11 shows a photograph of a thermal cycler comprising a chip compression element and thermal control element (100), biochip (101), and thermosensor (102), according to an embodiment.

The thermal cycler comprises a high output thermoelectric module (TEM) mounted on a high efficiency heat sink and fan assembly (heat pump). A cover clamps down on the biochip to provide compression and efficient thermal transfer between the TEM and the reaction chamber. Thermal losses to the cover are minimized by a layer of insulation between the biochip and cover assembly. Temperature sensors at surface of the TEM and within a reaction chamber provide feedback to allow rapid ramping to and stability at the desired setpoint temperature. The measured heating and cooling rates at the TEM surface are 21.6° C./sec and 21.7° C./sec, and the measured heating and cooling rates of the reaction solution are 14.8° C./sec and 15.4° C./sec. Reaction solutions are heated and cooled 7-fold faster in this thermal cycler compared to that in a fast commercial cycler. Minimal transition times between states allow for rapid and controlled heating and cooling of reaction solutions within the biochip. FIGS. 11 and 12 show exemplary photographs of a thermal cycler.

The existing TEM, heatsink, and fan assembly described above has been designed to mount directly to the chip chamber and positioned to center the PCR chambers on the TEM. The surface of the TEM is positioned to maximize contact with and minimize stress on the biochip. Thermocouple sensors mounted on the surface of the TEM are accommodated by designing the biochip to allow mounting pockets for the sensors. Thermal isolation between the TEM and the rest of the chip chamber is achieved with thermal breaks to minimize non-uniformity in heating and also maximize thermal response. The compression cover is modified to accommodate the format of the purification module and biochip and is utilized to generate the desired pressure for efficient thermal transfer between the TEM and reaction chambers. Thermal isolation between the reaction chamber and cover is accomplished by fabricating an air pocket above the reaction chambers. Ramping and performance of the thermal cycler is characterized by placing a thermocouple within the 16 PCR reaction chambers of the biochip.

Separation end Detection Subsystem.

The high voltage connections are mounted to the cover of the instrument and make contact to the biochip when the cover is closed. The laser induced fluorescence subsystem is integrated into the instrument with no modification to the optical beam path or subsystem components. The heater subsystem is mounted within the chip chamber.

System Status.

The thermal cycling subsystem provides the user with device status including cycle number, remaining process time, and current block and solution temperatures. User feedback is provided via the keyboard. All run data is stored on the control computer and also transferred by Ethernet to a process database. During separation and detection on the instrument, the control computer indicates the step being executed. In addition, real-time electropherograms for each of the 16 lanes and process parameters including separation channel current and substrate temperature are displayed. The onboard computer alerts the user to the time remaining until annual maintenance, the result of system power-on self test (POST), and the name of any subsystem that has failed or requires immediate maintenance.

Example 2

This example demonstrates DNA quantification by microfluidic Picogreen assay using a TH01 locus probe.

An injection molded 16-lane biochip with optically clear reaction chambers was fabricated to allow interrogation of the reaction products with the optical system described above. Each lane in the biochip holds approximately 7 μL reaction mix and allows amplification of 16 individual samples simultaneously. PCR conditions were carried out as previously described (Giese et al., "Fast Multiplexed PCR for Conventional and Microfluidic STR Analysis." (2009) J. Forensic Sci. Vol. 54, Issue 6, pages 1287-1296). The primer pairs used to target the single-copy human tyrosine hydroxylase gene, TH01 (Swango et al., "Developmental validation of a multiplex qPCR assay for assessing the quantity and quality of nuclear DNA in forensic samples." (2007) Forensic. Sci. Int. Vol. 170, Issue 1, pages 35-45), were:

```
TH01 Forward Primer:
                                    (SEQ ID NO: 1)
5'-AGG GTA TCT GGG CTC TGG-3'

TH01 Reverse Primer:
                                    (SEQ ID NO: 2)
5'-GCC TGA AAA GCT CCC GAT TAT-3'
```

Stock 10 ng/μL of 9947A genomic DNA (MCLab, South San Francisco, Calif.) was used to generate a standard curve by adding appropriate quantities of DNA in 4 μL volumes to the reaction mix. This standard curve contained 7 different concentrations of genomic DNA—0 ng, 0.4 ng, 1 ng, 4 ng, 10 ng, 20 ng and 40 ng—to use for data fitting of unknown (human and nonhuman) genomic DNA samples. Standard curve samples were analyzed in quadruplicate. Amplification was initiated with 20 seconds activation at 93° C. followed by 28 cycles of [93° C. for 4 seconds, 58° C. for 15 seconds, 70° C. for 7 seconds] and final extension for 90 seconds at 70° C. Completion time was approximately 17 minutes.

Following amplification, Picogreen Reagent® (Invitrogen) was diluted 1:200 in TE-4 (10 mM Tris pH 8, 0.01 mm EDTA) buffer and 9 μL of reagent was is added to 1 μL of PCR product. The resulting solution was incubated for 5 minutes at room temperature, protected from light. From the 10 μL sample, approximately 6 μL was loaded into a lane of a separation and detection biochip for instrument laser detection. The instrument laser was set to appropriate laser power, gain and integration time to avoid photobleaching of the dye. The laser was set to output 20 mW and an OD2 neutral density filter (Thorlabs, Newton, N.J.) was used to attenuate the output power to 0.2 mW. The gain of blue PMT was set to 30% of full scale, gain of red, yellow, and green set to 0, and the refresh rate set to 5 Hz.

Figure 13:
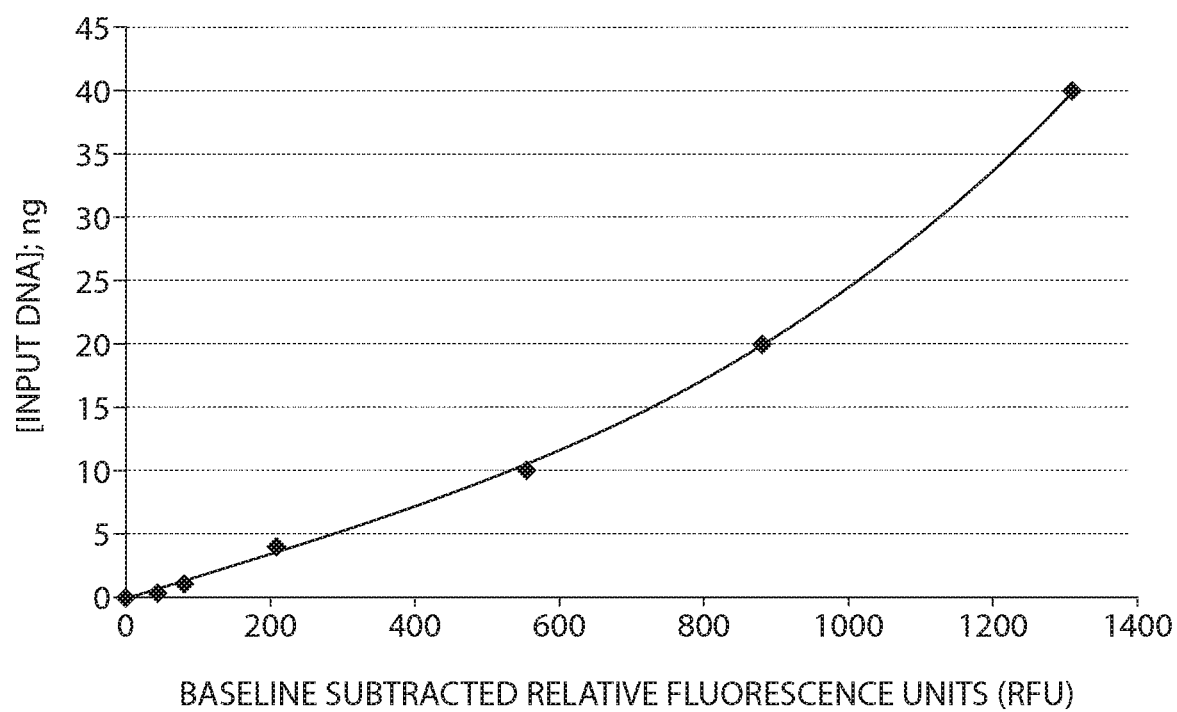
FIG. 13 shows a plot of input DNA (ng) versus baseline subtracted fluorescence signal (RFU) for a 28-cycle TH01 PCR-Picogreen reaction, according to an embodiment.
Figure 14:
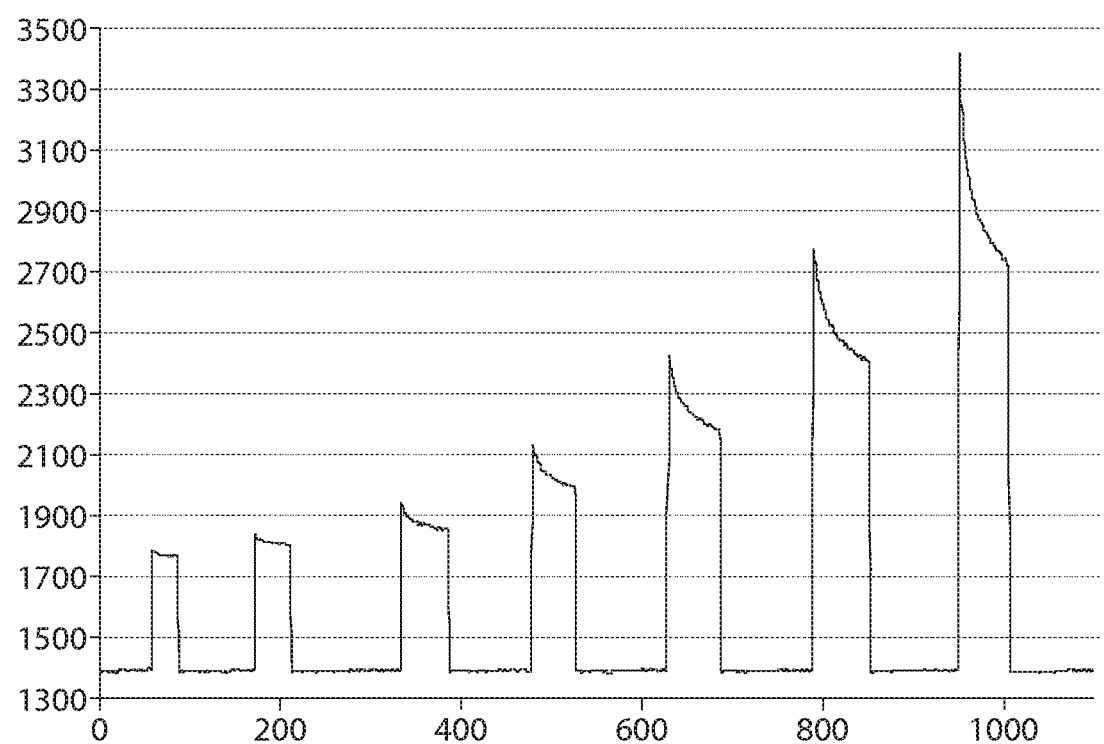
FIG. 14 shows a raw data plot of the output fluorescence signal from TH01 PCR laser detection-peak intensities from left to right correspond to 0 ng, 0.4 ng, 1 ng, 4 ng, 10 ng, 20 ng and 40 ng input template DNA, according to an embodiment.

Samples were assayed in quadruplicates. When the laser shutter is opened, the signal will increase to a maximum and then start to decrease. The fluorescence signal strength 1 second (of 5 readings) from the maximum signal was recorded. An increase in fluorescence signal was observed with increasing input DNA. A plot of input DNA versus relative fluorescence units (RFU) from the instrument has $R^2=0.999$ and was used as standard curve for extrapolating unknown DNA samples (FIG. 13). FIG. 14 is the output RFU data from laser detection as a function of lane displacement.

Genomic DNAs purified from canine buccal swabs, bacteria (*Bacillus cereus*), yeast (*Saccharomyces cerevisiae*), human buccal swabs and human whole blood were used to evaluate the assay. Bacterial DNA was extracted from bacterial cells or pellets. Canine (*Canis familiaris*) DNA was extracted from buccal swabs. Genomic yeast DNA was obtained from ATCC (Manassas, Va.). Fresh human whole blood samples containing EDTA as anticoagulant were obtained on ice from Research Blood Components, L.L.C. (Brighton, Mass.). Human buccal swab samples were obtained by moving cotton swabs (Bode SecurSwab™) up and down several times on the inside buccal surface of human subjects. Canine buccal swab samples were obtained similarly. All DNA purifications were performed using guanidinium-based lysis reagents and purification via silica-DNA binding spin columns.

Concentrations of these DNA samples were assessed by extrapolating the RFU values from the standard curve generated at the time of the experiment. DNA concentrations were also measured by UV absorbance using a Nanodrop spectrophotometer (Thermo Scientific, Wilmington, Del.). Values reported in Table 1 are average values+/− one standard deviation.

TABLE 1

| DNA Samples Tested | DNA amount (ng) | |
|---|---|---|
| | Absorbance | Microfluidic Picogreen |
| Non-human Samples Only | | |
| Bacillus cereus | 9.5 +/− 0.7 | None detected |
| Saccharomyces cerevisiae | 16 +/− 1 | None detected |
| Canis familiaris | 9.5 +/− 0.7 | None detected |
| Non-human Samples Spiked with 10 ng Human DNA | | |
| 10 ng Bacillus cereus 10 ng Human DNA | 19.5 +/− 0.7 | 11 +/− 1 |
| 16 ng Saccharomyces cerevisiae 10 ng Human DNA | 26 +/− 1 | 11 +/− 2 |
| 10 ng Canis familiaris + 10 ng Human DNA | 19.5 +/− 0.7 | 6 +/− 1 |
| Mock Casework DNA Samples | | |
| Human Child Buccal Swab DNA | 10.2 +/− 0.3 | 12 +/− 3 |
| Human Adult Buccal Swab DNA | 9.5 +/− 0.7 | 12 +/− 2 |
| Human Adult Whole Blood DNA | 39 +/− 1 | 38 +/− 4 |

Non-human DNA samples generated only background fluorescence signals in the Picogreen assay but could be detected by UV absorbance. In contrast, known quantities of human genomic DNA spiked with non-human DNA generated signals that corresponded to the human DNA contribution. Values obtained from absorbance at 260 nm for human DNA sources were close to values from Picogreen curve data fitting. Not only did output fluorescence signal increase in the presence of higher human genomic DNA template but also, data demonstrated human specificity of the TH01 primers.

The advantages of the approach over conventional assays (e.g., BodeQuant; The Bode Technology Group, Inc., Lorton, Va.) include a substantial reduction in both sample volume and amplification time. For example, amplification following the BodeQuant protocol requires 25 µL of reaction mixture and greater than 60 minutes for a 10-cycle profile. For fluorescence detection, BodeQuant uses a 96-well assay with 200 µL reaction volume per well on a plate reader. Furthermore, platereader-based assays can be quite difficult to integrate in a microfluidic biochip format. In contrast, the microfluidic assay described here used 7 µL, and the 28-cycle amplification was completed in 17 minutes. The incorporation of the OD2 neutral density optical filter reduces laser power by 100-fold, indicating that the number of amplification cycles and total process time can be reduced significantly.

With laser detection and the OD2 optical filter in place, only approximately 0.353 nl of the 10 µl Picogreen reaction solution was actually excited and detected based on the laser excitation beam diameter of 30 µm and a 0.5 mm chamber depth. Accordingly, in this configuration, the limit of detection (LOD) of the system is 0.005 picogram of DNA. The combination of microfluidic volumes and laser detection led to a powerful assay. If the OD2 filter is not utilized, the LOD is 0.05 femtograms. Chamber dimensions can be selected to allow an even smaller LOD if desired.

Example 3

This example demonstrates DNA quantification by microfluidic picogreen assay using an Alu locus probe.

The use of a repetitive locus for quantification may allow further reduction in reaction time and improvement in LOD. Human Alu sequences are repetitive elements that are present in hundreds of thousands of copies in the genome, and a primer pair targeting Alu sequences was used for microfluidic quantification:

```
Alu Forward Primer:
                                       (SEQ ID NO: 3)
5'-GTC AGG AGA TCG AGA CCA TCC C-3'

Alu Reverse Primer:
                                       (SEQ ID NO: 4)
5'-TCC TGC CTC AGC CTC CCA AG-3'
```

Figure 15:
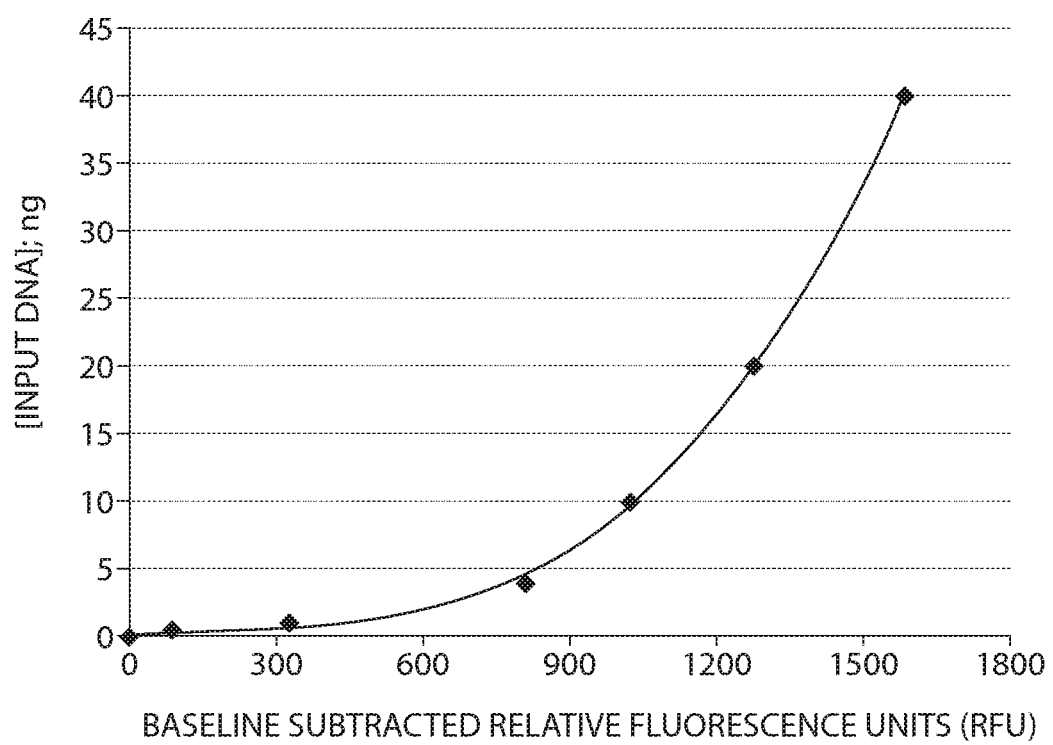
FIG. 15 shows a plot of input DNA (ng) versus baseline subtracted fluorescence signal (RFU) for a 15-cycle Alu PCR-Picogreen reaction, according to an embodiment.
Figure 16:
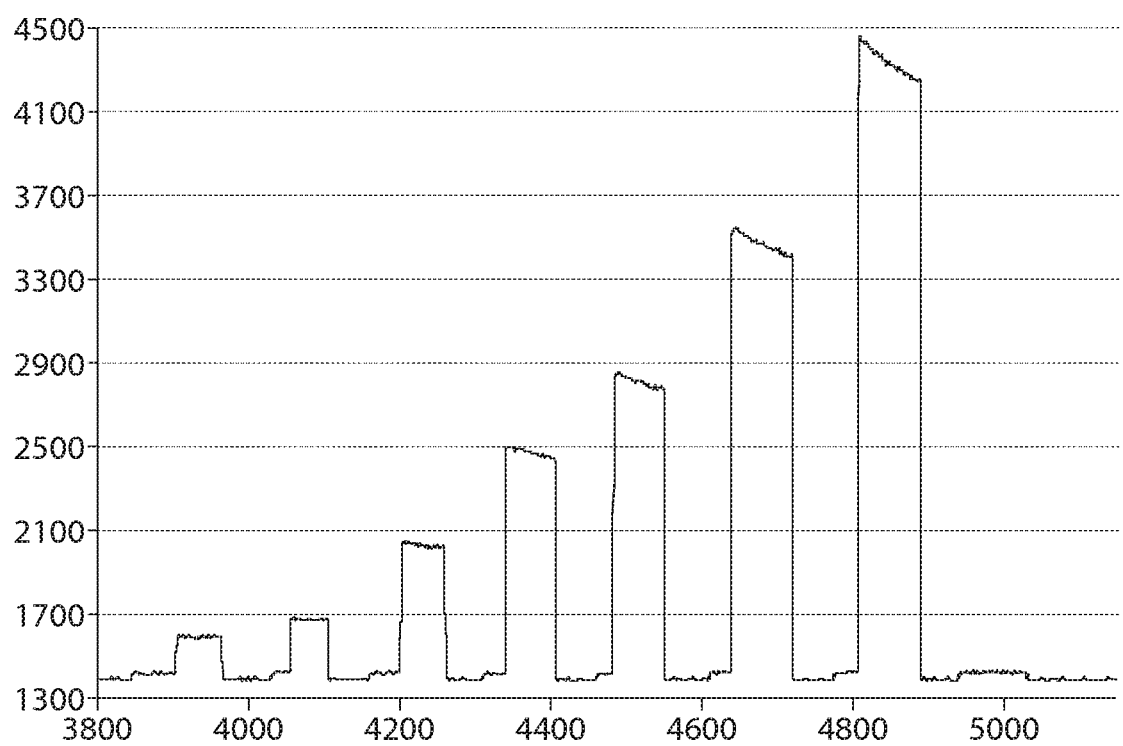
FIG. 16 shows a raw data plot of the output fluorescence signal from Alu PCR laser detection, according to an embodiment—peak intensities from left to right correspond to 0 ng, 0.4 ng, 1 ng, 4 ng, 10 ng, 20 ng and 40 ng input template DNA.

Fast PCR cycling profile reactions and quantification were as described in Example 2 with a modified amplification protocol of 20 seconds activation at 93° C. followed by 15-cycles of [93° C. for 4 seconds, 58° C. for 15 seconds, 70° C. for 7 seconds] and final extension for 90 seconds at 70° C. Completion time was approximately 10 minutes. A plot of input DNA versus relative fluorescence units (RFU) from the instrument has $R^2=0.999$ (FIG. 15). FIG. 16 is the output RFU data from laser detection as a function of lane displacement. During excitation, a filter that decreased the laser power strength by a magnitude compared to that used with TH01 reaction was found necessary to avoid photobleaching of the dye. An OD4 neutral density optical filter was used with laser power set to 200 mW, gain of blue PMT to 30% of full scale, gain of red, yellow, and green set to 0, and refresh rate at 5 Hz. At this laser power setting and filter combination, the effective laser power is 10% that of Example 2. This data suggests that cycle number during amplification can be further reduced.

Figure 17:
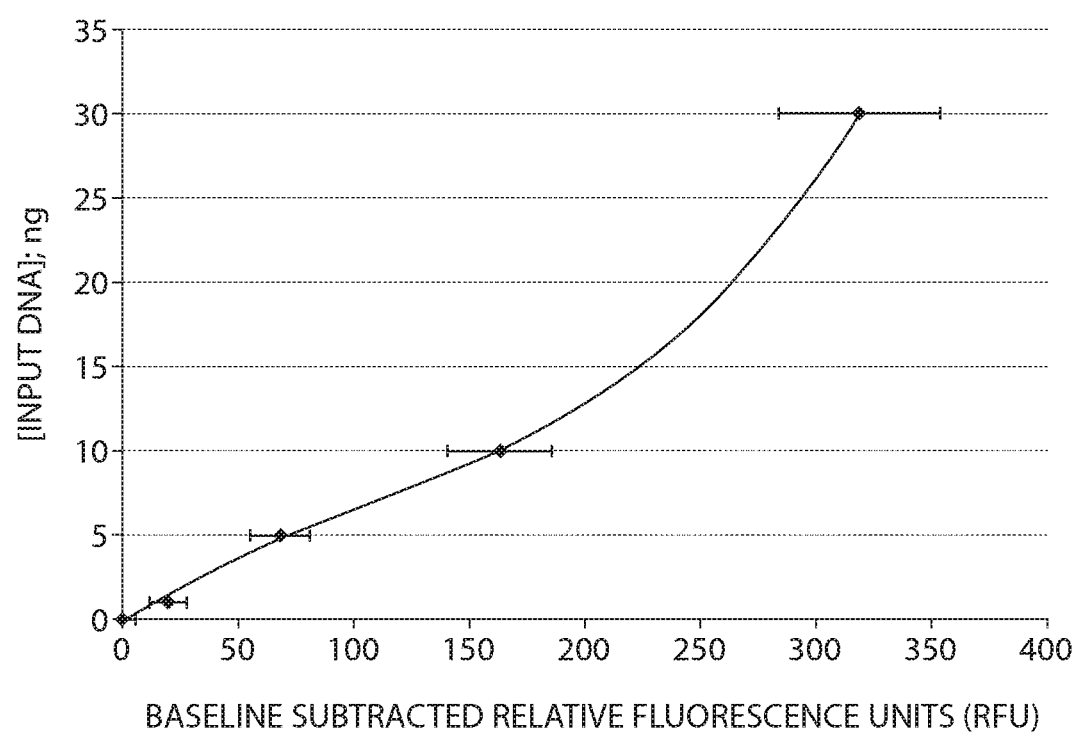
FIG. 17 shows a plot of input DNA (ng) versus baseline subtracted fluorescence signal (RFU) for the 10-cycle Alu PCR reaction showing repeatability of measurements, according to an embodiment—error bars represent 1 standard deviation.

To test this possibility, 15 samples were quantified each with input DNA of 1, 5, 10, and 30 ng using 10 amplification cycles, reducing amplification time by 2.5 minutes. The signal strength increases with increasing input DNA (FIG. 17). For 1 ng of input, the baseline subtracted signal strength is 19.9 RFU with a standard deviation of 10 RFU and a CV of 50%. For 5 ng of input, the baseline subtracted signal strength is 68 RFU with a standard deviation of 11 RFU and a CV of 17%.

Human genomic DNA, non-human DNA, and spiked human genomic were used to evaluate the assay as in Example 2. Cattle (*Bos Laurus*) and chicken (*Gallus domesticus*) were extracted from blood samples. All DNAs were prepared as in Example 2.

genomic DNA quantification. Alu amplification has the benefit of approximately one million-fold greater target than the TH01 amplification; thus, if amplification is 100% efficient, represents a requirement of approximately 8 amplification cycles as opposed to 28. The 10-fold reduced laser power in the Alu case represents approximately 3 additional required cycles. In theory, under these conditions, the Alu reaction should require 11 cycles to generate a signal comparable to the 28-cycle TH01 reaction. Although amplification of the two loci is unlikely to be identical, the observed results at 10 cycles closely match these theoretical considerations.

TABLE 2

| DNA Samples Tested | DNA amount (ng) Absorbance | Microfluidic Picogreen |
|---|---|---|
| Non-human Samples Only | | |
| *Bacillus subtilis* | 10 +/− 0 | None detected |
| *Bacillus cereus* | 9.9 +/− 0.1 | None detected |
| *Bacillus megaterium* | 9.8 +/− 0.3 | None detected |
| *Saccharomyces cerevisiae* | 20.5 +/− 0.7 | None detected |
| *Canis familiaris* | 9.5 +/− 0.7 | None detected |
| *Bos taurus* | 10 +/− 0 | 0.5 +/− 0.1 |
| *Gallus domesticus* | 10 +/− 0 | 1.4 +/− 1.1 |
| Non-human Samples Spiked with 10 ng Human DNA | | |
| 10 ng *Bacillus subtilis* + 10 ng Human DNA | 20 +/− 0 | 5.1 +/− 0.7 |
| 10 ng *Bacillus cereus* + 10 ng Human DNA | 19.9 +/− 0.1 | 5.5 +/− 0.5 |
| 10 ng *Bacillus megaterium* + 10 ng Human DNA | 19.8 +/− 0.3 | 5.5 +/− 0.8 |
| 20 ng *Saccharomyces cerevisiae* + 10 ng Human DNA | 30.5 +/− 0.7 | 8 +/− 1 |
| 10 ng *Canis familiaris* + 10 ng Human DNA | 19.5 +/− 0.7 | 9.9 +/− 0.6 |
| 10 ng *Bos taurus* + 10 ng Human DNA | 20 +/− 0 | 11.5 +/− 0.3 |
| 10 ng *Gallus domesticus* + 10 ng Human DNA | 20 +/− 0 | 11.3 +/− 2.5 |

Mock forensic casework samples were also used for evaluation. Wet blood samples on swabs were prepared by pipetting 100 μL of blood suspension onto a ceramic tile and then collecting the blood with cotton swabs. Dried blood samples were prepared similarly but allowed to dry overnight. Cellular samples were collected by rubbing the swab head (pre-wet with sterile water), on the palm of a human subject. Touch samples were prepared by using a pre-wet swab on a ceramic tile that was handled several times by a single donor. All DNA extractions were performed using the QIAmp Kit (Qiagen, Valencia, Calif.) following the manufacturer's protocol for isolation of genomic DNA from swabs.

TABLE 3

| DNA Samples Tested | DNA amount (ng) Absorbance | Microfluidic Picogreen |
|---|---|---|
| 10 ng Non-human Samples Only | | |
| Dry Human Whole Blood DNA | 18.9 +/− 2.6 | 22.0 +/− 0.1 |
| Wet Human Whole Blood Swab DNA | 11.5 +/− 0.7 | 14.6 +/− 1.2 |
| Wet Human Whole Blood Suspension DNA | 19.5 +/− 1.0 | 15.1 +/− 0.3 |
| Human Cellular Swab DNA | 3.9 +/− 0.1 | 5.9 +/− 0.5 |
| Human Touch Swab DNA | 8.3 +/− 1.0 | 9.0 +/− 0.1 |
| Human Adult Buccal Swab DNA | 9.5 +/− 0.7 | 9.8 +/− 2.8 |
| Human Baby Buccal Swab DNA | 10.2 +/− 0.3 | 8.3 +/− 2.2 |

Based on these data, it is clear that the microfluidic Alu Picogreen assay is highly sensitive and specific for human Using Alu probes, the combination of microfluidic volumes and laser detection leads to an LOD of 0.005 picograms of DNA. Without placement of an OD3-equivalent laser filter, the resulting LOD is 0.005 femtograms. This LOD is an order of magnitude better than the use of TH01 probes and the amplification and detection conditions of Example 2; the Alu probes and condition also allow a significant reduction in cycle number. In some embodiments, if LODs of less than 0.005 femtograms are required, one or more of the number of amplification cycles, the sequence and efficiency of the probe, and laser power can be increased.

Example 4

This example demonstrates DNA quantification by SYBR Green I assay.

The amplification reaction components including Alu primers described in Example 3 were used, with the exception that a 1:60,000 dilution of SYBR Green I (Invitrogen) in Tris EDTA Buffer (pH 8) was incorporated into the PCR mix. SYBR Green I is a thermally stable fluorescent dye and can therefore be added into the PCR mix as in real-time PCR assays.

Figure 18:
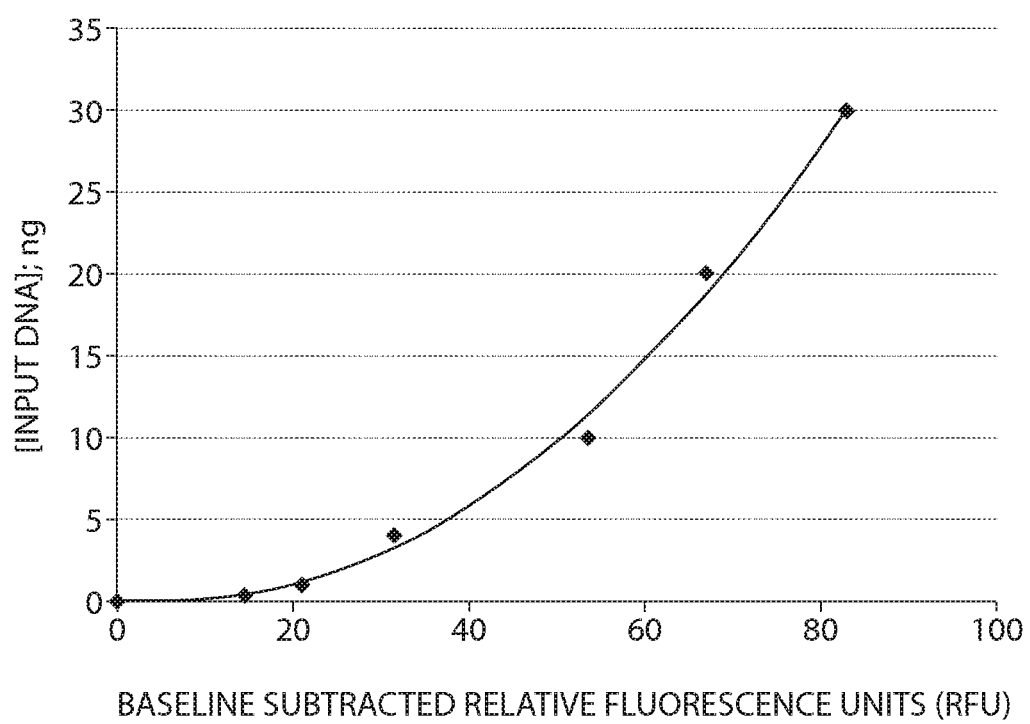
FIG. 18 shows a plot of input DNA (ng) versus baseline subtracted fluorescence signal (RFU) for a 7-cycle Alu PCR-SYBR Green assay, according to an embodiment.

To test workability of this faster assay, standard calibration curves were generated and reproduced. Genomic 9947A DNA standards were: 0 ng, 0.4 ng, 1 ng, 4 ng, 10 ng, 20 ng and 30 ng. Amplification was initiated with 20 seconds activation at 93° C. followed by 7-cycles of [93° C. for 4 seconds, 58° C. for 15 seconds, 70° C. for 7 seconds] and final extension for 90 seconds at 70° C. Completion time was 6 minutes. Following amplification, the same biochip was subjected to laser excitation with optical settings as in Example 3. PCR in biochip and lane detection were performed in quadruplicate to confirm reproducibility of the standard curve and that fluorescence increases with increase in input template DNA. A plot of input DNA versus RFU from from the instrument (FIG. 18) gave a polynomial fit with $R^2=0.995$. The advantage of this approach over the use of Picogreen dye is that amplification and detection can be performed in the identical chambers of the biochip, simplifying the overall process (e.g. eliminating the need to meter the Picogreen reagent and mix it with the post-amplification reaction) and biochip format.

Example 5

This example demonstrates DNA quantification without prior amplification by hybridization assay using molecular beacons.

Direct hybridization without amplification was utilized to quantify human genomic DNA. Two beacon probes were designed such that they target the repetitive human Alu elements. Probe 1 was derived from PV 92 gene and has the sequence 5'-GCC CGA TTT TGC GAC TTT GGA GGG C-3' (SEQ ID NO: 5) (Human Alu Repeat GenBank Accession Numbers: M57427.1/M33776, AF302689). Probe 2 was designed by alignment of known Alu-subfamilies and choosing a target region that was highly conserved. The sequence 5'-CGC CTC AAA GTG CTG GGA TTA CAG GCG-3' (SEQ ID NO: 6) was predicted to be a more sensitive probe. Both probes have fluorescein (6 FAM™) attached at the 5' end and Iowa Black Quencher (IB® FQ) attached at the 3' end (Integrated DNA Technologies [IDT], Coralville, Iowa).

The fluorescence buffer appropriate for Probe 1 contained: 40 mM NaCl, 5 mM $MgCl_2$ and 10 mM Tris-HCl (pH 8.0). The fluorescence buffer appropriate for Probe 2 contained: 1 mM $MgCl_2$ and 20 mM Tris-HCl (pH 8.0). The fluorescence buffers were chosen based on hybridization with an artificial ssDNA target which gave high signal-to-noise ratios. Melting temperatures ($T_m$) of the hybrid and the stem structure were determined using IDT SciTools Oligo-Analyzer 3.1 and mfold version 3.4 programs. The hybridization temperature was set to 53° C., a temperature below the $T_m$ of the hybrid and slightly higher than the $T_m$ of the stem.

22 μL sample reactions in desired fluorescence buffer were prepared with 2 μL of 10 μM molecular beacon and varying concentrations of human genomic DNA (0, 4.5, 9, 18, 32, 50 and 100 ng/μL) (Roche Applied Science, Indianapolis, Ind.). Approximately 7 μL was then transferred into the biochip of Examples 2-4 for thermal denaturation and hybridization. The thermal profile for the biochip was initiated with a single cycle of 10 seconds denaturation at 95° C. followed by hybridization for 60 seconds at 53° C. and cool down for 60 seconds at 25° C. The biochip was then subsequently analyzed in from the instrument. When probe 1 was utilized, laser power was set to 20 mW, gain of blue PMT to 30% of full scale with all the rest of the colors set to 0 and refresh rate at 10 Hz. For probe 2, however, use of an OD2 neutral density optical filter was necessary and the rest of the settings were implemented as in probe 1. This confirmed the increased sensitivity of probe 2 over probe 1. Samples were assessed in quadruplicates, and a set of control samples was prepared similarly but without human genomic DNA.

Figure 19:
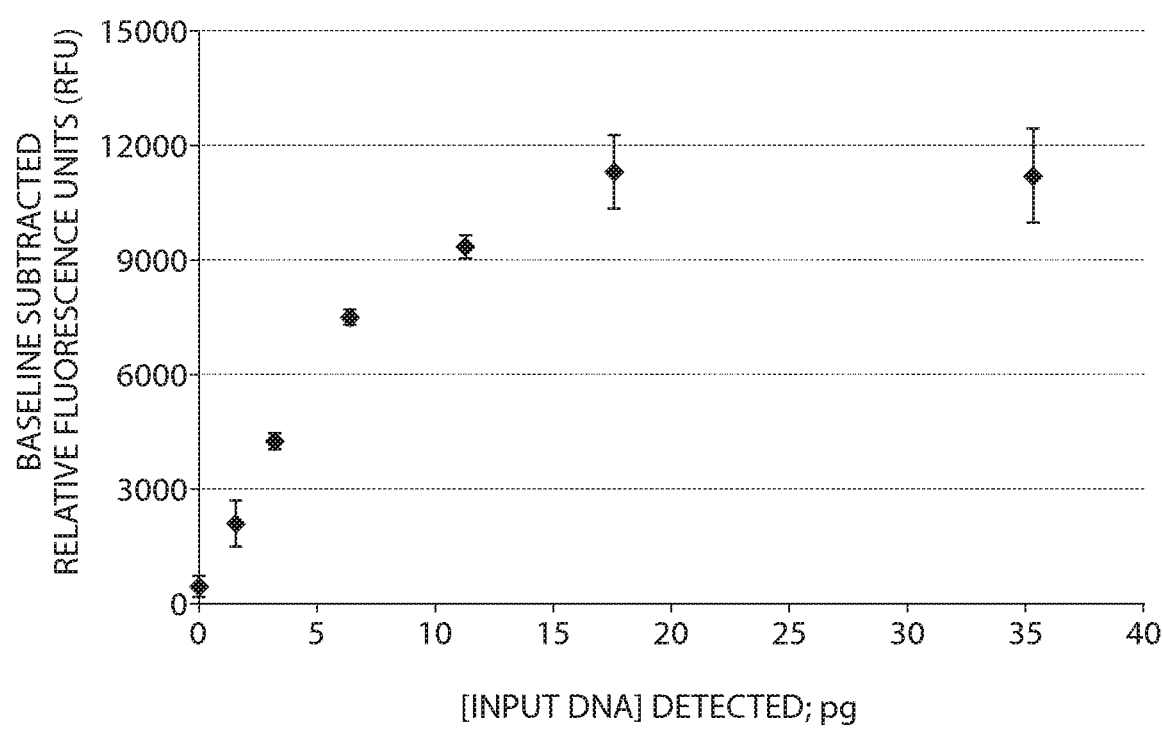
FIG. 19 shows a plot of baseline subtracted fluorescence signal (RFU) versus genomic DNA target concentration actually detected (pg) using molecular beacon probe 1 as described in Example 5, according to an embodiment.
Figure 20:
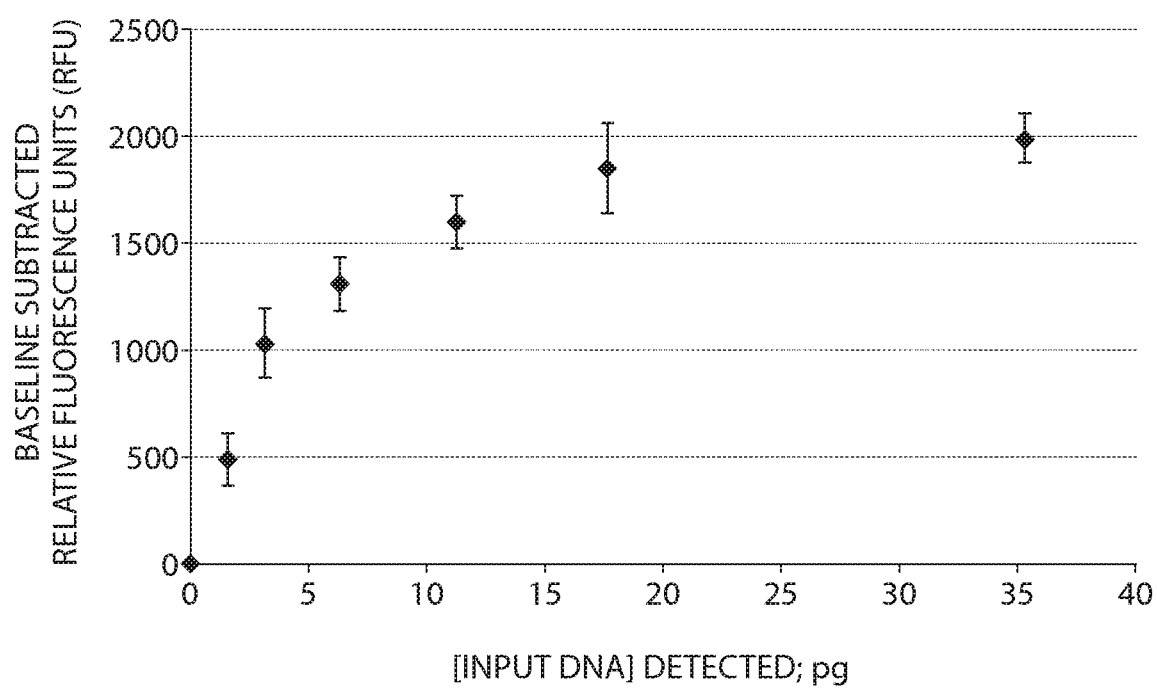
FIG. 20 shows a plot of baseline subtracted fluorescence signal (RFU) versus genomic DNA target concentration actually detected (pg) using molecular beacon probe 2 as described in Example 5, according to an embodiment.

FIG. 19 is the hybridization plot of RFU versus input DNA detected using molecular beacon probe 1. The average RFU signal for the negative control is 3427 RFU with SD of 216 RFU and for the 4.5 ng/μL total input was 4641 RFU with SD of 583 RFU. FIG. 20 is the hybridization plot using molecular beacon probe 2. The average RFU signal for the negative control was 3668 RFU with SD of 33 RFU and for the 4.5 ng/μL total input was 4075 RFU with SD of 83 RFU. Baseline subtracted RFUs were plotted against actual input DNA detected by laser. This translated the total human genomic DNA of 0, 4.5, 9, 18, 32, 50 and 100 ng/μL to 0, 1.6, 3.2, 6.4, 11.3, 17.6 and 35.3 picograms of DNA, respectively. Increase in signal due to hybrid formation increased with increasing target DNA present in the sample. The data demonstrated that the two probes consistently distinguished between 0 and 1.6 picograms of DNA. The LOD using probe 1 was 1.6 picograms. For probe 2, without the OD2 laser filter, the assay can detect approximately 16 femtograms of DNA. Note that this LOD is almost three orders of magnitude less than the DNA present in a single human cell (approximately 6 picograms) and allows effective quantification of trace forensic evidence.

As those skilled in the art will appreciate, modifications to the Alu beacons (e.g., using more highly conserved target sequences and coupled fluorophores with better quenching efficiency) can further improve the sensitivity and LOD of the direct hybridization approach. However, in terms of the Alu probes used in this example, direct hybridization has about the same sensitivity as that of the 10-cycle PCR-Picogreen assay. However, with respect to the process time, hybridization without amplification assay required only approximately two minutes, shortening the overall quantification by approximately 5 minutes. In addition, the direct hybridization offers a significant overall cost-reduction and simplifies the integrated microfluidic system since enzymes, dNTPs and PCR buffers which require real estate on the microfluidic biochip are not involved in the reaction. Finally, PCR inhibitors commonly present in clinical, environmental, and forensic samples should not inhibit the hybridization reaction.

Example 6

This example demonstrates reducing reaction time of the direct hybridization molecular beacon assay.

Figure 21:
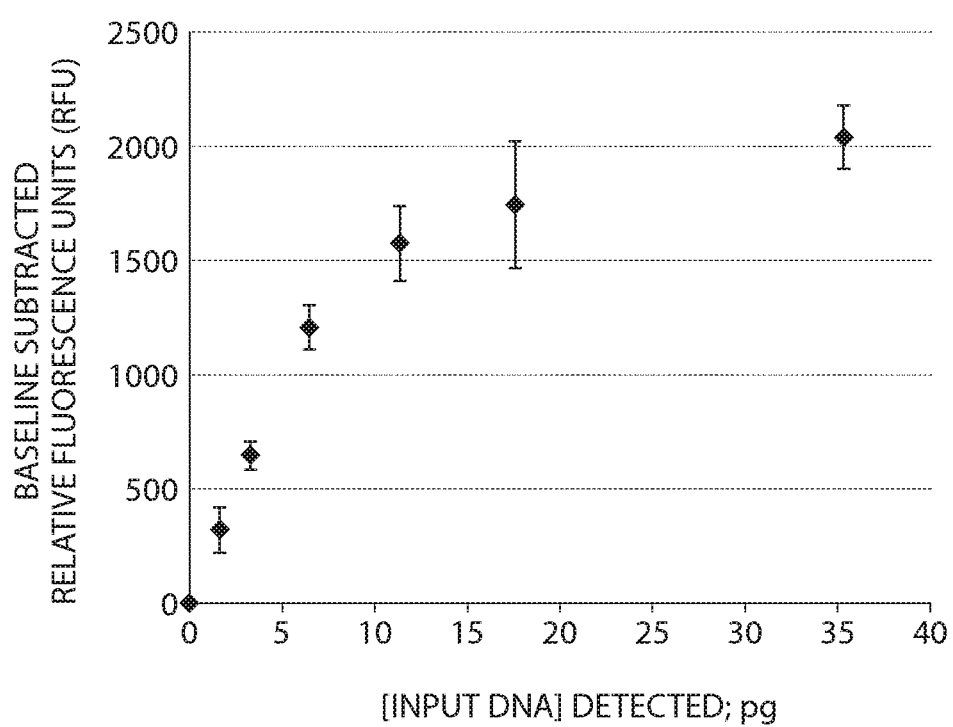
FIG. 21 shows a plot of baseline subtracted fluorescence signal (RFU) versus genomic DNA target concentration actually detected (pg) using 1-minute hybridization with molecular beacon probe 2 as described in Example 6, according to an embodiment.

Reaction conditions for molecular beacon probe 2 were carried out similarly to those of Example 5 but with a single cycle of 10 seconds denaturation at 95° C. followed by hybridization for 30 seconds at 53° C. and final cool down for 10 seconds at 25° C. The same optical settings were also implemented. FIG. 21 is the hybridization plot of RFU versus input DNA translated to actual picograms DNA quantified and detected. The average RFU signal for the negative control is 3321 RFU with SD of 105 RFU and for 1.6 picograms is 3806 RFU with SD of 61 RFU. The data suggests that reducing the overall quantification time from to 130 seconds to 50 seconds had no effect on the assay. In fact, further optimization (with and without an improved probe) will allow assay time to be reduced to less than 15 seconds (e.g. denaturation of 3 seconds, hybridization of 10 seconds, and cool down of 1 second).

Example 7

This example demonstrates direct hybridization molecular beacon assay to quantify human buccal swab DNA.

From the standard curve of Example 6, fluorescence signals of buccal swab DNAs from male and female human subjects were extrapolated and compared with values obtained from UV absorbance.

TABLE 4

| DNA Samples Tested | DNA amount (pg) | |
|---|---|---|
| | Absorbance | Beacon Assay |
| Human Adult Male Buccal Swab DNA | 105.3 +/− 0.1 | 112.4 +/− 22.7 |
| Human Adult Female Buccal Swab DNA | 152.2 +/− 0.6 | 152.2 +/− 53.7 |

Example 8

This example demonstrates specificity of the direct hybridization molecular beacon assay. Non-human DNAs were purified as described. From the standard curve of Example 6, fluorescence signals from bacteria, canine, and chicken DNAs were again extrapolated and compared with values obtained from UV absorbance. In addition, a known human buccal swab DNA sample was spiked with these different background DNAs.

TABLE 5

| DNA Samples Tested | DNA amount (pg) | |
|---|---|---|
| | Absorbance | Beacon Assay |
| Non-human Samples Only | | |
| Bacillus cereus | 436.4 +/− 3.5 | 38.6 +/− 32.4 |
| Saccharomyces cerevisiae | 327.3 +/− 3.2 | 74.8 +/− 1.1 |
| Canis familiaris | 210.4 +/− 0.6 | 84.4 +/− 13.7 |
| Gallus domesticus | 234.9 +/− 1.4 | 73.1 +/− 36.9 |
| Human DNA Spiked Samples | | |
| 436.4 pg Bacillus cereus + 105.3 pg Human DNA | 542 | 119.3 +/− 2.0 |
| 210.4 pg Canis familiaris + 105.3 pg Human DNA | 316 | 101.2 +/− 24.5 |
| 234.9 pg Gallus domesticus + 105.3 pg Human DNA | 340 | 105.2 +/− 12.0 |

Although non-human DNAs from the beacon assay gave fluorescence signals slightly above background, this artifact is likely due to buffer effects. Background DNA samples used in the assay were resuspended in TE buffer and not in fluorescence buffer. It was noted previously that beacons buffer components can contribute to the detected fluorescence. Fast direct hybridization allows human-specific DNA quantification in heterogeneous samples.

Example 9

This example demonstrates eliminating the need for quantification with forensic database samples.

The amount of DNA collected by buccal swabbing is highly variable and ranges from approximately 100 ng to greater than 10 µg, although the majority of samples contain between 500 ng and 4 µg of DNA. In the laboratory, this variability has minimal impact on the overall STR typing process as purified DNA is subjected to quantification, and a desired amount of DNA is utilized in the subsequent PCR reaction.

Buccal swab DNA was purified using a guanidinium-based silica binding approach modified from that described in U.S. patent application Ser. No. 12/699,564, entitled "Nucleic Acid Purification," filed Feb. 3, 2010, by Selden et al., which is incorporated herein by reference. Buccal cell samples from 15 human subjects were obtained as described in Example 3. The swab's shaft was cut at score line to fit into a 2 mL microcentrifuge tube. A master mix of lysis buffer containing guanidinium hydrochloride and detergent solution, and proteinase K (Qiagen, Valencia, Calif.) was prepared. 500 µL of this lysis solution containing 0.5 mg of proteinase K was transferred into each of the tubes. The solution was thoroughly mixed by vortexing for 5 seconds. 550 µL absolute ethanol was added to the mixture and again vortexed for 5 seconds. 100 µL of the homogenized flow-through was manually loaded into the biochip's input port. This biochip has a 1.5 mm DNA-binding silica membrane for purification. The binding membrane was washed with 2 mL of ethanol-isopropanol-NaCl wash solution. Prior to elution, the binding membrane was allowed to dry for 30 seconds. DNA was eluted with 600 µL of TE-4 (10 mM Tris-HCl, pH 8 and 0.1 mM EDTA).

Following generation of reference sample DNA, 7 µL PCR reaction mixes contained 3.4 µL of the biochip-purified DNA and 1× Powerplex16 primers (Promega Corporation, Madison, Wis.) were prepared. Note that no quantification step was performed prior to amplification—a fixed volume of the purified DNA was always used for the amplification reaction. As a control, a standard 1 ng 9947A genomic DNA diluted from stock in TE-4 was also amplified. Amplification started with 20 seconds activation at 93° C. followed by 30 cycles of [93° C. for 4 seconds, 56° C. for 20 seconds, 70° C. for 20 seconds] and final extension for 90 seconds at 70° C. Completion time was approximately 25 minutes.

DNA samples for analysis from the instrument were prepared by manually pipetting the samples into the sample reservoirs of the separation biochip. In particular, 2.7 µL of the amplified product, 0.3 µL of HD400 sizing standard, and 10 µL of HiDi were mixed together and loaded into the sample wells. After loading the samples and buffers, the biochip was placed into the instrument with electric fields applied to separate and detect the amplified DNA. Instrument and detections were performed in duplicate for each buccal swab DNA sample amplified. Peak heights of homozygous alleles at a given locus were divided by 2 to allow comparisons with peak heights of heterozygous alleles at the corresponding locus. Average peak heights of all loci from the 1 ng input 9947A control DNA were used to estimate the quantity of input DNA into the PCR reactions. Based on this signal strength analysis, the quantity of DNA from the 15 buccal swab extracts were all within the 1.26-2.50 ng, and most samples contained between 1.5 and 2.25 ng per 3.4 µL into PCR.

TABLE 6

| Sample | [PCR Input DNA] (ng/µL) |
|---|---|
| 1 | 0.71 |
| 2 | 0.61 |
| 3 | 0.64 |
| 4 | 0.61 |
| 5 | 0.52 |
| 6 | 0.54 |
| 7 | 0.54 |
| 8 | 0.58 |
| 9 | 0.64 |
| 10 | 0.41 |
| 11 | 0.49 |
| 12 | 0.56 |
| 13 | 0.47 |
| 14 | 0.46 |
| 15 | 0.47 |
| Control 9947 A | 0.29 |

Figure 22:
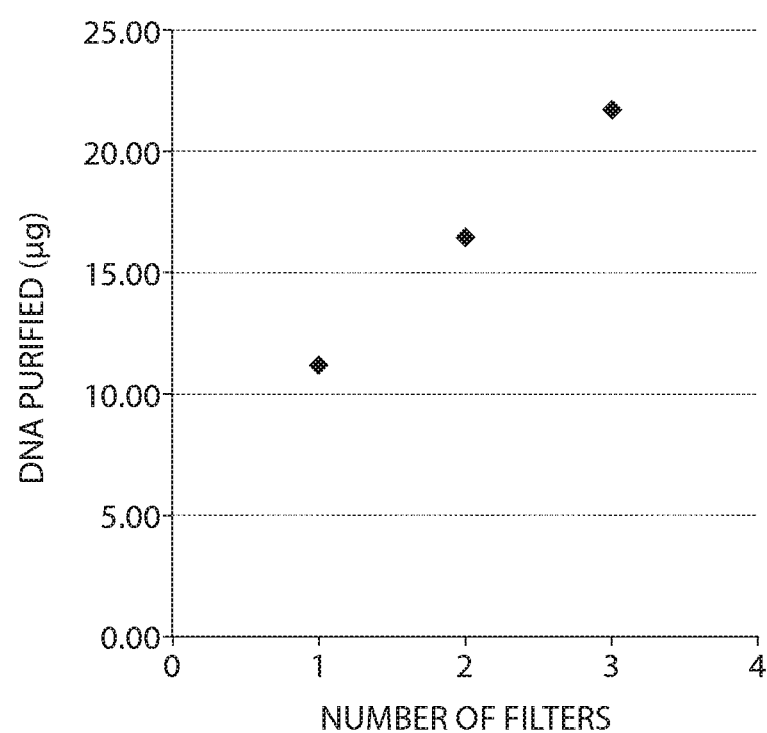
FIG. 22 demonstrates DNA binding "cut-off" as a function of the number of purification filter layers as described in Example 9, according to an embodiment.
Figure 23:
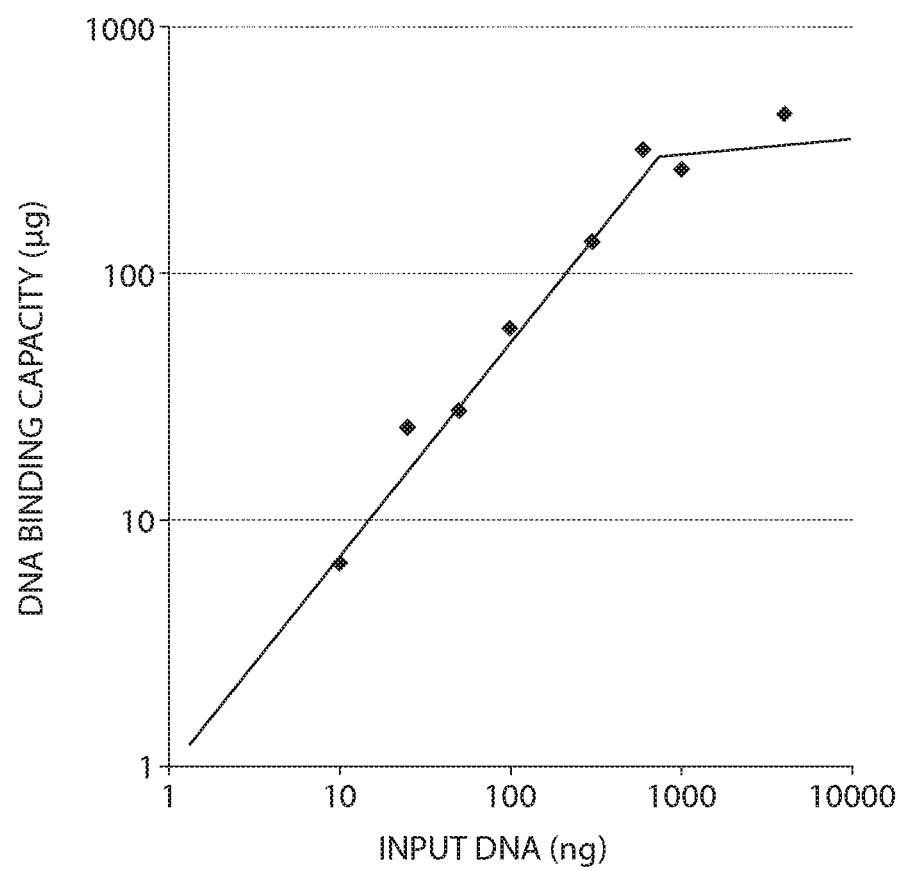
FIG. 23 demonstrates DNA binding performance of a 1 mm diameter filter over a range of input DNA as described in Example 9, according to an embodiment.

The variable recovery in swab purification and the enormous excess of recovered DNA have been addressed by controlling the binding capacity of the binding membrane. FIG. 22 demonstrates this "cut-off" approach. DNA binding capacity scales with the number of layers of a 7 mm silica membrane used for DNA binding. Similarly, the binding capacity of the binding membrane also scales with the active diameter of the binding membrane. FIG. 23 shows the binding performance of a 1 mm diameter binding membrane over a range of DNA inputs. The DNA yield increases linearly with DNA input level for input levels below 600 ng, and the yield saturates at approximately 300 ng of DNA for inputs of 600 ng or more. In a setting in which microfluidic DNA purification is integrated with amplification (or other processing steps as desired), knowledge of the range of recovered DNA allows significant flexibility in biochip design. In the processing of forensic reference samples, a fraction of the lysate may be subjected to purification (note that the 1.26-2.50 ng of DNA used for PCR translates to 220-440 ng of DNA in the 600 µL elution volume as only a tenth of the lysate material was purified). By reducing the quantity of DNA to be purified, the binding capacity of the purification media can be reduced concomitantly. The ability to generate purified nucleic acids within a predetermined, defined range without quantification can simplify biochip design, further reduce cost, and further accelerate process timing.

Example 10

This example demonstrates development of excitation and detection parameters for quantification based on a specific optical train.

Figure 25:
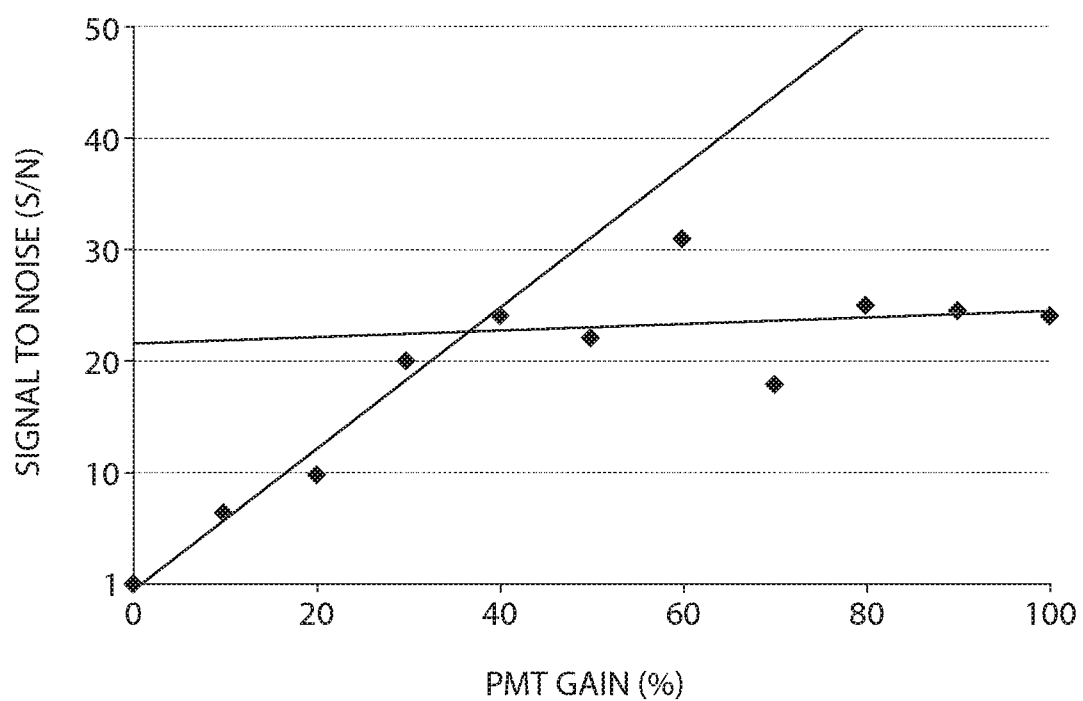
FIG. 25 shows a plot of signal-to-noise ratios as the PMT gains are swept across the operation range as discussed in Example 10, according to an embodiment.

A master mix of DNA and Picogreen intercalating dye was prepared and inserted into the quantification biochip and used for excitation and detection with the quantification instrument. Under laser excitation, detector signal strength increased with increasing PMT gain. Signal strength increased over 3 orders of magnitude, from 10 RFU and 10,600, as the PMT gains were swept across their operation range (FIG. 24). The signal to noise ratio increased with increasing PMT gain, up to a setting of 30%, and saturates at approximately 22 for PMT gains of 30% and higher. This data set shows that a PMT gain setting of 30% noise contribution associated with the detection electronics was negligible. The gain setpoint of 30% was optimal for use to maximize signal-to-noise, signal strength, and dynamic range (FIG. 25).

Figure 26:
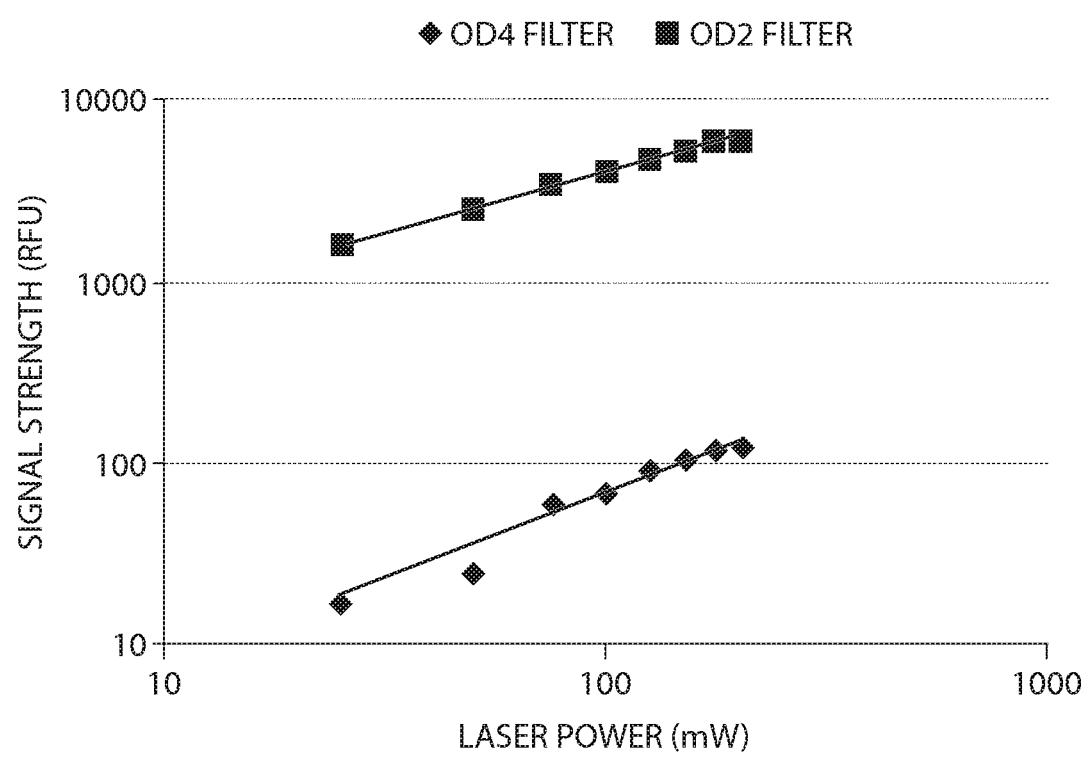
FIG. 26 shows a plot of signal strength as a function of laser power as discussed in Example 10, according to an embodiment.
Figure 27:
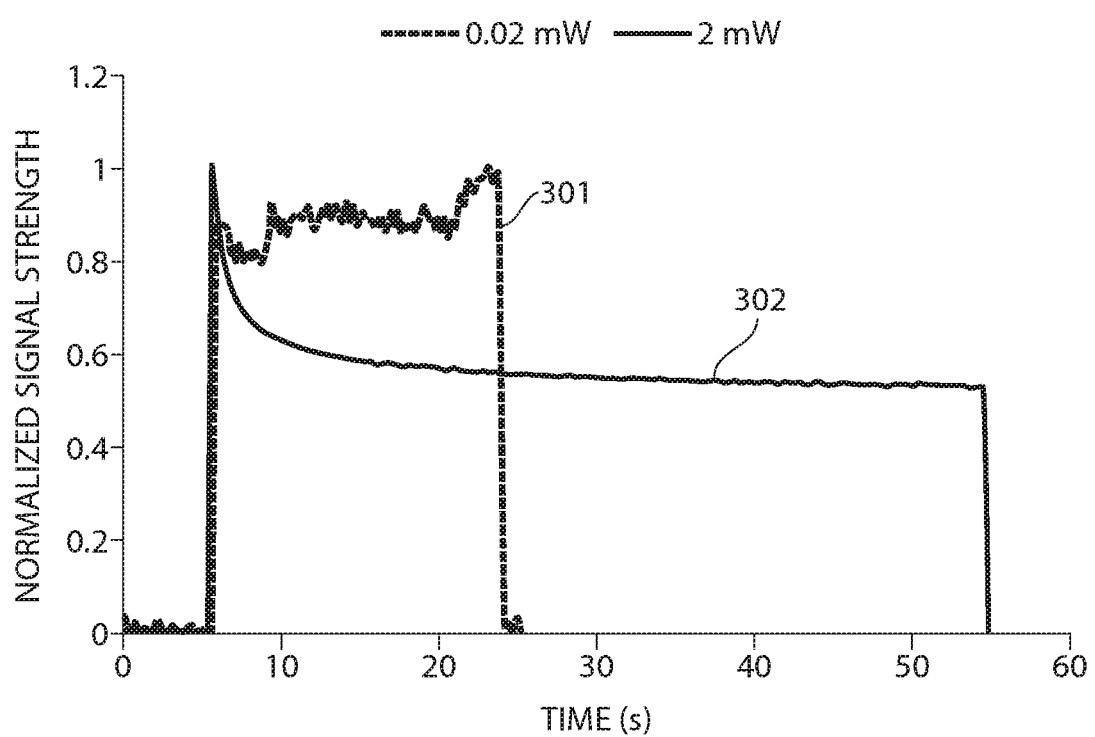
FIG. 27 shows the photobleaching phenomenon with excitation level as discussed in Example 10, according to an embodiment.

The effect of laser excitation on signal strength is shown in FIG. 26. The two datasets were generated using neutral density optical filters, with optical densities of 4 and 2, to reduce the excitation power at the sample by 10000 and 100 times that of the laser output. The data shows signal strength increasing with excitation power for both datasets. A moderate excitation power (0.02 mW) incident on the sample generated a relatively constant signal strength over time. This signal strength was consistent with the concentration of fluorophores in the sample. A high level of excitation (2 mW) incident on the sample exhibit an exponential decay to a level that was independent of the number of fluorophores in the sample. The high level of excitation incident on the sample resulted in photochemical destruction of a fluorophore, also known as photobleaching, and an irreversible loss of fluorescence activity in the sample (FIG. 27). These results show that a sample excitation power of 0.2 mW was optimal for quantification. Taken together, the results show that a PMT gain of 30% and an excitation power of 0.2 mW are setpoints to achieve optimal signal-to-noise, sensitivity, dynamic range with the excitation and detection instrument.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A system comprising: (a) a biochip comprising a plurality of microfluidic systems, wherein each microfluidic system comprises one or a plurality of first reaction chambers, each adapted for microfluidic quantitation, wherein each of said plurality of said first reaction chambers further comprises a first detection position, and a separation chamber, wherein the separation chamber comprises a second detection position;
  (b) a data acquisition and storage system;
  (c) a quantitation system, comprising;
    (i) one or a plurality of first reaction chambers, each adapted configured for a quantitation assay or method that determines the amount of a measurable characteristic which may be correlated to the amount of said one or a plurality of target analytes in the quantitation chamber;
    (ii) one or more light sources positioned to illuminate the first detection positions on the biochip;
    (iii) one or a plurality of first optical elements positioned for collecting and directing light emanating from said first detection positions; and
    (iv) a light detector positioned to accept light directed from the first optical elements, wherein the light detector comprises a wavelength dispersive element configured to separate the light from the first optical elements according to light wavelength and positioned to provide a portion of the separated light to at least one detection elements, wherein each of the detection elements are in communication with said data acquisition and storage system and are configured for simultaneously collecting detection information from each of the detection elements; and wherein said light detector being is configured to detect fluorescence from at least one dye labeled to one or more biological molecules to be quantitated, each dye having a unique peak emission wavelength, where the measurable characteristic is correlated to the amount of said one or a plurality of target analytes in the quantitation chambers;
  (d) a separation and detection system, comprising;
    (i) a separation element configured for simultaneously separating one or a plurality of target analytes in the separation chamber;
    (ii) one or more light sources positioned to illuminate the second detection positions on the biochip;
    (iii) one or a plurality of first optical elements positioned for collecting and directing light emanating from said second detection positions; and
    (iv) a light detector positioned to accept light directed from the first optical elements, wherein the light detector comprises a wavelength dispersive element configured to separate the light from the first optical elements according to light wavelength and positioned to provide a portion of the separated light to at least one detection element, wherein each of the detection elements are in communication with said data acquisition and storage system and are configured for simultaneously collecting detection information from each of the detection elements; and wherein said light detector being is configured to detect fluorescence from at least one dye labeled to one or more biological molecules, each dye having a unique peak emission wavelength, where the separation element is for simultaneously separating one or a plurality of target analytes in the separation chambers; and
  (e) a translational mirror in communication with a first control element and configured for setting a first excitation and detection beam path for said quantitation system or a second excitation and detection beam path for said separation and detection system.

2. The system of claim 1 wherein the translational mirror is used for preliminary, simultaneous or sequential quantitation of nucleic acid in each of the detection positions, and for the excitation and detection of multiple samples to steer both the excitation and detection beam paths in order to image each of the lanes of the biochip.

3. The system of claim 1 wherein the quantitation system uses an excitation beam that is directed to a lens, a first scanning mirror and a lens and objective assembly.

4. The system of claim 1 wherein in element (c)(1) said one or a plurality of first reaction chambers, is each adapted for a quantitation assay or method that determines the amount of a measurable characteristic which may be correlated to the amount of said one or a plurality of target analytes in the quantitation chamber without prior amplification.

5. The system of claim 1 wherein the separation element comprises a set of dichroic mirrors and a bandpass filters or a spectrograph or a prism.

6. The system of claim 1 wherein the light detector comprises a PMT, a multi-element PMT, a multielement photodiode a CCD camera a back sided CCD camera or a multi-element PMT.

7. The system of claim 6 wherein the light detector is a 32 element PMT detector array.

8. The wavelength of claim 1 where dispersive elements comprise prisms, diffraction gratings, transmission gratings and spectrographs.

\* \* \* \* \*